(12) United States Patent
Jordan et al.

(10) Patent No.: US 7,534,766 B2
(45) Date of Patent: May 19, 2009

(54) GLUCURONIDE METABOLITES AND EPIMERS THEREOF OF TIGECYCLINE

(75) Inventors: Ronald A. Jordan, Richboro, PA (US); William DeMaio, Collegeville, PA (US); Matthew Hoffmann, Pottstown, PA (US)

(73) Assignee: Wyeth, Madison, NJ (US)

( * ) Notice: Subject to any disclaimer, the term of this patent is extended or adjusted under 35 U.S.C. 154(b) by 182 days.

(21) Appl. No.: 11/265,790

(22) Filed: Nov. 2, 2005

(65) Prior Publication Data
US 2006/0128950 A1 Jun. 15, 2006

Related U.S. Application Data

(60) Provisional application No. 60/625,121, filed on Nov. 5, 2004.

(51) Int. Cl.
A61K 31/70 (2006.01)
C07H 15/24 (2006.01)
C07H 1/00 (2006.01)

(52) U.S. Cl. ............... 514/23; 536/6.4; 536/124
(58) Field of Classification Search .......... 536/6.4, 536/124; 514/23
See application file for complete search history.

(56) References Cited

U.S. PATENT DOCUMENTS

| 5,529,990 A | 6/1996 | Hlavka et al. |
| 2005/0148553 A1 | 7/2005 | Testa et al. |

FOREIGN PATENT DOCUMENTS

| EP | 0 536 515 | 4/1993 |
| EP | 0 582 788 | 2/1994 |
| EP | 0 582 789 | 2/1994 |
| EP | 0 582 790 | 2/1994 |
| EP | 0 582 810 | 2/1994 |
| WO | WO 2005/009943 | 2/2005 |
| WO | WO 2005/009944 | 2/2005 |

OTHER PUBLICATIONS

Beidenbach et. al. "In vitro antimicrobial activity of GAR-936 tested against antibiotic-resistant gram-positive blood stream infection isolates and strains producing extended-spectrum beta-lactamases" Diagn. Microbiol. Infect. Dis. 40(4):173-7 (Aug. 2001).
Betrieu, C. et al. "In vitro activities of tigecycline against erythromycin-resistant Streptococcus pyogenes and Streptococcus agalactiae: mechanisms of macrolide and tetracycline resistance" Antimicrob. Agents Chemother. 48:323-5 (Jan. 2004).
Bocker, R.H. et al. "Identification and determination of the two principal metabolites of minocycline in humans" J. Chromatog. 568:363-74 (1991).
Bradford, P.A. "Tigecycline: a first in class glycylcycline" Clin. Microbiol. Newsletter 26(21):163-8 (Nov. 1, 2004).
Bradford, P.A. et al. "Tigecycline MIC testing by broth dilution requires use of fresh medium or addition of the biocatalytic oxygen-reducing reagent oxyrase to standardize the test method" Antimicrob. Agents Chemother. 49(9):3903-9 (Sep. 2005).
Degenkolb, J. et al. "Structural requirements of tetracycline-Tet repressor interaction: determination of equilibrium binding constants for tetracycline analogs with the Tet repressor" Antimicrob. Agents Chemother. 35(8):1591-5 (Aug. 1991).
Fraise, A.P. et al. "In-vitro activity of two glycylcyclines against enterococci resistant to other agents" J. Antimicrob. Chemother. 35(6):877-81 (Jun. 1995) Erratum in: J. Antimicrob. Chemother. 37(5):1046 (May 1996).
Hirata, T. et al. "Effects of efflux transporter genes on susceptibilty of Escherichia coli to tigecycline (GAR-936)" Antimicrob. Agents Chemother. 48(6):2179-84 (Jun. 2004).
Hunter, P.A. et al. "GAR-936. Tetracycline Antibiotic. Tigecycline; TBG-MINO; WAY-GAR-936" Drugs of the Future 26(9):851-8 (2001).
Kamel, A.M. et al. "Mass spectral characterization of tetracyclines by electrospray ionization, H/D exchange, and multiple stage mass spectrometry" J. Am. Soc. Mass. Spectrom. 13:543-57 (May 2002).
MacDonald, H. et al. "Pharmacokinetic studies on minocycline in man" Clin. Pharmacol. Therapeut. 14:852-61 (1973).
Milatovic, D. "Activities of the glycylcycline tigecycline (GAR-936) against 1,924 recent European clinical bacterial isolates" Antimicrob. Agents Chemother. 47(1):400-4 (Jan. 2003).
Mitscher, L.A. The Chemistry of the Tetracyline Antibiotics. Grunwald, Gary L. [ed.], Marcel Dekker, Inc., New York; Chapter 6.3, p. 172-173 and Chapter 2, p. 53-54 (1978).
Nelis, H.J. et al. "Metabolism of minocycline in humans" Drug. Metab. Dispos. 10(2):142-6 (Mar.-Apr. 1982).
Patel, R. "In vitro activity of GAR-936 against vancomycin-resistant enterococci, methicillin-resistant Staphylococcus aureus and penicillin-resistant Steptococcus pneumoniae" Diagn. Microbiol. Infect. Dis. 38(3):177-9 (Nov. 2000).
Petersen, P.J. et al. "In vitro and in vivo activities of tigecycline (GAR-936), daptomycin, and comparative antimicrobial agents against glycopeptide-intermediate Staphylococcus aureus and other resistant gram-positive pathogens" Antimicrob. Agents Chemother. 46(8):2595-601 (Aug. 2002).
Petersen, P.J. et al. "In vitro and in vivo antibacterial activities of a novel glycylcycline, the 9-t-butylglycylamido derivative of minocycline (GAR-936)" Antimicrob. Agents Chemother. 43(4):738-44 (Apr. 1999).
Remmers, E.G. "Some observations on the kinetics of the C.4 epimerization of tetracycline" J Pharm Sci. 52:752-6 (Aug. 1963).
Renner, U.D. et al. "The oxidative biotransformation of losoxantrone (CI-941)" Drug Metab Dispos. 30(4):464-78 (Apr. 2002).

(Continued)

Primary Examiner—Shaojia Anna Jiang
Assistant Examiner—Everett White
(74) Attorney, Agent, or Firm—Andrea Dorigo; A. David Joran

(57) ABSTRACT

A glucuronide metabolite of tigecycline, and its corresponding epimer, have been identified in humans treated with tigecycline. Mass spectral data have been used to identify these structures.

24 Claims, 44 Drawing Sheets

OTHER PUBLICATIONS

Rubinstein, E. et al. "Tigecycline: A novel glycylcycline" Drugs 65(10):1317-36 (2005).

Schnappinger, D. et al. "Tetracyclines: antibiotic action, uptake, and resistance mechanisms" Arch. Microbiol. 165(6)359-69 (Jun. 1996).

Sesoko, S. et al. "Pharmacokinetics (PK), safety, and tolerability of tigecycline (GAR-936) in healthy Japanese males" 42nd ICAAC Abstracts, American Society for Microbiology, Sep. 27-30, 2002, San Diego, CA; Abstr. A-1403, p. 22 (2002).

Smith, K.L. et al. "Tigecycline" Formulary 40:245-254 (2005).

Subramanyam, V. et al. "Pharmacokinetics of glycylcylines in laboratory animals" 33rd ICAAC Abstracts, American Society for Microbiology, Oct. 17-20, 1993, New Orleans, LA; Abstr. 1706, p. 205 (1993).

Sum, P.-E. et al. "Synthesis and structure-activity relationship of novel glycylcycline derivatives leading to the discovery of GAR-936". Bioorg. Med. Chem. Lett. 9(10):1459-62 (May 17, 1999).

Tally, F.T. et al. "Glycylcyclines: a new generation of tetracyclines" J. Antimicrob. Chemother. 35:449-52 (1995).

Wilcox, M.H. "Tigecycline and the need for a new broad-spectrum antibiotic class" Surg. Infect. 7(1):69-80 (Feb. 2006).

Zhanel, G.G. et al. "The glycylcyclines: a comparative review with the tetracyclines" Drugs 64(1):63-88 (2004).

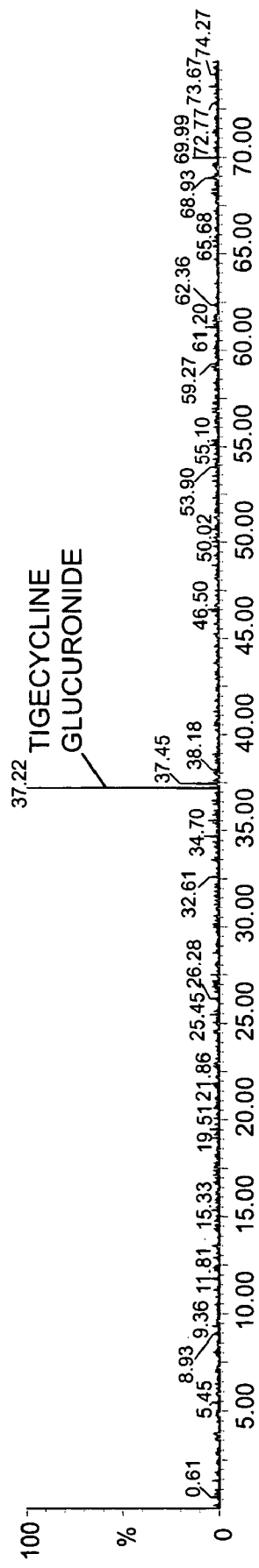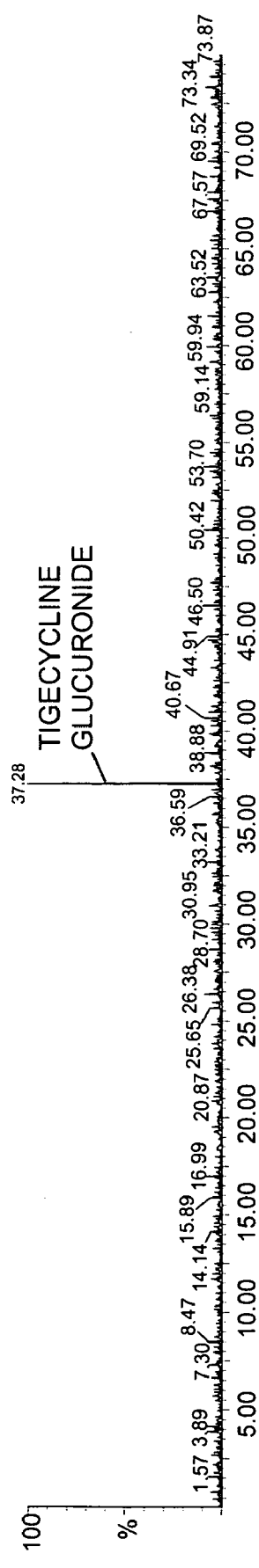
FIG. 21A
FIG. 21B

GLUCURONIDE METABOLITES AND EPIMERS THEREOF OF TIGECYCLINE

This application claims the benefit of priority from U.S. Provisional application No. 60/625,121, filed Nov. 5, 2004, the disclosure of which is incorporated herein by reference.

This invention relates to glucoronides, more particularly glucoronide derivatives of tigecycline, processes for preparing them and pharmaceutical compositions containing them.

Tigecycline (GAR-936) is a glycylcycline antibiotic and an analog of the semisynthetic tetracycline, minocycline. It was developed in response to the worldwide threat of emerging resistance to antibiotics. Tigecycline has broad-spectrum antibacterial activity both in vitro and in vivo. Glycylcycline antibiotics, like tetracycline antibiotics, act by inhibiting protein translation in bacteria.

Glycylcyclines, including tigecycline, are active against many antibiotic-resistant gram-positive pathogenic bacteria, such as methicillin-resistant *Staphylococcus aureus*, penicillin-resistant *Streptococcus pneumoniae*, and vancomycin-resistant enterococci (Weiss et al., 1995; Fraise et al., 1995). Of great significance is the activity of tigecycline against bacterial strains carrying the two major forms of tetracycline resistance, efflux and ribosomal protection (Schnappinger and Hillen, 1995).

Tetracycline antibiotics undergo little or no metabolism. Minocycline 9-hydroxylation and N-demethylation have been reported in humans, but only to a limited extent (Nelis and DeLeenheer, 1982). Epimerization at the C4 position has also been reported for most tetracycline antibiotics and is generally considered as degradation rather than a metabolic pathway (Remmers et al., 1963). The metabolic disposition of [$^{14}$C]tigecycline following an intravenous administration to healthy male volunteers was analyzed, and the results from the current study were also compared to the results obtained from pre-clinical metabolism studies in rats and dogs.

Following intravenous administration of [$^{14}$C]tigecycline to healthy, male volunteers, an analysis was performed on the radiolabeled tigecycline-based components in serum, urine and feces. Similar results were reported following analysis of human serum and urine following intravenous administration of non-radioactive tigecycline to male volunteers, where minimal metabolism was reported. The nonlabeled studies were consistent with results from metabolism studies using rats and dogs, where tigecycline was the major compound-related component in plasma and urine following intravenous administration.

Here, the epimer of tigecycline and M3a (t-butylaminoacetic acid) were also observed in each matrix. The epimer of tigecycline has been shown to be a degradant rather than a metabolite, and has been observed in rat and dog, plasma and urine, and human serum and urine. The amount of the tigecycline epimer in the serum and fecal samples is likely overestimated since much of the tigecycline is converted to the epimer during the extraction procedures used for these matrices. An early eluting chromatographic peak, presumed to be M3a, has also been observed in rat and dog, plasma and urine.

The tigecycline-related compounds detected in serum, urine and feces from the current study are shown in Scheme 1.

Scheme 1. [$^{14}$C]Tigecycline-Related Compounds Detected in Human Serum, Urine and Feces

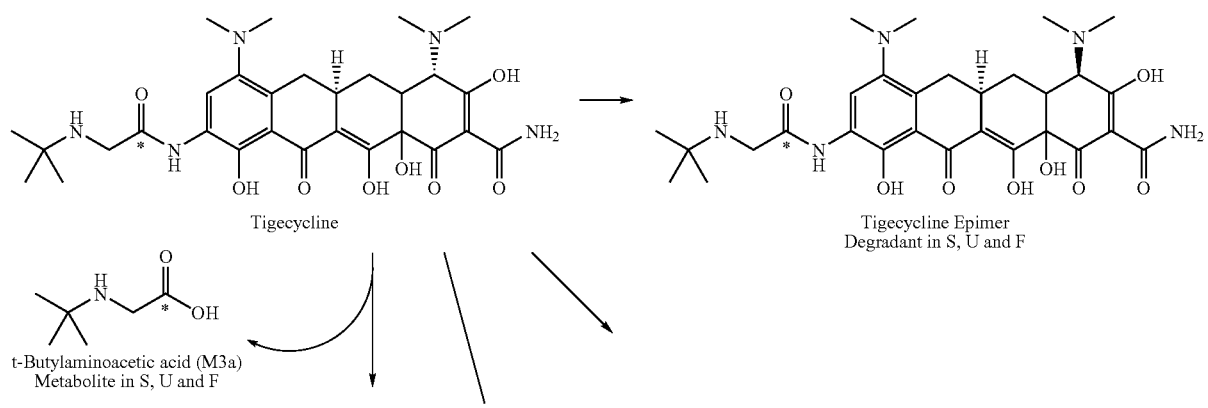

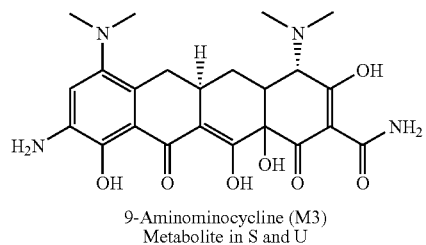

9-Aminominocycline (M3)
Metabolite in S and U

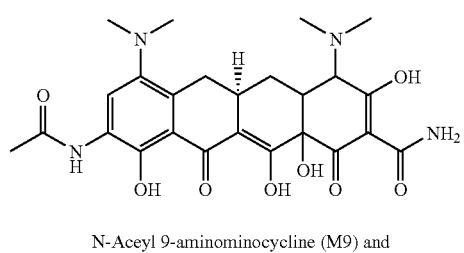

N-Acetyl 9-aminominocycline (M9) and
Epimer of N-acetyl 9-aminominocycline (M8)
Metabolites in S and U S, serum; U, urine; F, fece; * indicates the site of the radiolabel

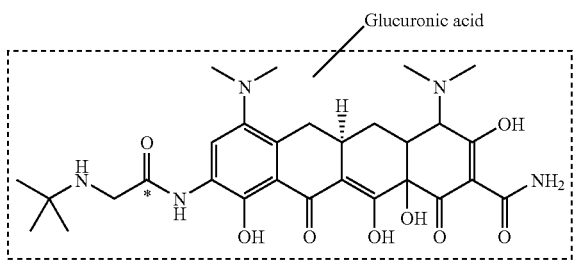

Tigecycline Glucuronide (M7) and Epimer of
Tigecycline Glucuronide (M6)
Metabolties is S, U and F

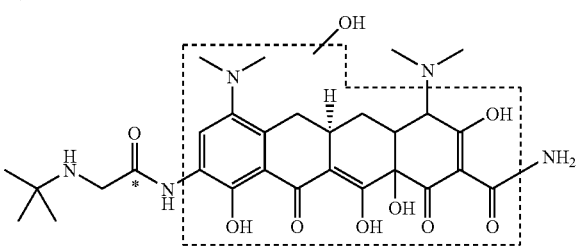

Hydroxy Tigecycline (M1, M2, M4) Trace metabolites in U

Both M6 (epimer of tigecycline glucuronide) and M7 (tigecycline glucuronide) were observed in serum and fecal sample radiochromatograms. The site of glucoronidation remains unknown. Possible structures of the metabolite and its epimer are shown below:

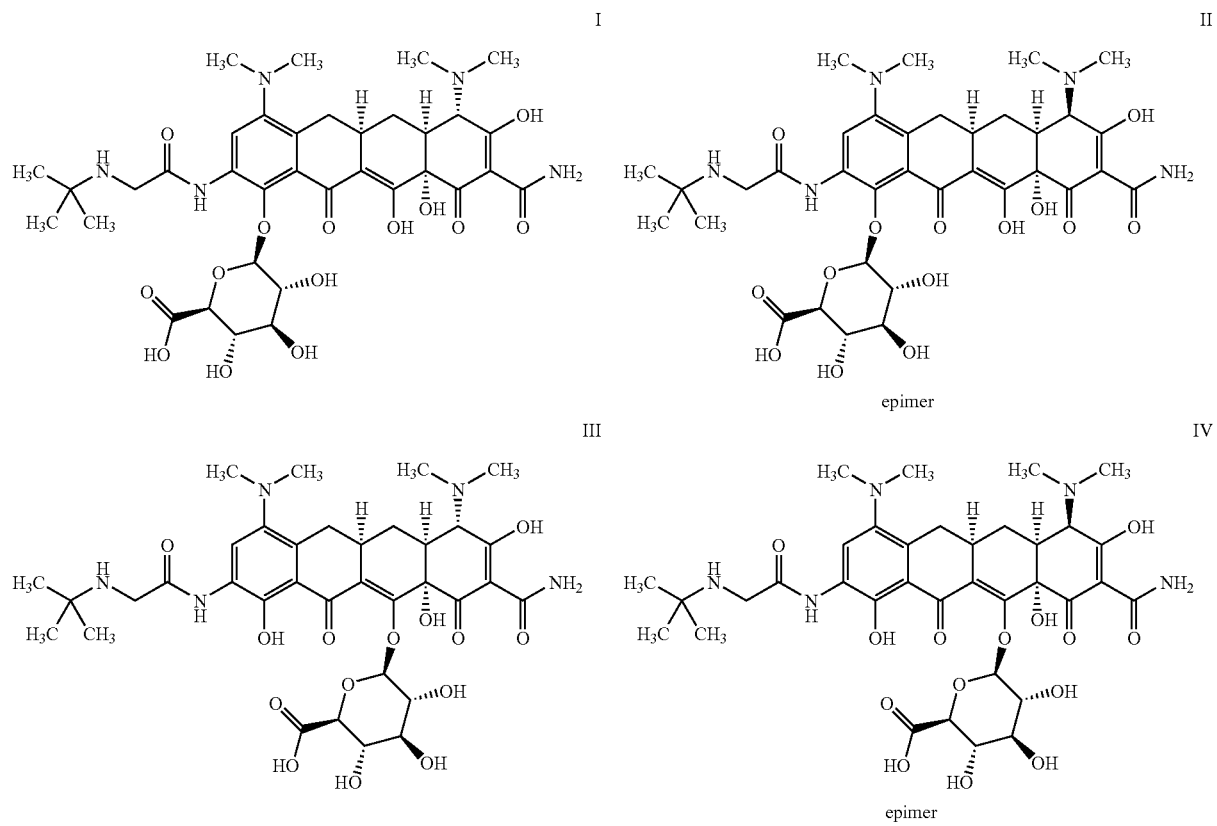

-continued

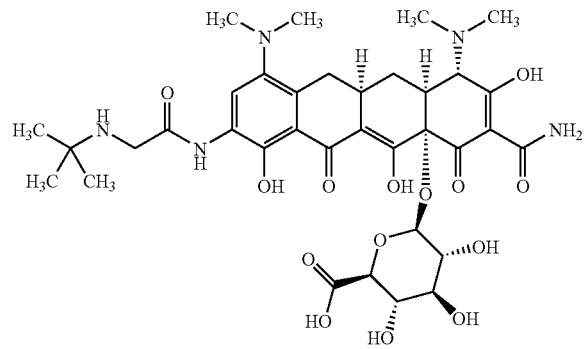

V

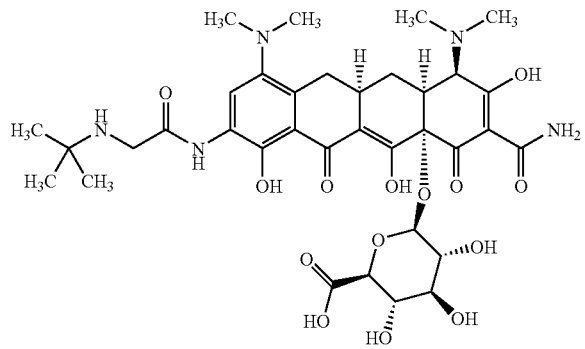

VI epimer

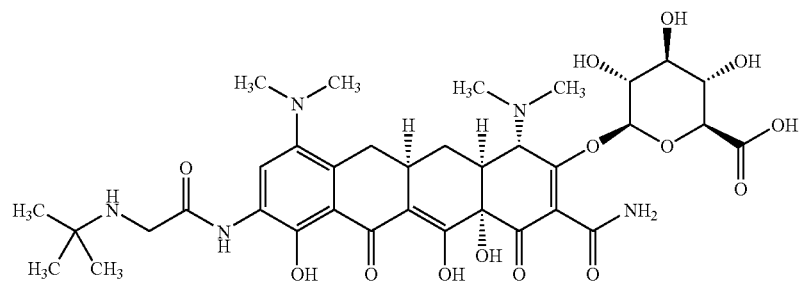

VII

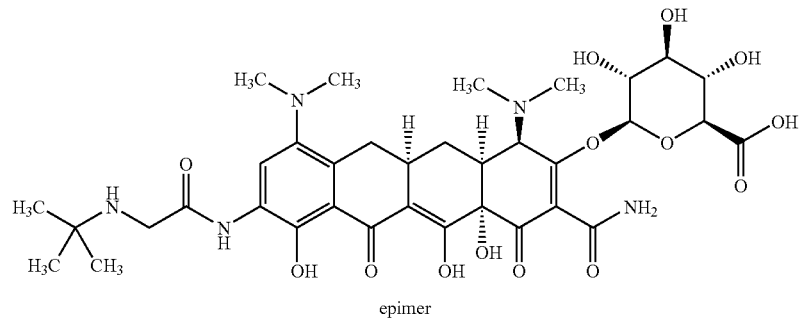

VIII epimer

M7, but not M6, was observed in radiochromatograms of urine samples. Glucuronidation of tigecycline has not previously been reported in vitro, using human liver microsomes or human hepatocytes, or in vivo in rats, dogs or humans. The previous analysis of human serum and urine was performed using unlabeled tigecycline with sample analysis by LC/MS for a preliminary assessment of tigecycline metabolism. During that study, glucuronide metabolites were not specifically investigated. Analysis of the in vivo rat and dog samples was performed using [$^{14}$C]tigecycline and no glucuronidation was observed. There are no known reports in the scientific literature that identify glucuronidation as a metabolic pathway for tetracycline antibiotics.

Metabolites M6 and M7 may be used as prodrugs of tigecycline. Once administered, β-glucuronidase enzymes may cleave M6 and M7 to release tigecycline. Administration as M6 or M7, rather than direct administration of tigecycline, may alter the absorption, distribution, metabolism, excretion, and/or side effect profile of the drug. Additionally these compounds may be of use directly as antimicrobial agents.

BRIEF DESCRIPTION OF THE DRAWINGS

FIG. 13 is the LC/MS mass spectrum for M3a;

FIG. 21A is a LC/MS/MS chromatogram from product ions of m/z 762 analysis of human urine from a subject administered tigecycline showing low intensity product ions;

FIG. 21B is a LC/MS/MS chromatogram from product ions of m/z 762 analysis of human urine from a subject administered tigecycline showing low intensity product ions;

It was determined that by treating humans with tigecycline, a glucuronide metabolite of tigecycline, along with its epimer, was produced. Both the metabolite and its epimer were found in human serum, urine, and feces and subsequently extracted and analyzed. The detailed experimental aspects of the invention are given in control examples 1-3 and examples 1-10 and describe the mass balance and metabolite profile of tigecycline dosed to six healthy male volunteers. Control examples 1-3 discuss control experiments in serum, urine, and feces used to help determine the relative stability of tigecycline in these media. Examples 1-10, on the other hand, relate to experiments performed on the six volunteers discussed above.

Referring to scheme 1, metabolites M3 (9-aminominocycline), M8 (epimer of N-acetyl-9-aminominocycline) and M9 (N-acetyl-9-aminominocycline) were also detected by LC/MS analysis of serum and urine. Since these metabolites were formed following amide hydrolysis of the t-butylaminoacetylamino side chain, they were not radiolabeled. Therefore, the concentrations of these metabolites in serum and urine could only be estimated from LC/MS data. Based on these data, M3 and M8 appeared to be minor metabolites in serum and urine, while M9 appeared to be a minor metabolite in serum but present in urine at concentrations comparable to M7. M3 has been reported in rat, dog and human urine and plasma (serum for human), but the N-acetyl metabolites (M8 and M9) have not previously been reported. Since metabolites M8 and M9 were not radiolabeled, they may have been present in samples from previous rat and dog metabolism studies, but not detected because they were not specifically investigated by LC/MS.

Figure 1:
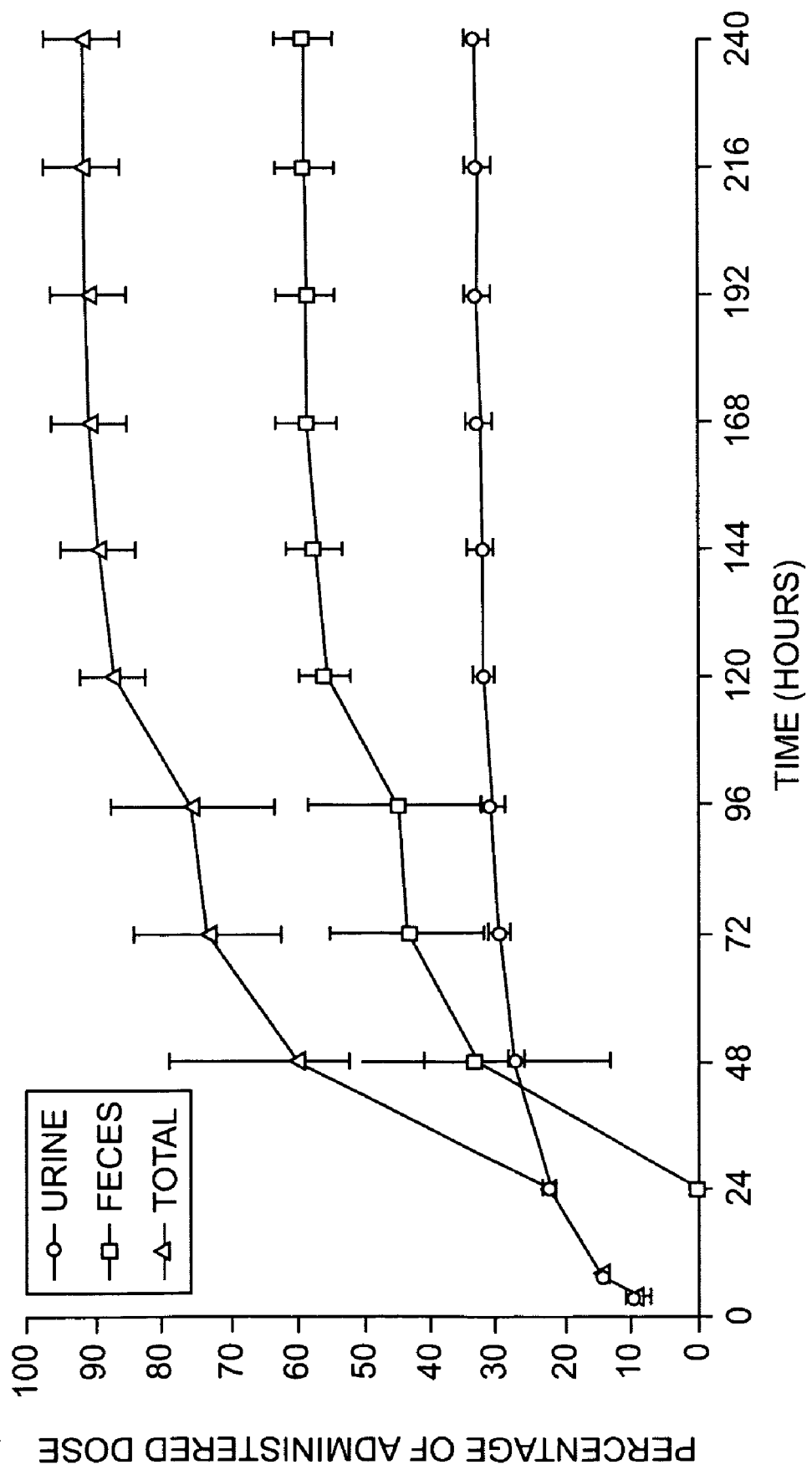
FIG. 1 is the mean (ISD) for elimination of radioactivity in urine and feces following a single intravenous 50 mg dose of [$^{14}$C]tigecycline in humans.

Mean total recovery of radioactivity in human excreta was 91.8% (±5.6, n=3), with 33.2±1.9% excreted in urine and 58.6±4.4% excreted in feces (FIG. 1). These data were consistent with data from rats and dogs where approximately 89% (including cage rinse) of a single intravenous [$^{14}$C] tigecycline dose was recovered in each species. In rats, 34% was recovered in urine and 53% in feces, while in dogs, 36% was recovered in urine and 47% in feces.

Figure 2:
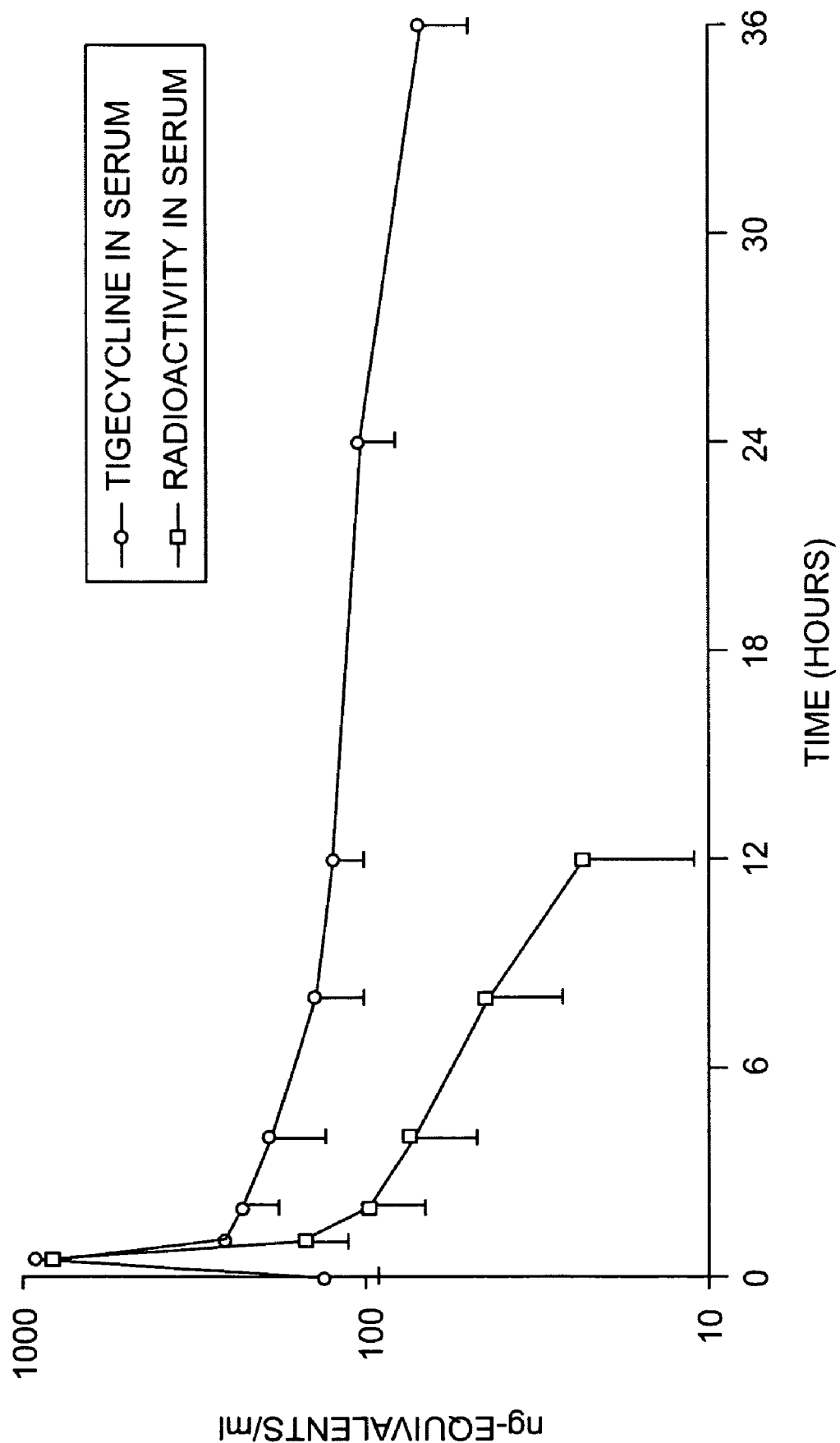
FIG. 2 is the mean (ISD) tigecycline and radioactivity concentrations in serum over time.

The radioactivity in serum declined much more rapidly than the tigecycline concentrations in serum (FIG. 2). This difference was likely caused by a significant amount of unlabeled tigecycline distributing to the tissues prior to administration of the [$^{14}$C]tigecycline, which may have limited some of the tissue uptake of [$^{14}$C]tigecycline. This "last-in, first-out" phenomenon most likely produced a much smaller volume of distribution and much higher clearance for total radioactivity as compared to tigecycline.

Approximately 50% of the [$^{14}$C]tigecycline dose was recovered in the first 48 hours (27% in urine and 24% in feces). In the urine samples analyzed, 15% of the dose was excreted as unchanged tigecycline, 2.0% as the epimer of tigecycline, 4.1% as M7 and 6.3% as M3a. In the fecal homogenate samples, 9.9% of the dose was excreted as unchanged tigecycline, 5.5% as tigecycline epimer, 5.4% as glucuronides (M6+M7) and 1.5% as M3a. The radioactivity excreted as M3a was considered to be equivalent to the amount of M3, M8 and M9 formed, which was approximately 8% of the dose. However, since metabolites M3, M8 and M9 did not contain the radiolabel, their concentrations in serum, urine and feces could not be accurately assessed.

Using LC/MS, trace amounts of hydroxy tigecycline metabolites (M1, M2 and M4) were detected in urine, but were not detected by radiochromatography. These hydroxy tigecycline metabolites have previously been reported as trace metabolites in rat and dog, plasma and urine, and in human serum and urine. However, the previously reported, estimated concentrations of these metabolites in human serum and urine are below the limit of detection for radiochromatography in the current study. An N-desmethyl metabolite of tigecycline was reported as a trace metabolite in rat plasma and urine, and in a single human urine sample from a previous study. This metabolite was not detected in any of the samples analyzed in the current study.

The current study assessed only the disposition of the [$^{14}$C]-labeled tigecycline dose, and did not account for any tigecycline-related products remaining from the unlabeled doses. Therefore, the estimated concentrations of the tigecycline-related products reported here were expected to underestimate the actual concentrations of these components in serum, urine and feces. In fact, the concentration of total tigecycline (radiolabeled and non-labeled) in serum and urine samples from the current study were consistently greater (generally 10 to 300% greater) than the concentrations calculated for those same samples using the radioactivity concentration and the specific activity of the [$^{14}$C]tigecycline dose. This was not unexpected based on the dosing schedule (multiple unlabeled doses, followed by a single [$^{14}$C]-labeled dose) used in the current study and the long half-life reported for tigecycline.

Accordingly, after multiple intravenous tigecycline administrations followed by a single [$^{14}$C]-labeled tigecycline dose to healthy, male volunteers, the predominant radiolabeled component in serum, urine and feces was unchanged tigecycline. The major metabolic pathways for tigecycline were glucuronidation and amide hydrolysis followed by N-acetylation. A degradation product, the epimer of tigecycline, was also detected in each sample.

The concentration of tigecycline-related components in serum, urine and feces was calculated based on the total radioactivity concentrations reported elsewhere. These concentrations were converted to ng-tigecycline equivalents using the specific activity of the dose (1.00 µCi/mg). Using this value, the concentrations of the specific components were then estimated based on the distribution of radioactivity in the radiochromatograms. These concentrations reflect only the disposition of the [$^{14}$C]-labeled tigecycline dose, and do not account for any tigecycline-related products remaining from the unlabeled doses.

Figure 3A:
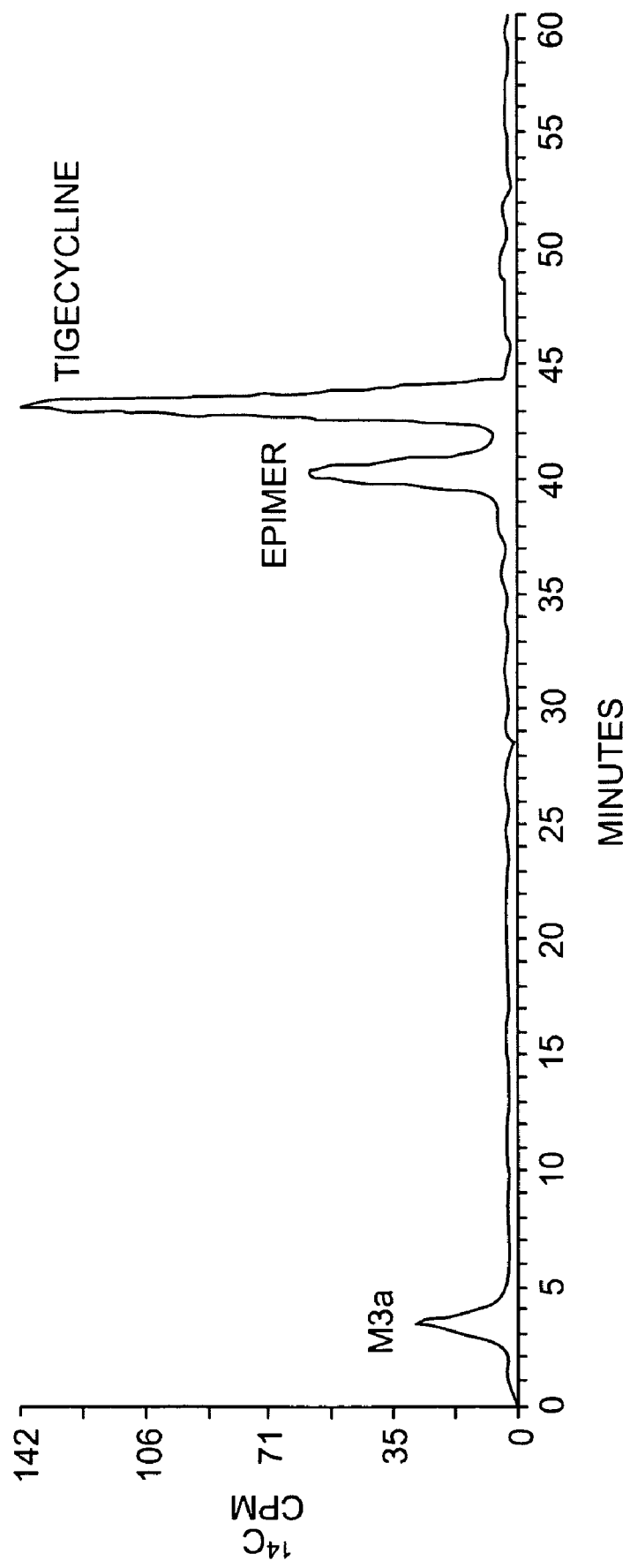
FIG. 3A shows an HPLC radiochromatogram of extracted human serum from subject 1 at 1 hour following the [$^{14}$C] tigecycline dose.
Figure 3B:
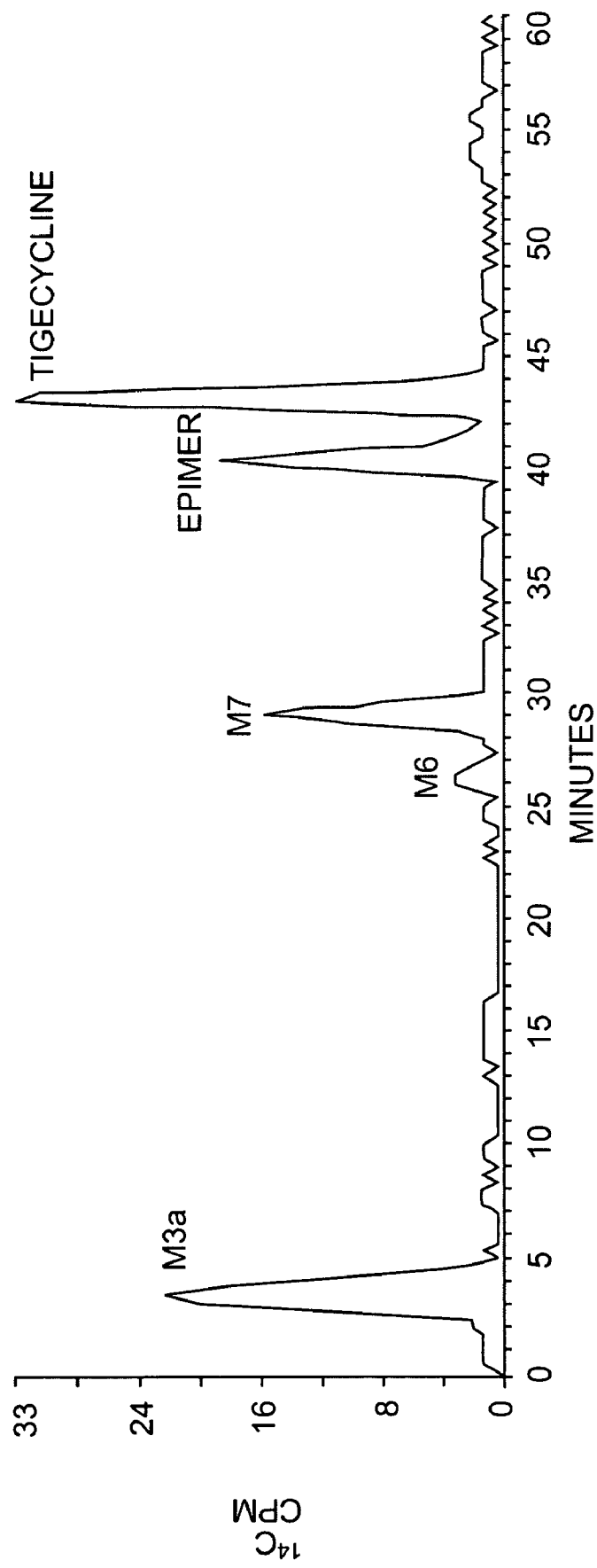
FIG. 3B shows an HPLC radiochromatogram of extracted human serum from subject 1 at 8 hours following the [$^{14}$C] tigecycline dose.

Representative HPLC radiochromatograms of serum extracts from subject 1 at 1 and 8 hr post-dose are shown in FIGS. 3A and 3B. The metabolite profiles for the serum extracts were similar for the different subjects and at the different time points. Table 1 shows the relative distribution of radioactivity in the serum extracts and the estimated concentration of each [$^{14}$C]tigecycline-related component in serum.

TABLE 1

Relative Distribution of Radioactivity and Estimated Concentrations in Extracted Serum Samples from Healthy Male Subjects Following Intravenous Administration of a Single 50 mg Dose of [$^{14}$C]-Labeled Tigecycline

| | | Relative Distribution (%)[a] and Estimated Concentrations (ng-Tigecycline Equivalents/mL)[b,c] | | | | |
|---|---|---|---|---|---|---|
| Time (hr) | Subject | M3a | M6 | M7 | Tigecycline Epimer[d] | Tigecycline |
| 1 | 1 | 5.2 (11) | ND | ND | 25.5 (54) | 66.3 (140) |
| | 4 | 10.9 (16) | ND | 1.1 (1.6) | 29.3 (42) | 55.7 (80) |
| | 5 | 6.8 (9.0) | ND | ND | 21.8 (29) | 70.2 (92) |
| | 6 | 13.5 (20) | ND | ND | 27.7 (40) | 54.2 (79) |
| | 7 | 10.1 (17) | ND | ND | 20.4 (35) | 68.1 (120) |
| | 8 | 12.4 (13) | 1.2 (1.3) | 1.8 (1.9) | 22.1 (24) | 61.7 (66) |
| | Average ± SD | 9.8 ± 3.2 | 0.2 ± 0.5 | 0.5 ± 0.8 | 24.5 ± 3.6 | 62.7 ± 6.6 |
| 4 | 1 | 17.0 (22) | ND | 3.6 (4.6) | 24.0 (31) | 51.0 (65) |
| | 4 | 17.0 (12) | 3.8 (2.7) | 11.6 (8.1) | 21.6 (15) | 42.3 (30) |
| | 5 | 10.9 (5.6) | ND | 5.9 (3.0) | 22.1 (11) | 60.4 (31) |
| | 6 | 24.7 (15) | 3.5 (2.1) | 7.7 (4.5) | 19.2 (11) | 43.2 (26) |
| | 7 | 14.9 (11) | 2.8 (2.0) | 6.9 (4.9) | 24.7 (18) | 47.5 (34) |
| | 8 | 15.9 (11) | 7.7 (5.3) | 18.3 (13) | 11.4 (7.9) | 45.2 (31) |
| | Average ± SD | 16.7 ± 4.5 | 3.0 ± 2.9 | 9.0 ± 5.3 | 20.5 ± 4.9 | 48.3 ± 6.7 |

TABLE 1-continued

Relative Distribution of Radioactivity and Estimated Concentrations in Extracted Serum Samples from Healthy Male Subjects Following Intravenous Administration of a Single 50 mg Dose of [$^{14}$C]-Labeled Tigecycline

| Time (hr) | Subject | Relative Distribution (%)[a] and Estimated Concentrations (ng-Tigecycline Equivalents/mL)[b,c] | | | | |
|---|---|---|---|---|---|---|
| | | M3a | M6 | M7 | Tigecycline Epimer[d] | Tigecycline |
| 8 | 1 | 12.3 (9.6) | 3.0 (2.3) | 14.1 (11) | 21.7 (17) | 45.5 (36) |
| | 4 | 23.9 (11) | 6.5 (2.9) | 12.4 (5.6) | 18.3 (8.2) | 37.5 (17) |
| | 5 | 16.7 (5.3) | ND | 5.4 (1.7) | 21.0 (6.7) | 57.0 (18) |
| | 6 | 27.5 (8.8) | 2.6 (1.0) | 13.0 (4.2) | 15.9 (5.1) | 41.0 (13) |
| | 7 | 12.7 (4.2) | ND | 3.4 (1.1) | 22.2 (7.3) | 59.1 (20) |
| | 8 | 21.2 (10) | 8.0 (3.8) | 23.2 (11) | 10.7 (5.1) | 37.0 (18) |
| | Average ± SD | 19.1 ± 6.2 | 3.4 ± 3.3 | 11.9 ± 7.1 | 18.3 ± 4.4 | 46.2 ± 9.7 |

[a]Relative distribution was determined by area integration of peaks in the HPLC radiochromatograms from duplicate samples.
[b]In parentheses, the relative concentration as ng-tigecycline equivalents/mL was estimated by multiplying the serum radioactivity concentration (as ng-tigecycline equivalents/mL) with the percent distribution from the HPLC radiochromatograms.
[c]The limit of detection was 1 ng equivalents/mL.
[d]Much of the tigecycline epimer observed in the serum extracts was likely a result of the extraction process.
ND. Indicates metabolite was not detected and assigned a value of zero.

Concentrations were estimated based on the specific activity of the dose solution, the serum radioactivity concentrations reported elsewhere, and the relative distribution of radioactivity in each sample. For all subjects at all time points, tigecycline was the predominant drug-related component detected, accounting for 63% of the radioactivity at 1 hr and decreasing to 48 and 46% at 4 and 8 hr, respectively (table 1).

Figure 4:
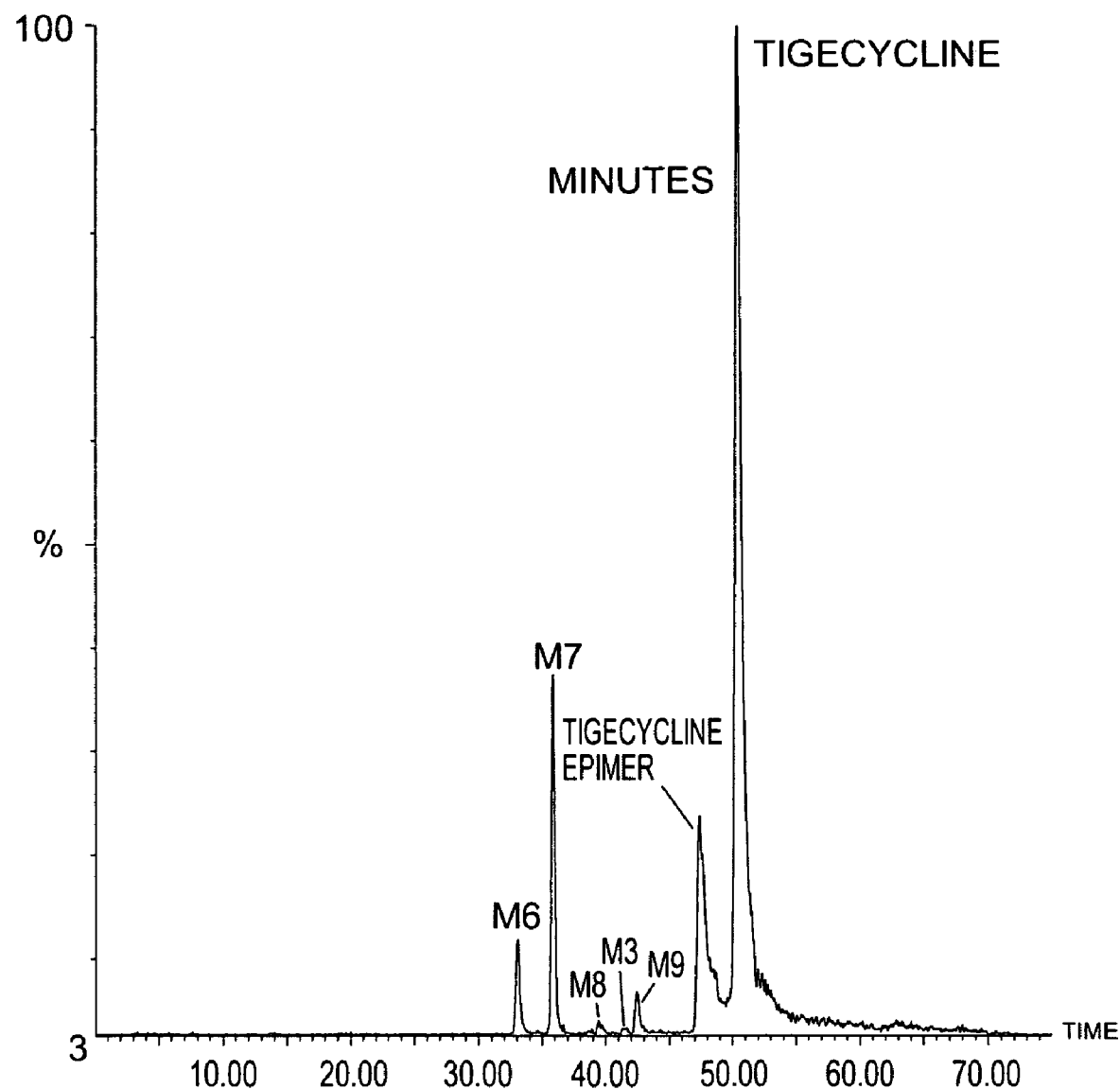
FIG. 4 is a combined LC/SRM chromatograms of extracted human serum from subject 1 at 8 hours following the [$^{14}$C] tigecycline dose.

The epimer of tigecycline was the next most abundant drug-related component present, representing approximately 20% of the radioactivity. However, a large proportion of the tigecycline epimer in the serum extracts may have been formed during the extraction process. After correcting for the epimer formed during the extraction, the amount of epimer in the serum samples decreases to between 5 and 8%, and the amount of tigecycline increases to 59 to 80%. A tigecycline glucuronide (M7) represented less than 1% of the radioactivity at 1 hr, but increased to 9 and 12% at 4 and 8 hr, respectively. A glucuronide of the tigecycline epimer (M6) was detected in approximately half the serum samples analyzed and accounted for less than 4% of the radioactivity. An early eluting chromatographic peak (M3a, t-butylaminoacetic acid), retention time 4-7 minutes, was detected in all serum samples and accounted for between 10 and 20% of the radioactivity. FIG. 4 shows the combined LC/SRM chromatograms, collected using LC/MS/MS in the selected reaction monitoring (SRM) mode, of the tigecycline-related compounds detected in serum, including 9-aminominocycline (M3), epimer of N-acetyl-9-aminominocycline (M8) and N-acetyl-9-aminominocycline (M9). These metabolites were not radiolabeled because the t-butylaminoacetylamino side chain was cleaved and could not be quantified using radioactivity flow detection. Based on LC/MS analysis, these were minor metabolites in serum.

Figure 5A:
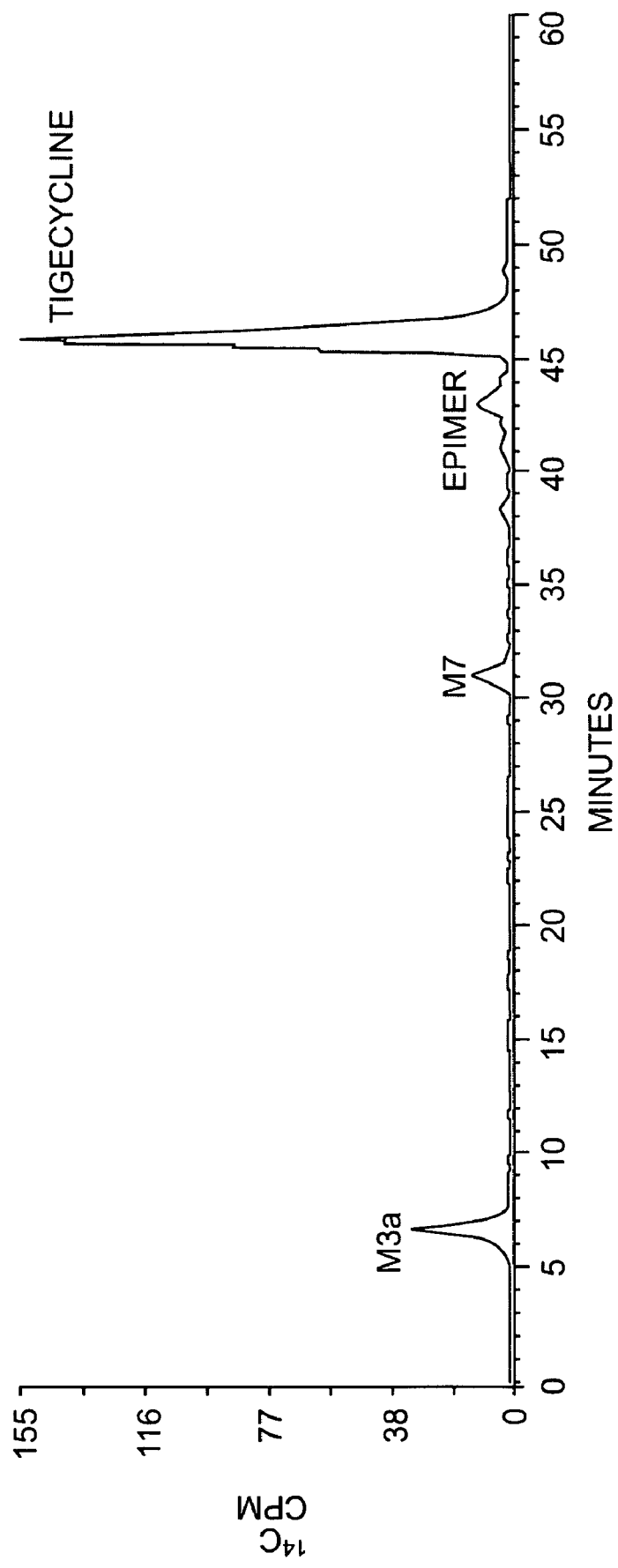
FIG. 5A is an HPLC radiochromatogram of human urine from subject 4 collected 0-4 hours following the [$^{14}$C]tigecycline dose.
Figure 5B:
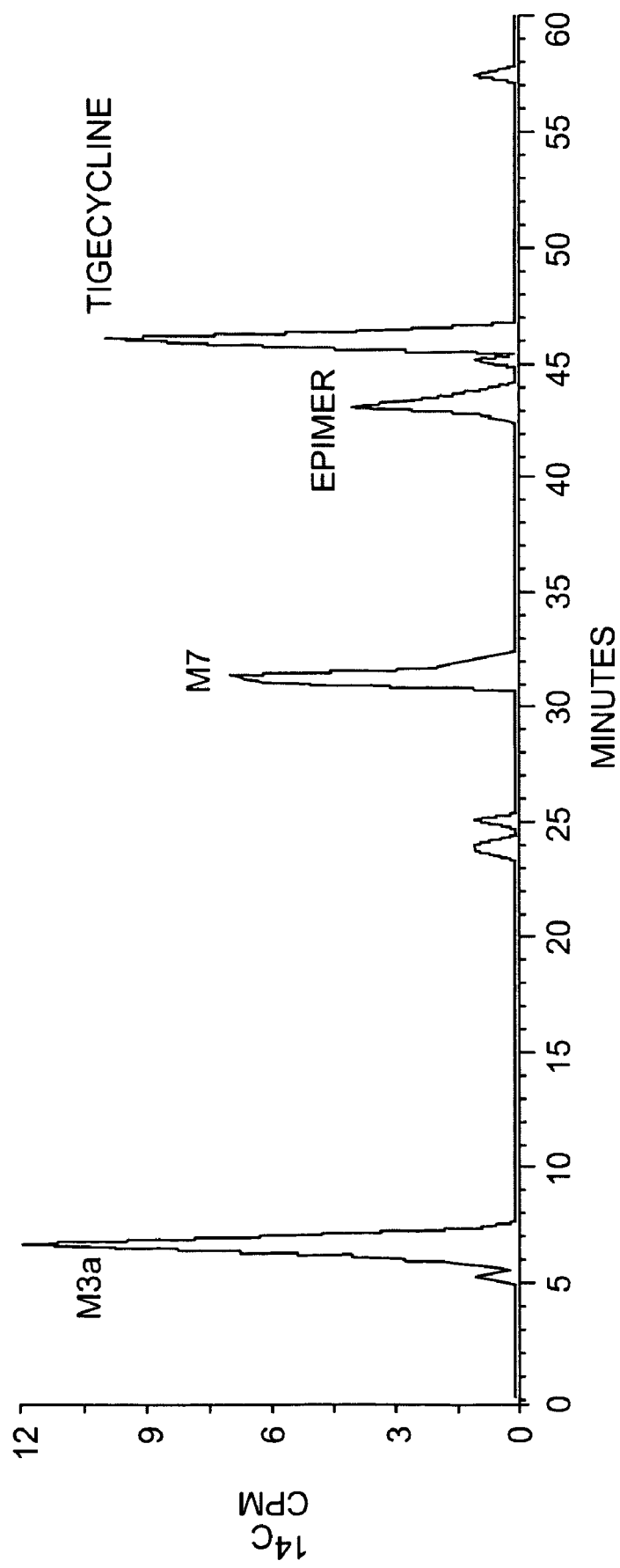
FIG. 5B is an HPLC radiochromatogram of human urine from subject 4 collected 24-48 hours following the [$^{14}$C] tigecycline dose.
Figure 5C:
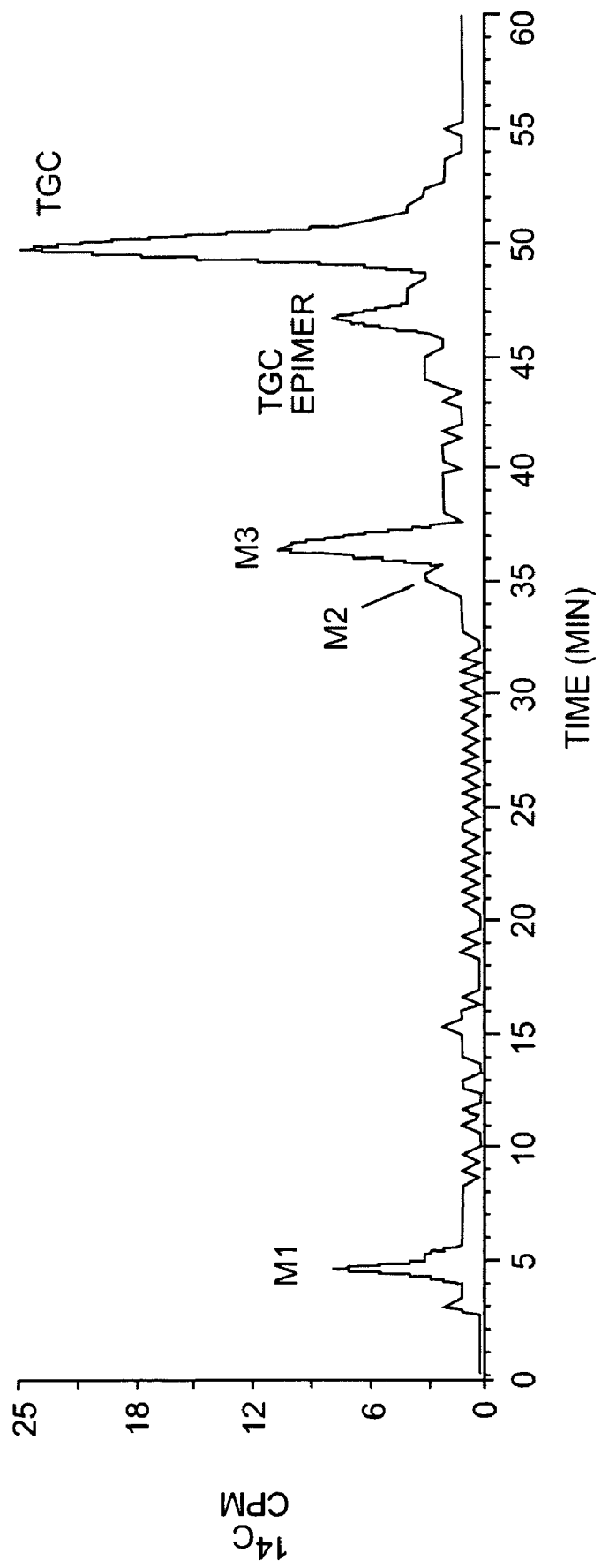
FIG. 5C is an HPLC radiochromatogram of human feces from subject 4 collected 24-48 hrs following the [$^{14}$C]tigecycline dose.

Approximately 27% of the radioactive dose was excreted in urine within 48 hours of the [$^{14}$C]tigecycline dose. Representative HPLC radiochromatograms of urine from subject 4, collected 0-4 and 24-48 hr post-dose are shown in FIGS. 5A-5C. The metabolite profiles for urine were similar between subjects and at the different time points. The relative distribution of radioactivity in the urine samples and the estimated concentration of each [$^{14}$C]tigecycline-related component in urine are provided in Table 2.

TABLE 2

Relative Distribution of Radioactivity and Estimated Concentrations in Urine Samples from Healthy Male Subjects Following Intravenous Administration of a Single 50 mg Dose of [$^{14}$C]-Labeled Tigecycline

| Time (hr) | Subject | Relative Distribution (%)[a] and Estimated Concentrations (μg-Tigecycline Equivalents/Collection)[b,c] | | | |
|---|---|---|---|---|---|
| | | M3a | M7 | Tigecycline Epimer | Tigecycline |
| 0-4 | 1 | 16.6 (803) | 3.4 (164) | 3.0 (144) | 77.0 (3719) |
| | 4 | 11.4 (484) | 4.7 (198) | 5.8 (246) | 78.2 (3322) |
| | 5 | 11.6 (394) | ND | 2.8 (95) | 88.4 (3006) |
| | 6 | 17.5 (701) | 3.6 (145) | 4.4 (177) | 74.4 (2977) |
| | 7 | 18.9 (950) | 3.2 (159) | 3.9 (195) | 74.1 (3717) |
| | 8 | 12.6 (505) | 7.3 (291) | 9.6 (386) | 70.5 (2819) |
| | Average ± SD | 14.8 ± 3.3 | 3.7 ± 2.4 | 4.9 ± 2.6 | 77.1 ± 6.2 |
| 4-8 | 1 | 24.2 (572) | 21.0 (496) | 5.4 (127) | 49.4 (1165) |
| | 4 | 28.0 (445) | 24.2 (385) | 5.4 (85) | 42.5 (675) |
| | 5 | 16.5 (511) | 11.3 (350) | 6.6 (202) | 65.6 (2028) |
| | 6 | 32.7 (723) | 19.1 (421) | 5.5 (120) | 42.8 (945) |
| | 7 | 24.3 (488) | 14.8 (298) | 7.2 (145) | 53.7 (1079) |
| | 8 | 25.9 (521) | 33.6 (676) | 6.1 (122) | 34.4 (691) |
| | Average ± SD | 25.3 ± 5.3 | 20.7 ± 7.8 | 6.0 ± 0.8 | 48.0 ± 10.9 |
| 8-24 | 1 | 27.2 (1218) | 22.6 (1011) | 6.0 (268) | 44.3 (1983) |
| | 4 | 28.9 (926) | 28.5 (916) | 7.0 (224) | 35.6 (1143) |
| | 5 | 18.6 (752) | 16.2 (653) | 11.2 (451) | 54.1 (2185) |
| | 6 | 42.0 (1562) | 24.7 (917) | 5.4 (202) | 27.9 (1039) |
| | 7 | 27.3 (902) | 16.9 (556) | 10.2 (335) | 45.7 (1507) |
| | 8 | 32.5 (1223) | 33.1 (1246) | 5.6 (211) | 28.9 (1090) |
| | Average ± SD | 29.4 ± 7.7 | 23.6 ± 6.6 | 7.5 ± 2.5 | 39.4 ± 10.3 |
| 24-48 | 1 | 38.5 (616) | 15.6 (250) | 13.8 (220) | 32.1 (513) |
| | 4 | 39.9 (865) | 23.8 (515) | 9.8 (212) | 26.6 (577) |
| | 5 | 23.3 (560) | 9.1 (219) | 15.0 (360) | 52.5 (1261) |
| | 6[d] | 46.4 (204) | 19.4 (86) | 5.4 (24) | 27.9 (123) |
| | 7 | 35.3 (867) | 13.7 (336) | 12.2 (301) | 38.9 (956) |

TABLE 2-continued

Relative Distribution of Radioactivity and Estimated Concentrations in Urine Samples from Healthy Male Subjects Following Intravenous Administration of a Single 50 mg Dose of [$^{14}$C]-Labeled Tigecycline

| Time (hr) | Sub-ject | Relative Distribution (%)[a] and Estimated Concentrations (μg-Tigecycline Equivalents/Collection)[b,c] | | | |
|---|---|---|---|---|---|
| | | M3a | M7 | Tigecycline Epimer | Tigecycline |
| 8 | | 39.7 (838) | 26.7 (564) | 9.4 (199) | 24.2 (510) |
| Average ± SD | | 37.2 ± 7.7 | 18.1 ± 6.6 | 10.9 ± 3.5 | 33.7 ± 10.6 |

[a]Relative distribution was determined by area integration of peaks in the HPLC radiochromatograms from duplicate samples.
[b]In parentheses, the relative concentration as μg-tigecycline equivalents/collection was estimated by multiplying the total urinary radioactivity (as μg-tigecycline equivalents) with the percent distribution from the HPLC radiochromatograms.
[c]The limit of detection was 90 ng equivalents/mL.
[d]For subject 6, the 24–48 hr collection was a partial collection.
ND. Indicates metabolite was not detected and assigned a value of zero.

Concentrations were estimated based on the specific activity of the dose solution, the urinary radioactivity concentrations reported elsewhere, and the relative distribution of radioactivity in each sample. The percent of the [$^{14}$C]tigecycline dose excreted in urine and feces as each of the [$^{14}$C] tigecycline-related components is shown in table 3.

TABLE 3

Percent of the [$^{14}$C]Tigecycline Dose Excreted as Tigecycline-Related Components

| Matrix and Collection Time (hours) | Percentage of Dose (mean ± standard deviation) | | | | |
|---|---|---|---|---|---|
| | M3a | M6 | M7 | Tigecyline Epimer | Tigecycline |
| Urine | | | | | |
| 0–4 | 1.4 ± 0.5 | ND | 0.4 ± 0.2 | 0.5 ± 0.2 | 7.1 ± 0.9 |
| 4–8 | 1.2 ± 0.2 | ND | 1.0 ± 0.3 | 0.3 ± 0.1 | 2.4 ± 1.1 |
| 8–24 | 2.4 ± 0.6 | ND | 1.9 ± 0.5 | 0.6 ± 0.2 | 3.3 ± 1.1 |
| 24–48[a] | 1.6 ± 0.3 | ND | 0.8 ± 0.4 | 0.6 ± 0.2 | 1.7 ± 0.7 |
| Total Urine | 6.3 ± 0.9 | ND | 4.1 ± 1.4 | 2.0 ± 0.3 | 14.8 ± 2.9 |
| Feces (0–48) | 1.5 ± 1.0 | 1.4 ± 1.0 | 4.0 ± 3.2 | 5.5 ± 4.7[b] | 9.9 ± 7.9 |
| Total (0–48) | 7.8 ± 0.7 | 1.4 ± 1.0 | 8.1 ± 4.2 | 7.5 ± 4.9 | 24.7 ± 8.7 |

[a]For the 24–48 hour urine, the total urine, fecal samples and the total n = 5, because of incomplete urine and fecal collections from subject #6.
[b]Much of the tigecycline epimer observed in the fecal homogenate extracts was likely a result of the extraction process.
ND. Indicates metabolite was not detected.

Figure 6:
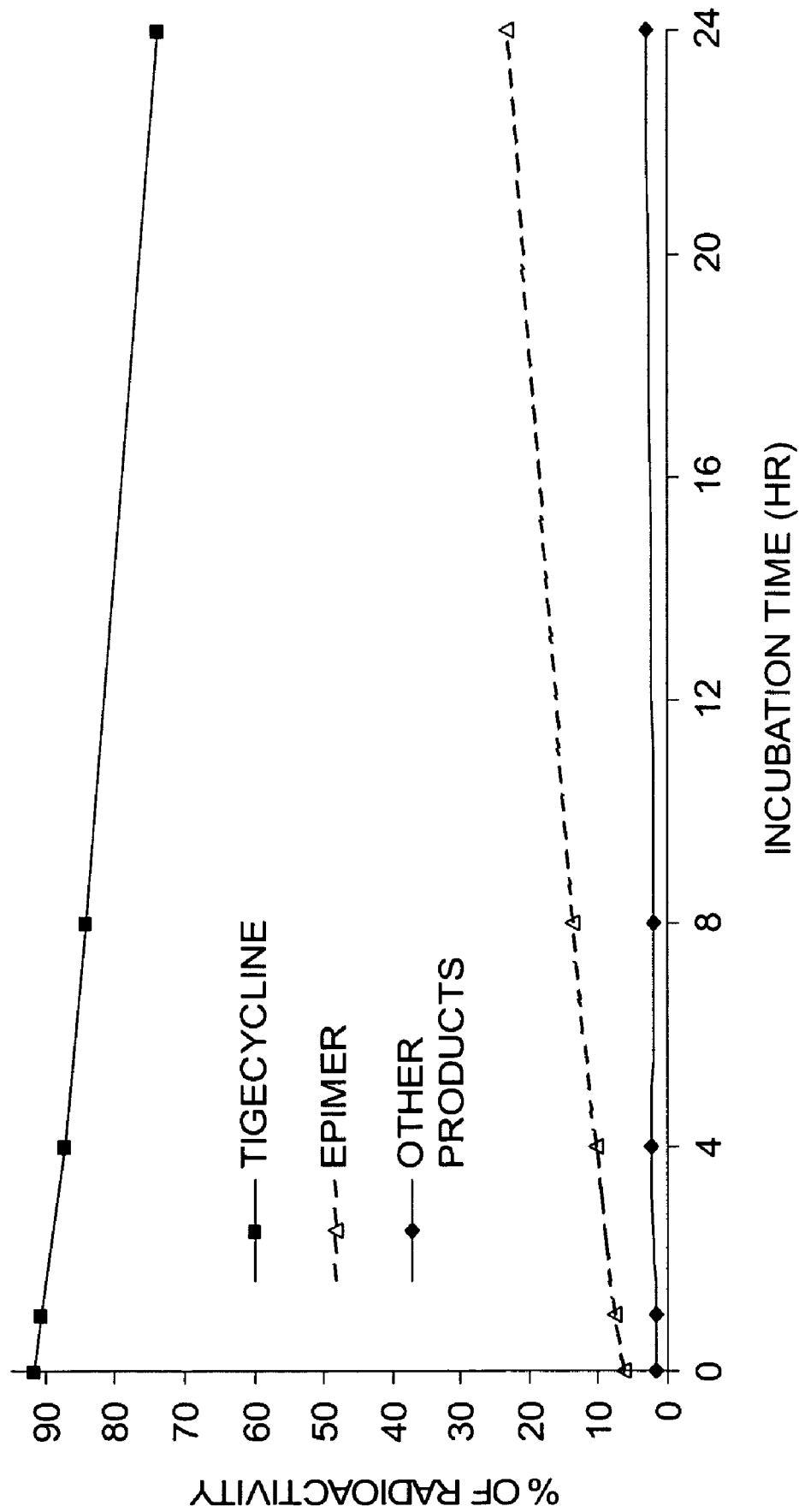
FIG. 6 is the stability of [$^{14}$C]tigecycline incubated at 37° C. in human urine.

For all subjects, tigecycline was the predominant drug-related component excreted in urine table 2, with approximately 15% of the dose being excreted as unchanged drug in urine within the first 48 hours (table 3). The amount of urinary radioactivity identified as the epimer of tigecycline increased from 5% of the radioactivity in the 0-4 hour collection to 11% in the 24-48 hour collection. Some of the epimer may have formed in the bladder, as stability analysis demonstrated that tigecycline degraded to the epimer, when incubated in urine at 37° C. (FIG. 6). A total of 2% of the radioactive dose was excreted in urine as the epimer of tigecycline within the first 48 hours. Metabolite M7 was only a minor component in the 0-4 hr collection, but represented approximately 20% of the urinary radioactivity in the samples collected from 4-8, 8-24 and 24-48 hr. M3a represented between 15 and 37% of the radioactivity in urine and increased relative to tigecycline over time.

Figure 7:
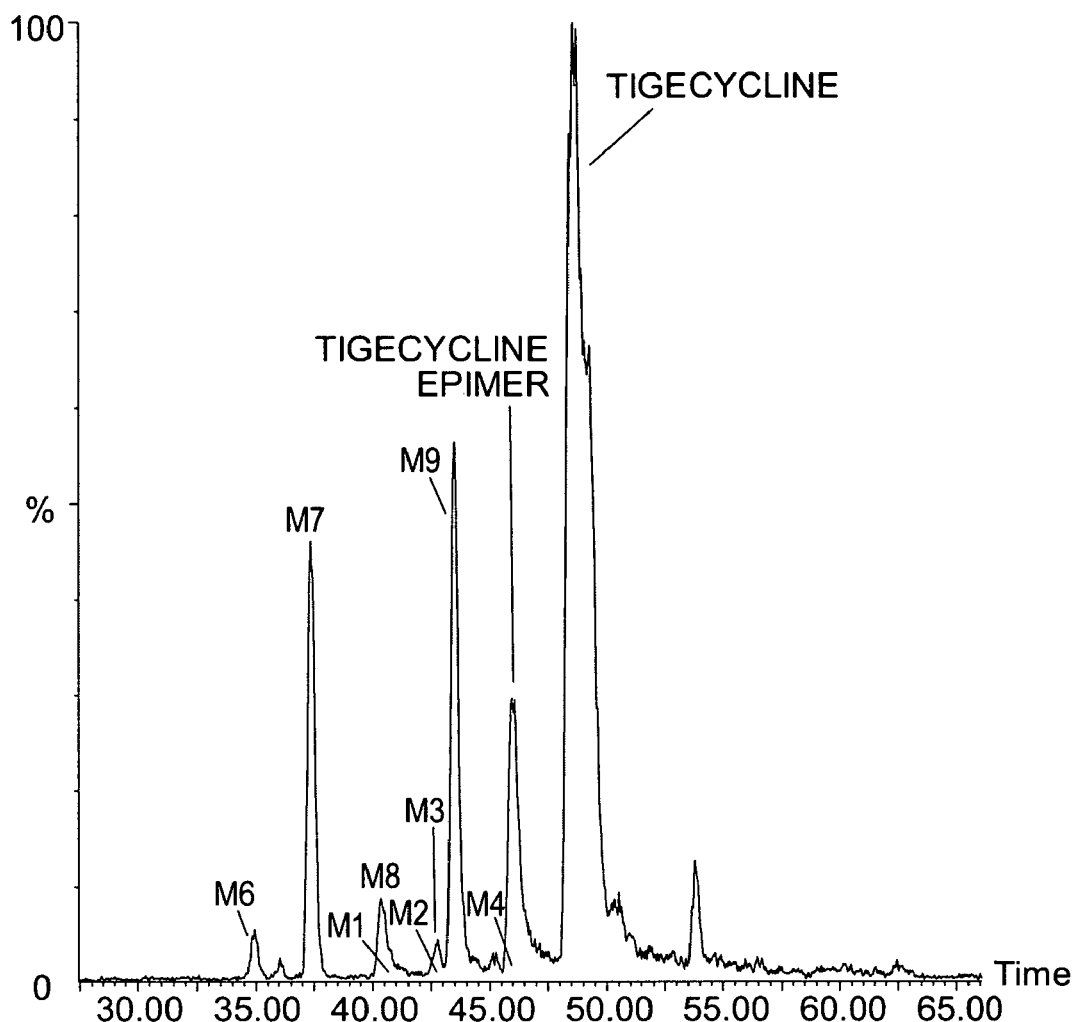
FIG. 7 is the combined mass chromatograms of human urine from subject 8 collected 0-4 hours following the [$^{14}$C] tigecycline dose.

The amounts of metabolites M3a and M7 excreted in urine within 48 hours accounted for 6 and 4% of the radioactive dose, respectively. FIG. 7 shows combined mass chromatograms of the tigecycline-related compounds detected in urine. The radiolabeled hydroxy tigecycline metabolites (M1, M2 and M4), as well as M6, were considered trace urinary metabolites that accounted for less than 1% of the radioactivity in urine. Metabolites M3, M8 and M9 were not radiolabeled, so there relative amounts could only be estimated based on LC/MS analysis. Based on LC/MS data, M3 and M8 were minor metabolites, while M9 was present at concentrations similar to M7.

Figure 8:
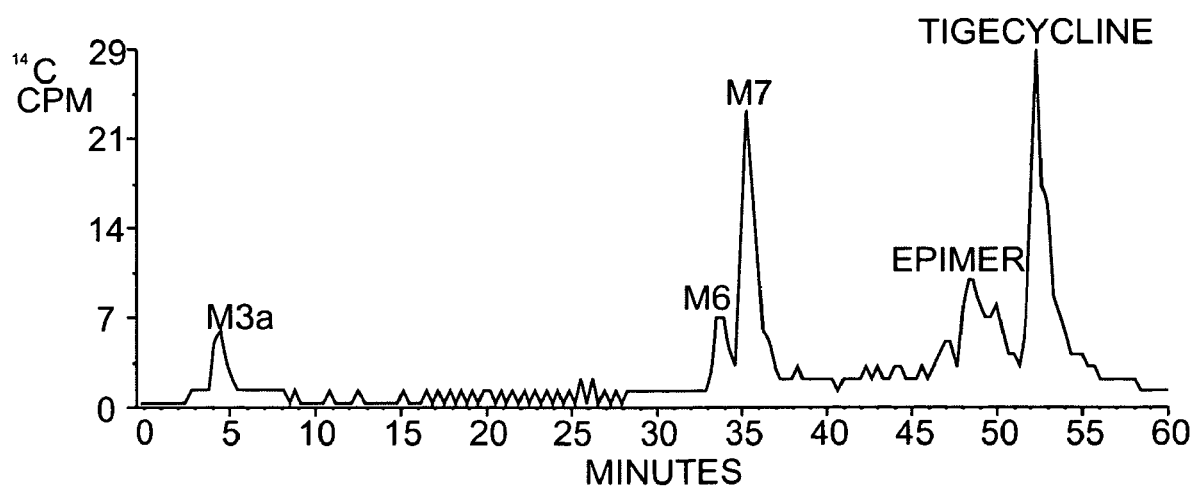
FIG. 8 is the HPLC radiochromatogram of extracted human feces from subject 8 collected at 34.2 hours following the [$^{14}$C]tigecycline dose.

Within 48 hours of the radioactive dose, approximately 24% of the radioactivity was recovered in feces. A representative HPLC radiochromatogram of a fecal extract from subject 8, collected approximately 34 hr post-dose is shown in FIG. 8. The metabolite profiles for feces were similar between subjects and for all fecal samples collected. The relative distribution of radioactivity in the fecal extracts and the estimated concentration of each [$^{14}$C]tigecycline-related component in feces is shown in table 3.

TABLE 3

Relative Distribution of Radioactivity and Estimated Concentrations in Extracted Fecal Homogenate Samples from Healthy Male Subjects Following Intravenous Administration of a Single 50 mg Dose of [$^{14}$C]-Labeled Tigecycline

| Subject and Time of Collection (hrs post-dose) | Relative Distribution (%)[a] and Estimated Concentrations (mg-Tigecycline Equivalents/Collection)[b,c] | | | | | |
|---|---|---|---|---|---|---|
| | M3a | M6 | M7 | Tigecycline Epimer[d] | Tigecycline | Other[e] |
| Subject 1 - 41.8 hrs | 6.7 (0.56) | 8.9 (0.75) | 21.3 (1.8) | 21.5 (1.8) | 28.1 (2.4) | 13.7 (1.2) |

TABLE 3-continued

Relative Distribution of Radioactivity and Estimated Concentrations in
Extracted Fecal Homogenate Samples from Healthy Male Subjects Following
Intravenous Administration of a Single 50 mg Dose of [$^{14}$C]-Labeled Tigecycline

| Subject and Time of Collection (hrs post-dose) | Relative Distribution (%)[a] and Estimated Concentrations (mg-Tigecycline Equivalents/Collection)[b,c] | | | | | |
|---|---|---|---|---|---|---|
| | M3a | M6 | M7 | Tigecycline Epimer[d] | Tigecycline | Other[e] |
| Subject 4 - 24.2 hrs | 13.9 (0.30) | 5.8 (0.13) | 23.5 (0.51) | 11.9 (0.26) | 44.9 (0.97) | ND |
| Subject 5 - 25.2 hrs | 7.5 (0.81) | 4.1 (0.44) | 10.4 (1.1) | 21.8 (2.4) | 39.9 (4.3) | 16.3 (1.8) |
| Subject 5 - 30.0 hrs | 5.9 (0.55) | 5.6 (0.52) | 13.3 (1.2) | 26.7 (2.5) | 48.3 (4.5) | ND |
| Subject 7 - 32.0 hrs | 4.2 (0.20) | 3.0 (0.14) | 10.4 (0.49) | 22.3 (1.0) | 50.7 (2.4) | 9.4 (0.44) |
| Subject 8 - 24.6 hrs | 6.2 (0.25) | ND | 9.8 (0.40) | 26.3 (1.1) | 47.7 (2.0) | 10.0 (0.41) |
| Subject 8 - 29.8 hrs | 4.1 (0.49) | 6.8 (0.82) | 21.6 (2.6) | 21.4 (2.6) | 39.1 (4.7) | 7.0 (0.84) |
| Subject 8 - 34.2 hrs | 3.9 (0.17) | 7.5 (0.32) | 26.3 (1.1) | 23.8 (1.0) | 32.8 (1.4) | 5.7 (0.25) |

[a]Relative distribution was determined by area integration of peaks in the HPLC radiochromatograms from duplicate samples.
[b]In parentheses, the relative concentration as mg-tigecycline equivalents/collection was estimated by multiplying the total fecal radioactivity (as mg-tigecycline equivalents) with the percent distribution from the HPLC radiochromatograms.
[c]The limit of detection was 0.15 μg equivalents/g of homogenate.
[d]Much of the tigecycline epimer observed in the fecal homogenate extracts was likely a result of the extraction process.
[e]Other chromatographic peaks had retention times of between 41 and 46 minutes.
ND. Indicates metabolite was not detected.
No fecal samples were received from subject 6.

Concentrations were estimated based on the specific activity of the dose solution, the fecal radioactivity concentrations reported elsewhere, and the relative distribution of radioactivity in each sample. For all fecal samples, tigecycline was the predominant drug-related component, accounting for 28-51% of the fecal radioactivity (table 3). This corresponded to approximately 10% of the radioactive dose excreted as unchanged drug in feces within 48 hours (table 2). The epimer of tigecycline was a major drug-related component in fecal extracts and represented 12-27% of the fecal radioactivity and 5.5% of the radioactive dose. As with serum, a significant amount of the tigecycline epimer was formed during the extraction process. Correcting for the epimer formed during the extraction process, the amount of epimer decreases to less than 12% in all of the samples, while the amount of tigecycline increases to between 39 and 66%. Metabolite M7 represented 10-26% of the radioactivity in feces, while M6 represented up to 9%. The glucuronide metabolites in the 0-48 hour fecal samples represented approximately 5.5% of the radioactive dose. M3a represented between 4 and 14% of the radioactivity in feces and less than 2% of the dose was excreted as M3a in feces. Additional peaks, representing up to 16% of the fecal radioactivity and approximately 2% of the dose, were observed in some fecal samples. LC/MS analysis of the fecal samples did not detect any additional metabolites.

A summary of the tigecycline related compounds observed in serum, urine and feces is presented in (table 4).

TABLE 4

Tigecycline Related Compounds Observed in Human Serum, Urine
and Feces Following Intravenous Administration
of a Single 50 mg Dose of [$^{14}$C]-Labeled Tigecycline

| Peak | $t_R$ (min)[a] | [M + H]$^+$ | Site of Metabolism | Metabolite | Matrix[b] |
|---|---|---|---|---|---|
| M3a | 3.3 | 132 | TBAAA side chain | t-Butylaminoacetic acid | S, U, F |
| M6 | 33.1 | 762 | Hydroxy group of ring A, C or D | Epimer of Tigecycline Glucudonide | S, U, F |
| M7 | 35.9 | 762 | Hydroxy group of ring A, C or D | Tigecycline Glucudonide | S, U, F |
| M1 | 38.8 | 602 | Tetracycline ring or dimethylamino group | Hydroxy Tigecycline | U |
| M8 | 39.5 | 515 | Butylamine group | Epimer of N-Acetyl-9-aminominocycline | S, U |
| M2 | 40.7 | 602 | Ring A, B or C or dimethylamino group | Hydroxy Tigecycline | U |
| M3 | 41.5 | 473 | 9 position, loss of TBAAA[c] side chain | 9-Aminominocycline | S, U |
| M9 | 42.4 | 515 | Butylamine group | N-Acetyl-9-aminominocycline | S, U |

TABLE 4-continued

Tigecycline Related Compounds Observed in Human Serum, Urine and Feces Following Intravenous Administration of a Single 50 mg Dose of [14C]-Labeled Tigecycline

| Peak | $t_R$ (min)[a] | [M + H]+ | Site of Metabolism | Metabolite | Matrix[b] |
|------|----------------|----------|--------------------|--------------------|-----------|
| M4   | 43.7           | 602      | Tetracycline ring or dimethylamino group | Hydroxy Tigecycline | U |
|      | 47.4           | 586      | D-Ring dimethylamino group | Epimer of Tigecycline | S, U, F |
|      | 50.4           | 586      | None               | Tigecycline        | S, U, F |

[a]LC/MS retention time taken from or normalized to data file UL_010703_0004. M3a retention time taken from the subject 1, 1 hour serum radiochromatogram.
[b]S, serum; U, urine; F, feces
[c]TBAAA = t-butylaminoacetylamino The mass spectral data for the characterized tigecycline metabolites in human serum, urine and feces are discussed below.

Characterization of the tigecycline metabolites in human serum, urine and feces, and rat and dog plasma and urine was performed using LC/MS analysis (Table 5). Structures of these metabolites are shown in Scheme 1. It is expected that substantially pure M6 or M7 could be isolated using standard chromatographic techniques. For instance, the HPLC parameters used in examples 7, 8 and 9 would be expected to provide substantially pure aliquots of M6 and M7.

Accordingly in a further aspect this invention provides a tigecycline metabolite as described herein in substantially pure form, e.g having a purity≧about 90%, preferably ≧about 95% or more, such as 98%.

TABLE 5

Summary of Mass Spectral Data for Tigecycline and its Metabolites Detected in Humans, Dogs and/or Rats

| Metabolite | Species[1] | MW | [M + H]+ | Product ions of [M + H]+ |
|------------|------------|-----|----------|---------------------------|
| M3a (t-Butylaminoacetic acid) | R, D, H | 131 | 132 | |
| M6 (epimer of Tigecycline glucuronide) | H | 761 | 762 | 586, 569, 513, 211, 86 |
| M7 (Tigecycline glucuronide) | H | 761 | 762 | 586, 569, 513, 211, 154, 86 |
| M8 (epimer of N-Acetyl-9-aminominocycline) | H | 514 | 515 | 498, 456, 411, 154 |
| M3 (9-Aminominocycline) | R, D, H | 472 | 473 | 456 |
| M9 (N-Acetyl-9-aminominocycline) | H | 514 | 515 | 498, 456, 411, 154 |
| Hydroxy Tigecycline | R, D, H | 601 | 602 | 585, 529, 472, 211, 154, 86 |
| Epimer of Tigecycline | R, D, H | 585 | 586 | 569, 513, 456, 411, 211, 154, 86 |
| Tigecycline | R, D, H | 585 | 586 | 569, 513, 482, 456, 411, 211, 154, 86 |

[1]R = rat, D = dog, H = human

Figure 9:
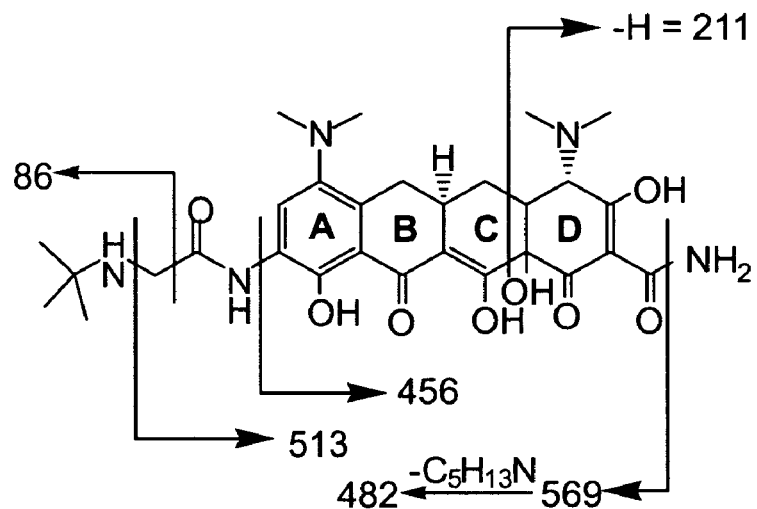
FIG. 9 is the product ions of m/z 586 mass spectrum for tigecycline.
Figure 9:
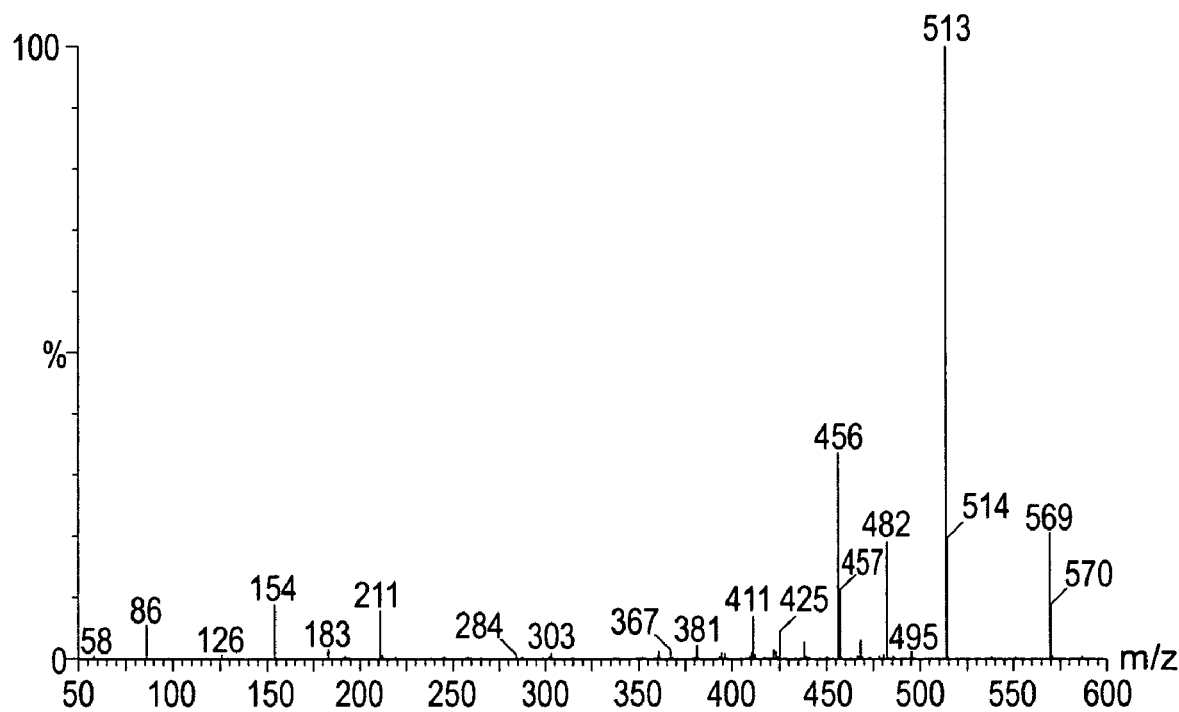

Tigecycline was observed in serum, urine and feces. The mass spectral characteristics of tigecycline authentic standard were examined for comparison with metabolites. In the LC/MS spectrum of tigecycline, a protonated molecular ion, [M+H]+, was observed at m/z 586. The MS/MS spectrum obtained from collision activated dissociation of m/z 586 of tigecycline and the proposed fragmentation scheme are shown in FIG. 9. Loss of NH$_3$ from m/z 586 generated the m/z 569 product ion. The product ion at m/z 513 represented loss of the t-butylamino group from the t-butylaminoacetylamino (TBAAA) side chain. Loss of the entire TBAAA side chain and subsequent loss of the 4-dimethylamino group generated product ions at m/z 456 and 411, respectively. The product ion at m/z 211 originated from the D ring of the tetracycline ring system as indicated in the fragmentation scheme. The m/z 86 ion represented the t-butylaminomethylene group.

Figure 10:
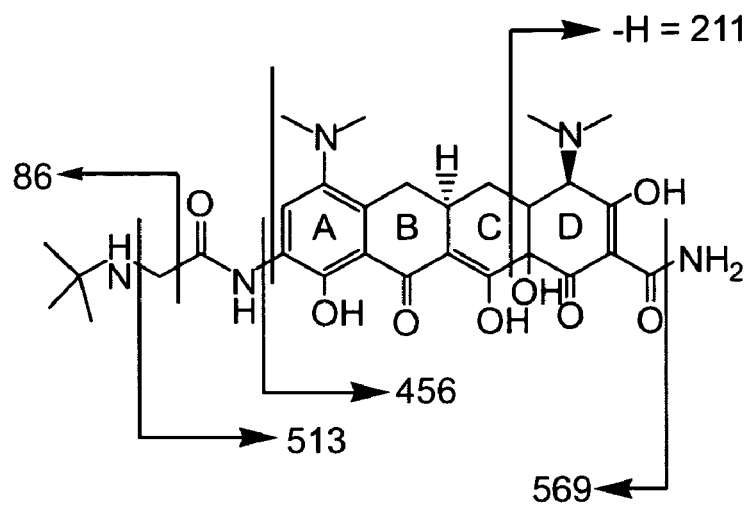
FIG. 10 is the product ions of m/z 586 mass spectrum for the epimer of tigecycline.
Figure 10:
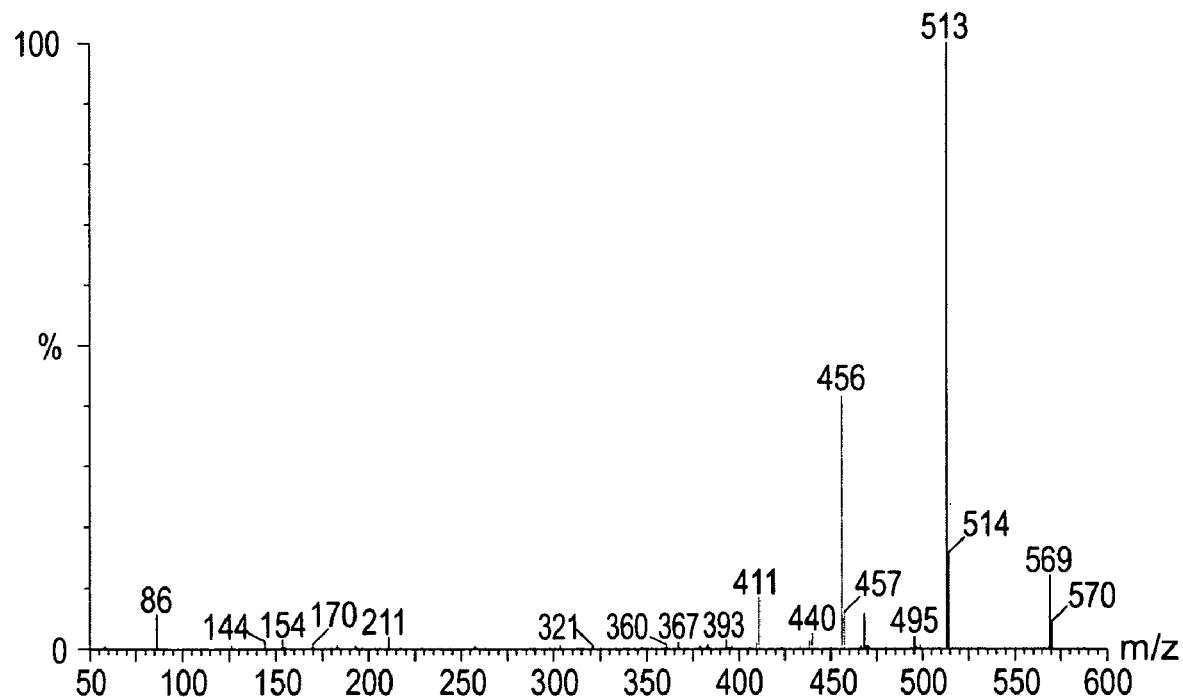

The epimer of tigecycline was observed in serum, urine and feces. This product generated a [M+H]+ at m/z 586. The product ions of m/z 586 mass spectrum, shown in FIG. 10, includes m/z 569, 513, 456, 411, 211, 154 and 86 that were also present for tigecycline. Identification as the epimer was made based on its relative retention time being shorter than that of tigecycline.

Figure 11:
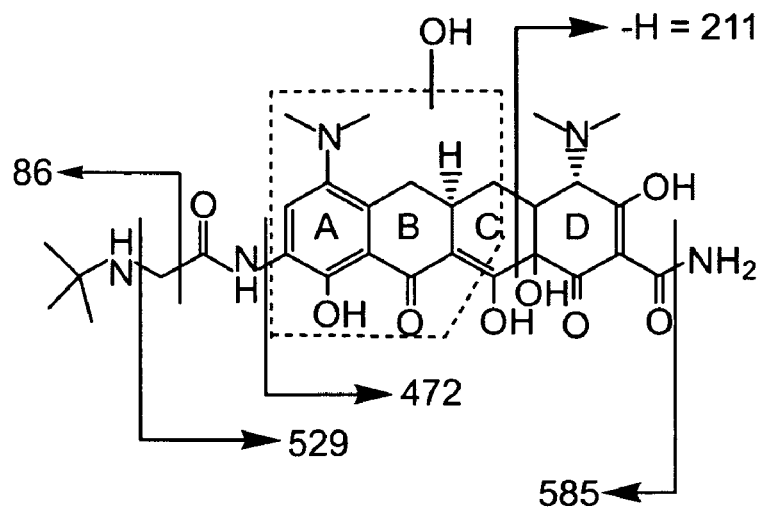
FIG. 11 is the product ions of m/z 602 mass spectrum for M2.
Figure 11:
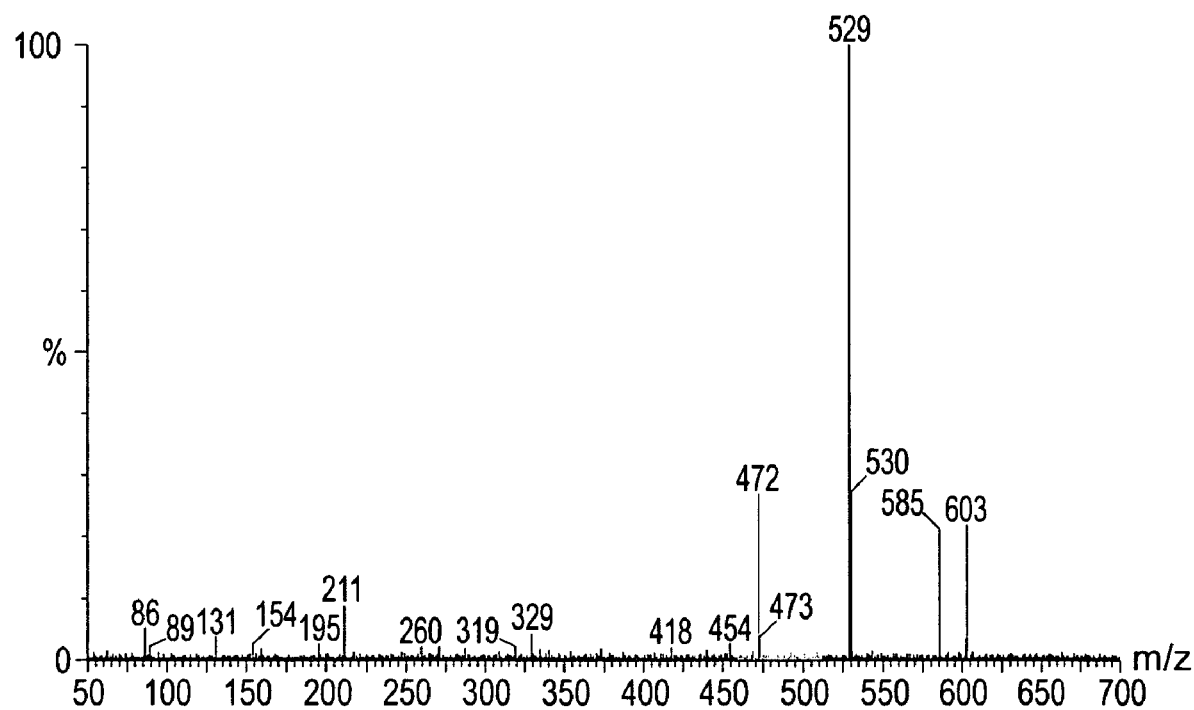

Metabolites M1, M2 and M4 were observed in urine in trace amounts. These metabolites produced a [M+H]+ at m/z 602. The proposed fragmentation scheme and product ions of m/z 602 mass spectrum for M2 are shown in FIG. 11. Product ions at m/z 529 and 472 were 16 Da larger than the corresponding ions at m/z 513 and 456, respectively, for tigecycline. This indicated that the tetracycline ring was the site of metabolism rather than the t-butylamino-acetylamino group. The presence of a product ion at m/z 211, also observed for tigecycline, eliminated Ring D of the tetracycline as a site of metabolism. Mass spectral data for M1 and M4 were similar to that for M2, except that the m/z 211 product ion was not observed for either M1 or M4. Therefore, the M1, M2 and M4 metabolites were the product of oxidation of the tetracycline moiety.

Figure 12A:
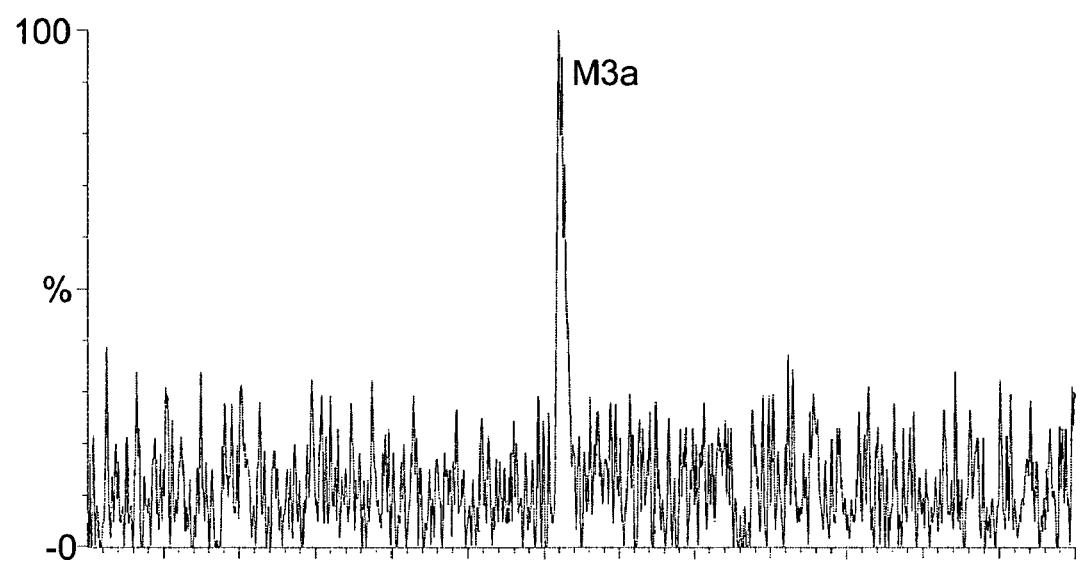
FIG. 12A is a radiochromatogram for M3a isolated from human urine.
Figure 12B:
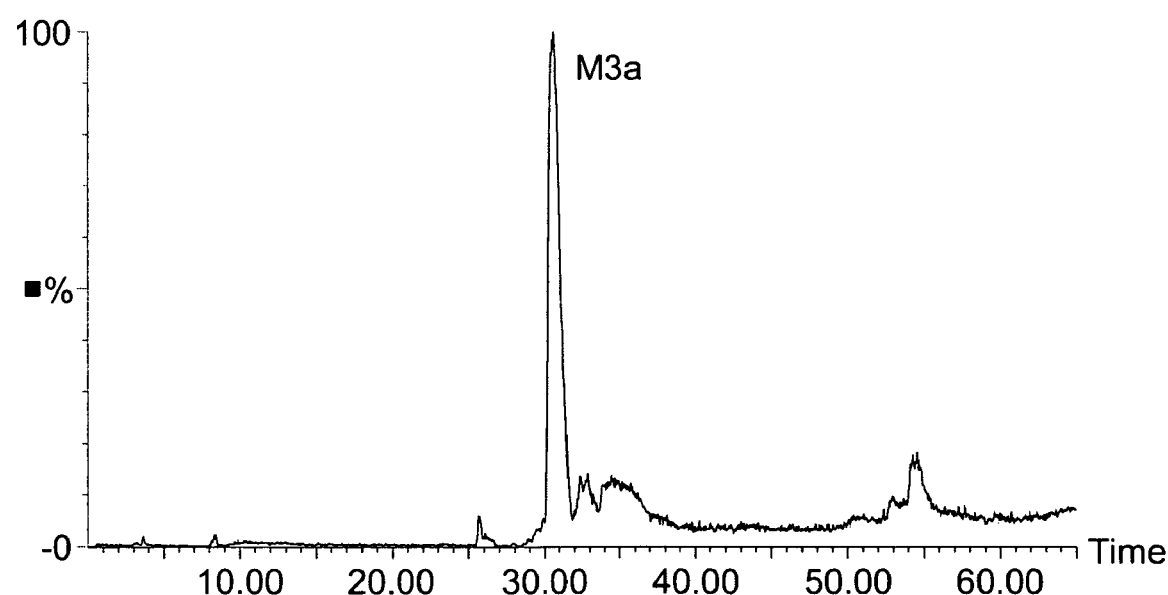
FIG. 12B is a mass chromatogram for M3a isolated from human urine.
Figure 13:
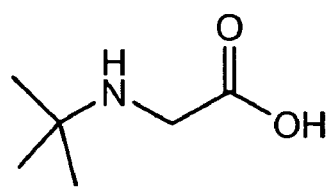
Figure 13:
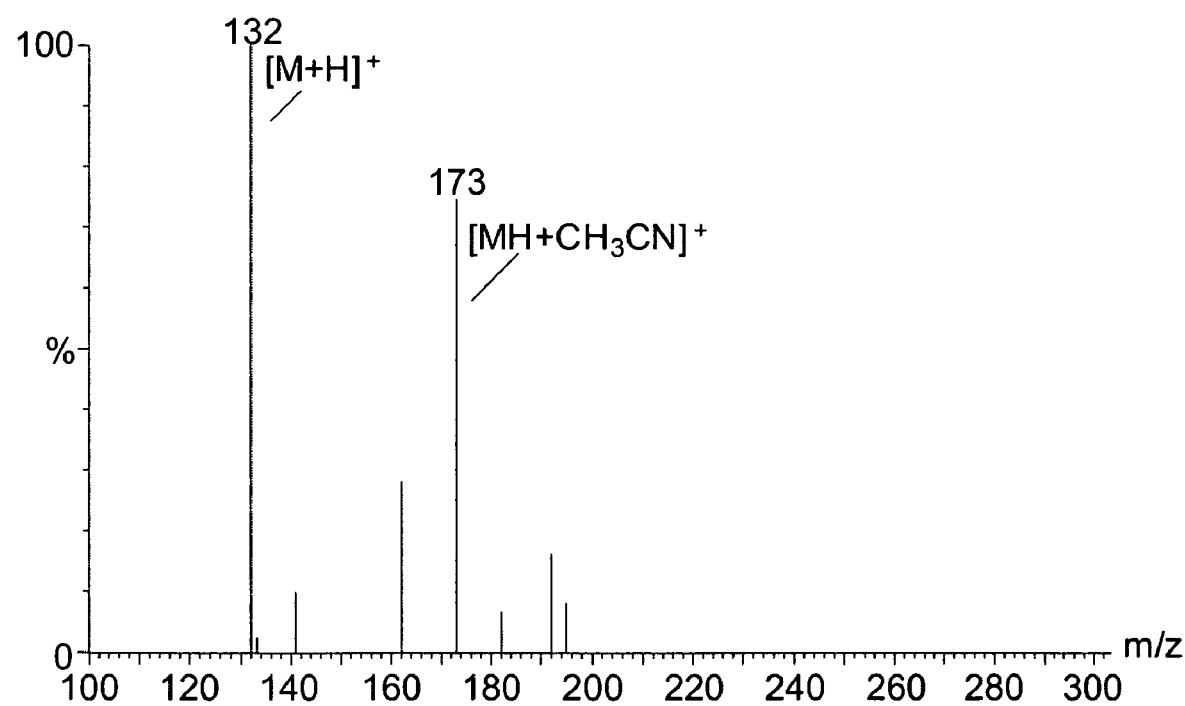
Figure 14:
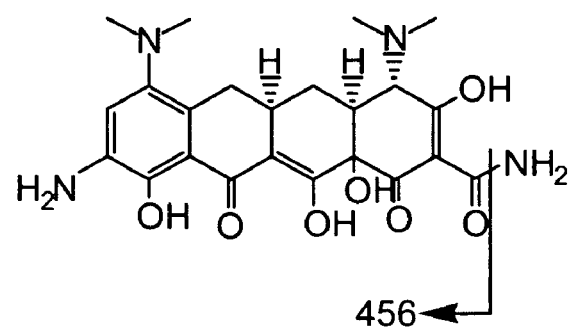
FIG. 14 is the LC/SRM chromatogram of the m/z 473→456 SRM transition for M3 (9-aminominocycline) in human serum.
Figure 14:
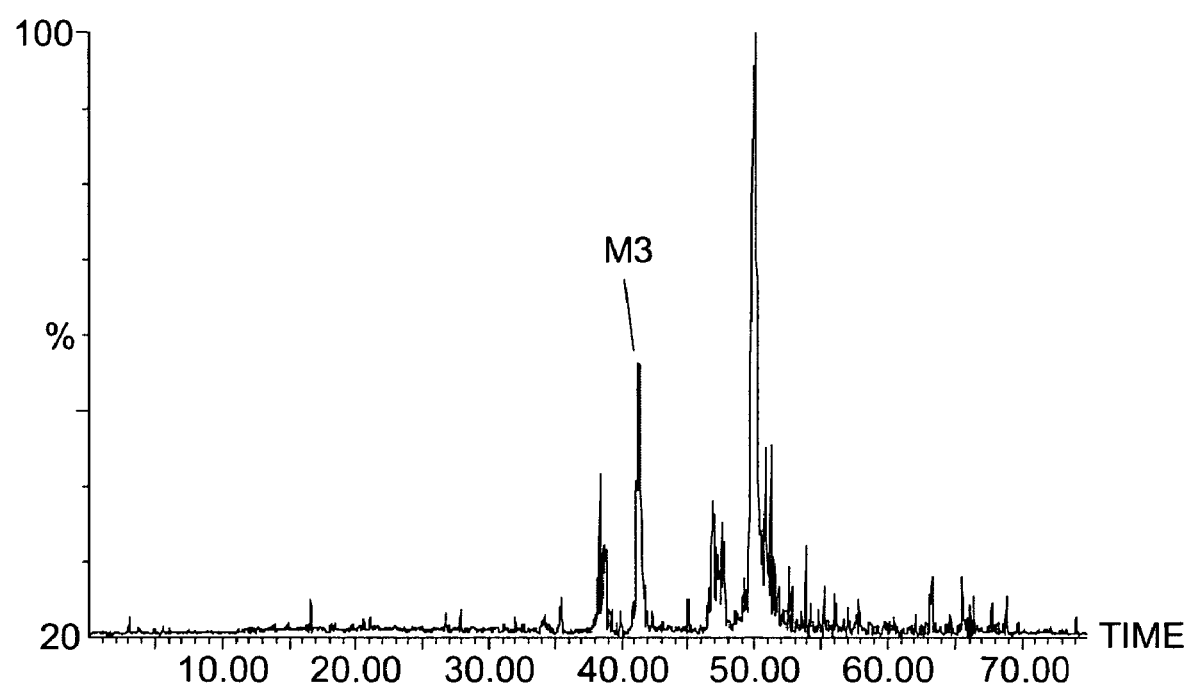

Metabolite M3a was observed in serum, urine and feces, as an early eluting radiochromatographic peak. Isolation of this early eluting M3a peak from human urine and subsequent LC/MS analysis with normal phase HPLC resulted in the radio- and mass chromatograms shown in FIGS. 12A and 12B. The [M+H]$^+$ and [MH+CH$_3$CN]$^+$ for M3a were observed at m/z 132 and 173, respectively, as shown in FIG. 13. This indicated a molecular weight of 131. Metabolite M3 was observed in serum and urine in trace amounts only by LC/MS due to loss of the radiolabel. The [M+H]$^+$ for metabolite M3 was observed at m/z 473. The product ions of m/z 473 mass spectrum included m/z 456 (data not shown), generated from loss of NH$_3$, which was characteristic of tigecycline related compounds. In serum samples, this metabolite was observed by monitoring the m/z 473→456 SRM transition as shown in FIG. 14. Identification of M3 as CL-318614 (9-aminominocycline) was achieved in a dog metabolism study. Metabolite M3 was proposed to have been generated by amide hydrolysis of the TBAAA side chain with radiolabeled t-butylaminoacetic acid (M3a) as a byproduct.

Figure 15:
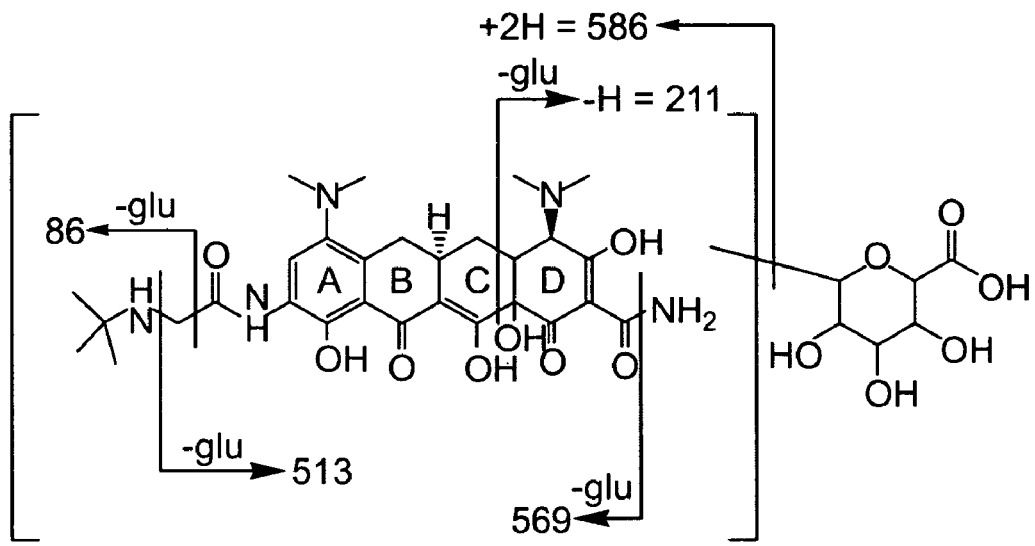
FIG. 15 is the product ions of M/Z 762 mass spectrum for M6.
Figure 15:
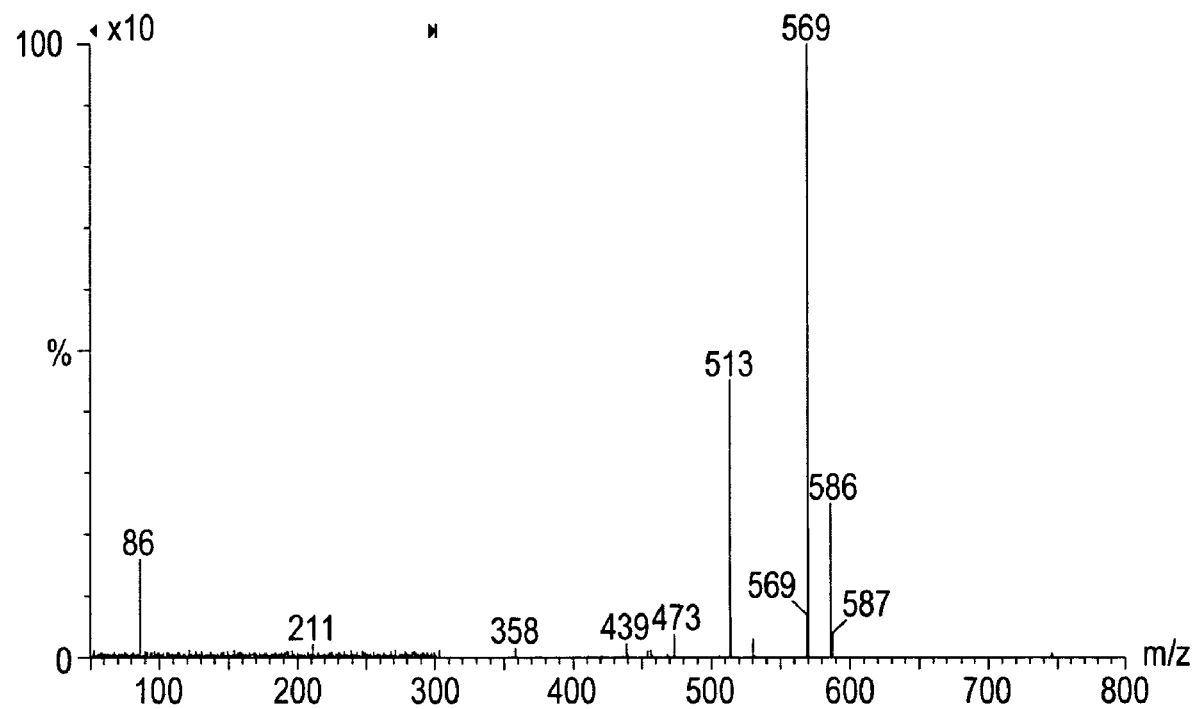
Figure 16:
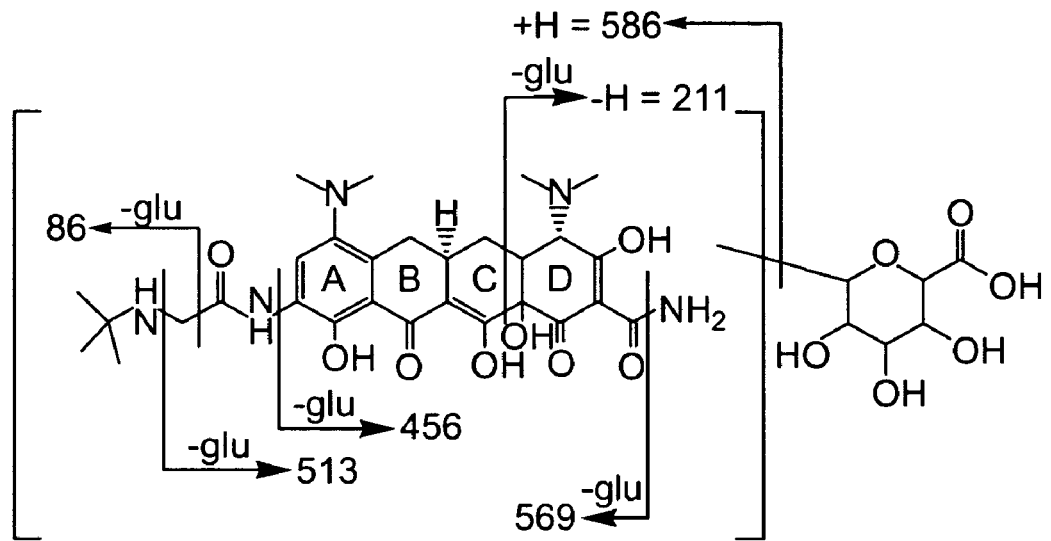
FIG. 16 is the product ions of M/Z 762 mass spectrum for M7.
Figure 16:
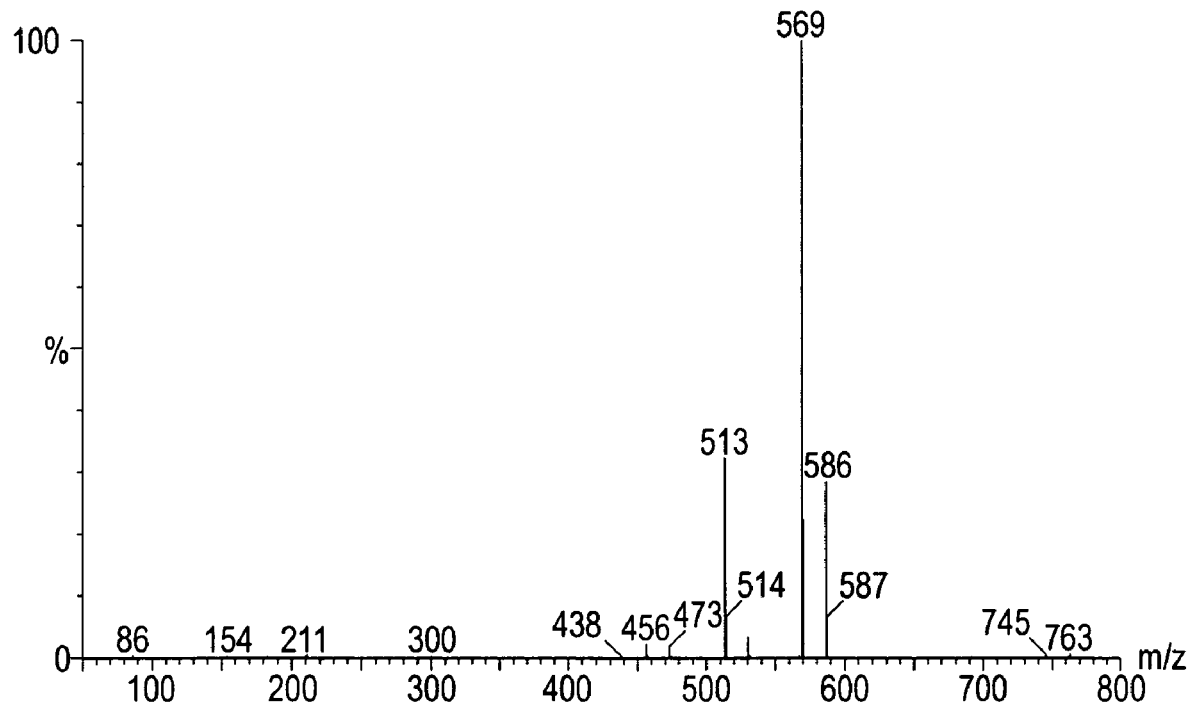

Metabolites M6 and M7 were observed in serum, urine and feces. The [M+H]$^+$ for M6 and M7 was observed at m/z 762, which was 176 Da larger than tigecycline. Mass spectral data for M6 and M7 were similar. The protonated molecular ion peak at m/z 762 was indicative of the presence of a glucuronide metabolite of tigecycline or its corresponding epimer. The product ions of m/z 762 mass spectra for M6 and M7 are shown in FIGS. 15 and 16, respectively. Product ions of M6 and M7 were present at m/z 586, 569, 513, 211, and 86, and at 154 for M7. For M6 and M7, neutral loss of 176 Da generated m/z 586, which was also the [M+H]$^+$ for tigecycline, and which indicated a glucuronide of tigecycline. Product ions at m/z 569, 513, 456, 211, 154 (m/z 154 was observed for M7, but not M6) and 86 were also observed for tigecycline. Metabolite M6 was proposed to be the epimer of M7 based on its HPLC retention time being earlier than that of M7. This was consistent with the tigecycline epimer eluting earlier than tigecycline. Therefore, M6 and M7 were proposed to be glucuronides of the tigecycline epimer and of tigecycline, respectively.

Figure 17:
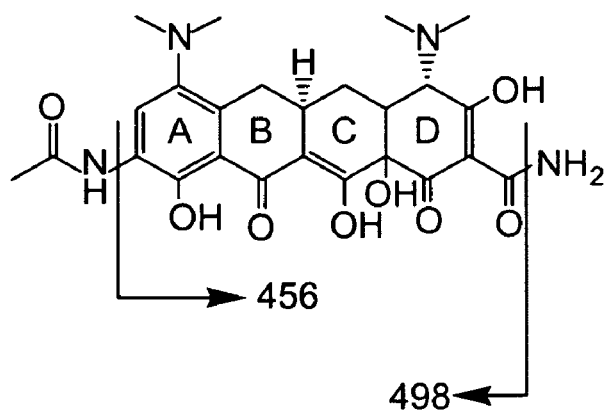
FIG. 17 is the product ions of M/Z 515 mass spectrum for M9.
Figure 17:
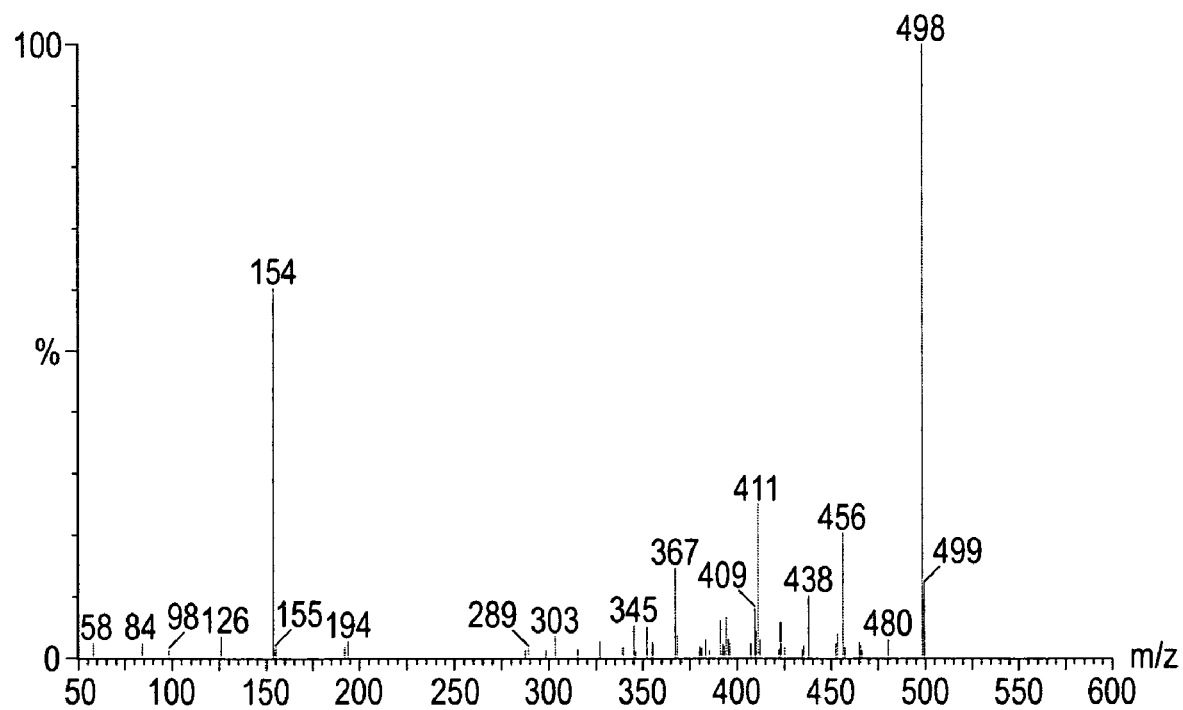

Metabolites M8 and M9 were observed in serum and urine, and only by LC/MS. The [M+H]$^+$ for M8 and M9 was observed at m/z 515 (MW 514), which was 71 Da smaller than tigecycline. Mass spectral data for M8 and M9 were similar. The product ions of m/z 515 mass spectrum for M9 is shown in FIG. 17. Loss of NH$_3$ from m/z 515 generated the m/z 498 product ion. Product ions at m/z 456, 411 and 154 were also observed for tigecycline, and indicated the tetracycline ring was intact. The lack of radiochromatographic peaks for M8 and M9 was consistent with loss of the radiolabeled carbonyl group of the TBAAA side chain. The most likely mechanism for formation of M9 was amide hydrolysis to generate t-butylaminoacetic acid (M3a, which contained the radiolabel) and 9-aminominocycline (M3, no $^{14}$C label). N-acetylation of 9-aminominocycline was proposed to generate M9. The 58 Da difference between the m/z 456 product ion and molecular weight (514) was consistent with the presence of a non-radiolabeled labeled acetylamino group. Confirmation of these metabolites was obtained by co-chromatography of a urine extract spiked with synthetic N-acetyl-9-aminominocycline (WAY-188749) (data not shown). Metabolite M8 was proposed to be the epimer of M9 based on its HPLC retention time being earlier than that of M9. This was consistent with the tigecycline epimer eluting earlier than tigecycline. Therefore, M8 and M9 were identified as the epimer of N-acetyl-9-aminominocycline and N-acetyl-9-aminominocycline, respectively.

Figure 18:
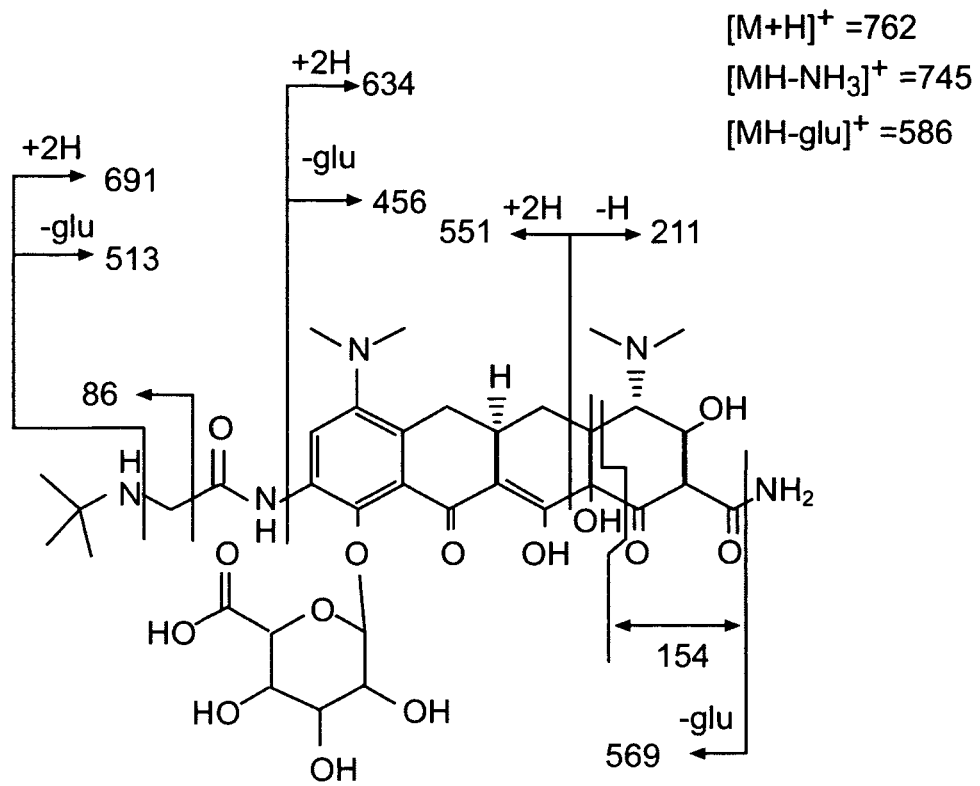
FIG. 18 is the proposed structure and mass spectral fragmentation scheme for Tigecycline glucuronide.
Figure 18:
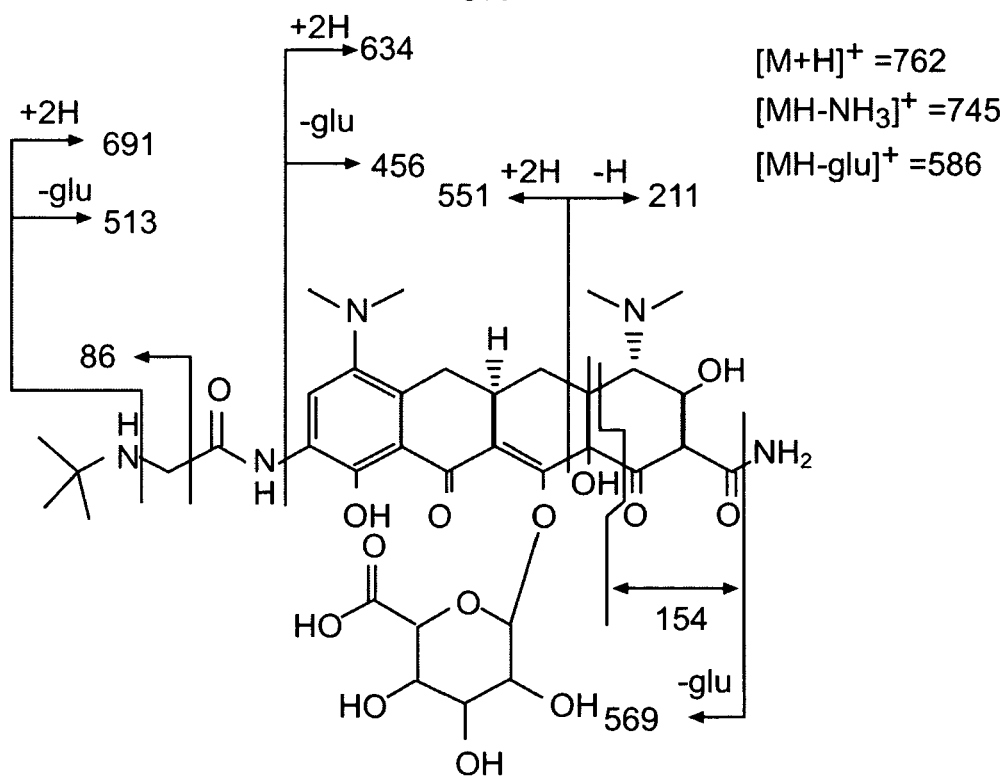
Figure 19A:
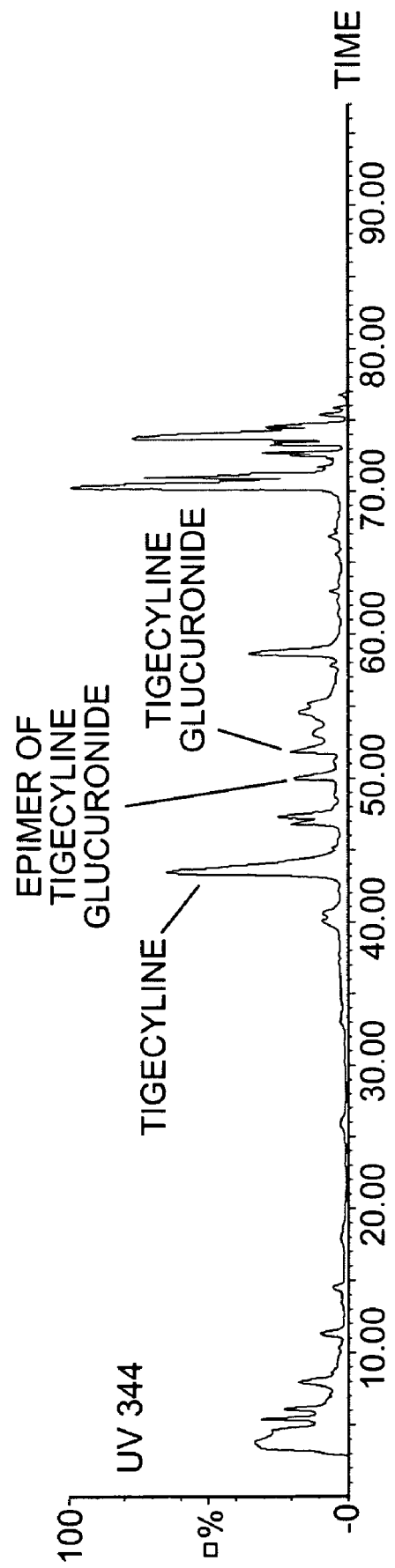
FIG. 19A is a UV chromatogram from LC/MS analysis of human urine from a subject administered tigecycline.
Figure 19B:
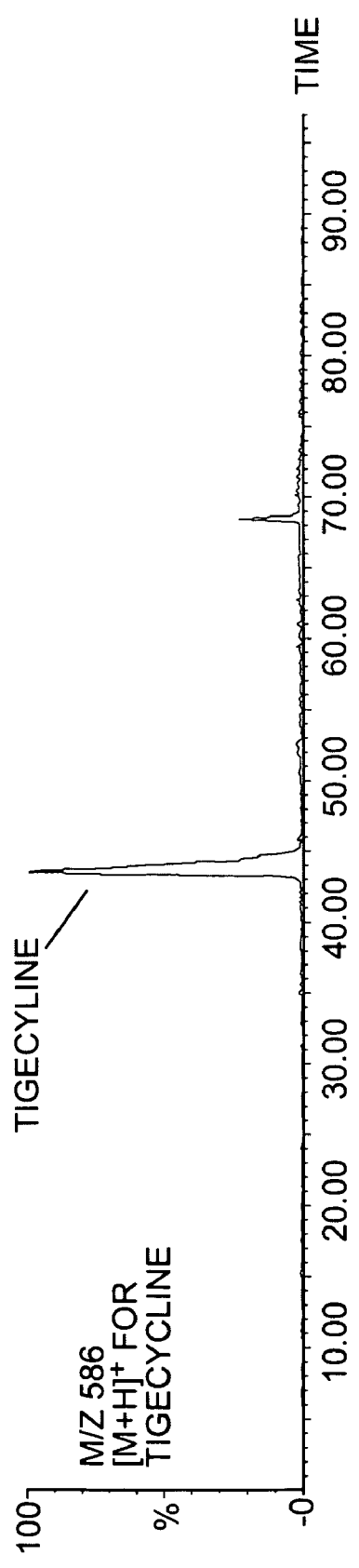
FIG. 19B is a selected mass chromatogram from LC/MS analysis of human urine from a subject administered tigecycline.
Figure 19C:
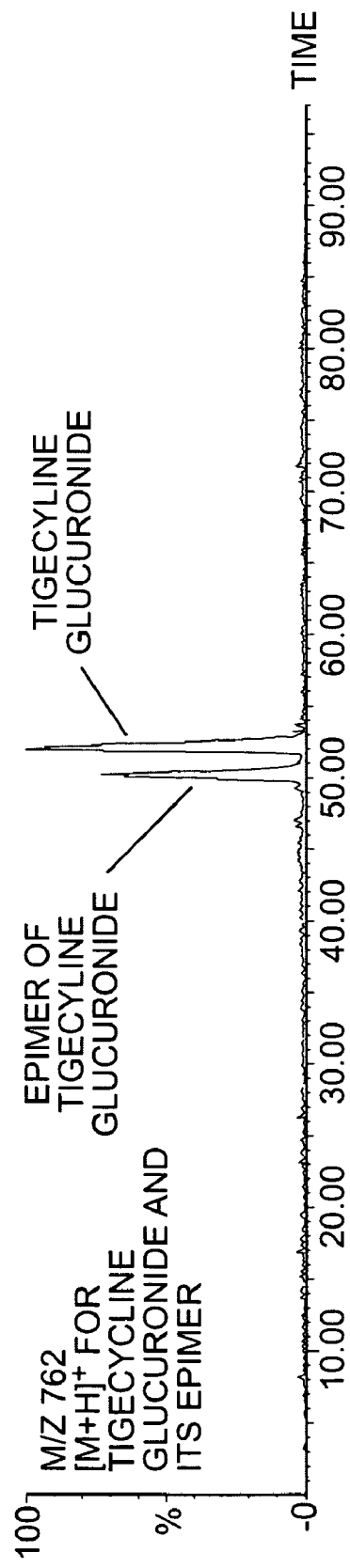
FIG. 19C is a selected mass chromatogram from LC/MS analysis of human urine from a subject administered tigecycline.
Figure 20A:
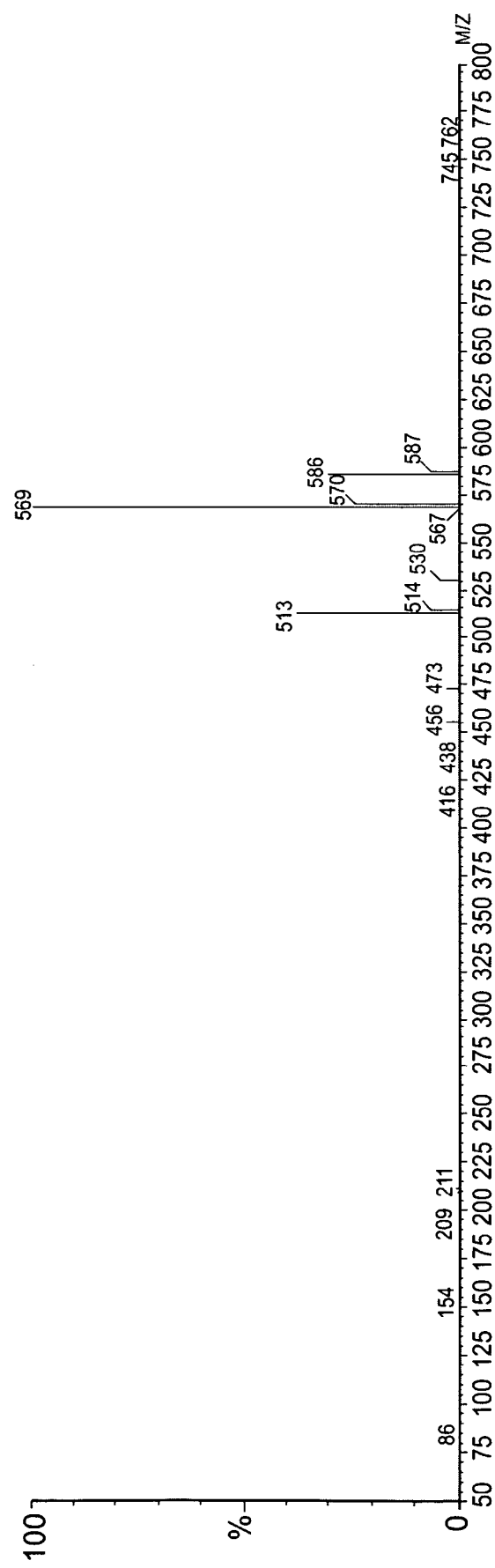
FIG. 20A is a full scale plot of product ions of m/z 762 mass spectrum of tigecycline glucuronide: and (B) plot magnified to show less intense product ions.
Figure 20B:
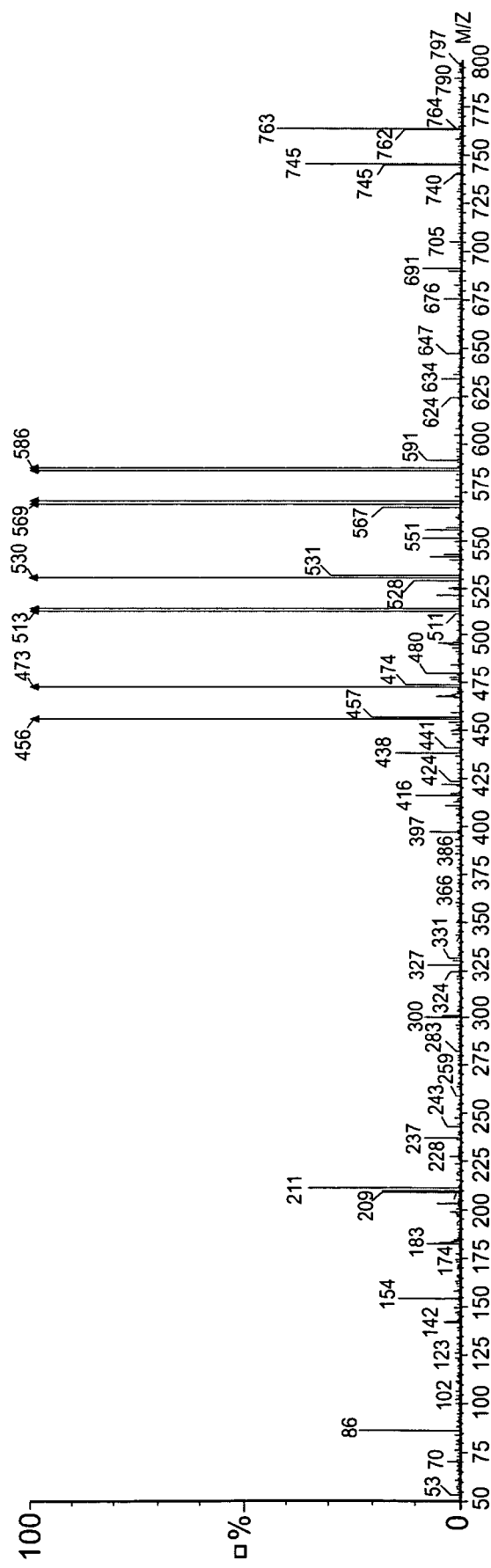
FIG. 20B is a plot of product ions of m/z 762 mass spectrum of tigecycline glucuronide magnified to show less intense product ions.
Figure 21C:
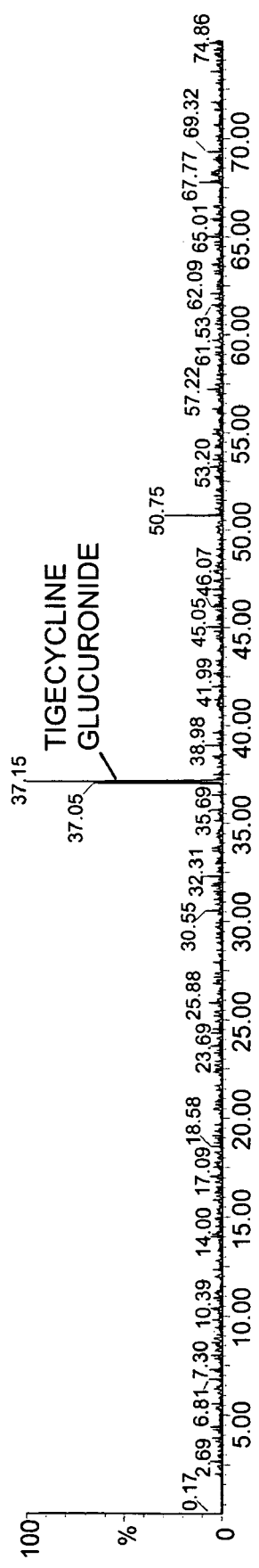
FIG. 21C is a LC/MS/MS chromatogram from product ions of m/z 762 analysis of human urine from a subject administered tigecycline showing low intensity product ions.
Figure 21D:
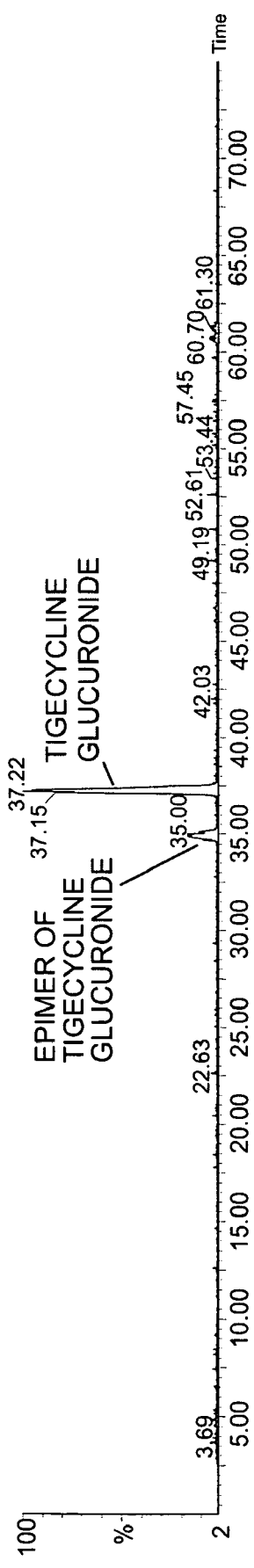
FIG. 21D is a LC/MS/MS chromatogram from product ions of m/z 762 analysis of human urine from a subject administered tigecycline showing a total ion chromatogram.

FIGS. 18-21 relate to further analysis of tigecycline glucuronide. FIG. 18 is the proposed structure and mass spectral fragmentation scheme for tigecycline glucuronide, which can correspond to structures I, II epimer, III, and IV epimer. FIG. 19A a UV chromatogram and FIGS. 19B and 19C are selected mass chromatograms from LC/MS analysis of human urine from a subject administered tigecycline. FIGS. 20A and 20B shows product Ions of m/z 762 mass spectrum of tigecycline glucuronide, where FIG. 20A is a full scale plot and FIG. 20B is a plot magnified to show less intense product ions. FIGS. 21A-21D shows LC/MS/MS chromatograms from product ions of m/z 762 analysis of human urine from a subject administered tigecycline, where FIGS. 21A-21C are selected mass chromatograms of low intensity product ions and FIG. 21D is a total ion chromatogram. Accordingly, possible structures of the metabolite and its epimer include at least one compound chosen from I, II epimer, III, and IV epimer, as previously disclosed herein.

In one embodiment, the compounds disclosed herein may be used as a treatment against drug-resistant bacteria, and it has been shown to work where other antibiotics have failed. For example, it may be active against methicillin-resistant *Staphylococcus aureus*, penicillin-resistant *Streptococcus pneumoniae*, vancomycin-resistant enterococci (D. J. Beidenbach et. al., Diagnostic Microbiology and Infectious Disease 40:173-177 (2001); H. W. Boucher et. al., Antimicrobial Agents & Chemotherapy 44:2225-2229 (2000); P.A. Bradford Clin. Microbiol. Newslett. 26:163-168 (2004); D. Milatovic et. al., Antimicrob. Agents Chemother. 47:400-404 (2003); R. Patel et. al., Diagnostic Microbiology and Infectious Disease 38:177-179 (2000); P. J. Petersen et. al., Antimicrob. Agents Chemother. 46:2595-2601 (2002); and P. J. Petersen et. al., Antimicrob. Agents Chemother. 43:738-744 (1999), and against organisms carrying either of the two major forms of tetracycline resistance: efflux and ribosomal protection (C. Betriu et. al., Antimicrob. Agents Chemother. 48:323-325 (2004); T. Hirata et. al. Antimicrob. Agents Chemother. 48:2179-2184 (2004); and P. J. Petersen et. al., Antimicrob. Agents Chemother. 43:738-744(1999).

In one embodiment, the compounds disclosed herein may be used in the treatment of many bacterial infections, such as complicated intra-abdominal infections (cIAI), complicated skin and skin structure infections (cSSSI), Community Acquired Pneumonia (CAP), and Hospital Acquired Pneumonia (HAP) indications, which may be caused by gram-negative and gram-positive pathogens, anaerobes, and both methicillin-susceptible and methicillin-resistant strains of *Staphylococcus aureus* (MSSA and MRSA). Additionally, the compounds disclosed herein may be used to treat or control bacterial infections in warm-blooded animals caused by bacteria having the TetM and TetK resistant determinants. Also, the compounds disclosed herein may be used to treat bone and joint infections, catheter-related Neutropenia, obstetrics and gynecological infections, or to treat other resistant pathogens, such as VRE, ESBL, enterics, rapid growing mycobacteria, and the like.

Accordingly, disclosed herein is one embodiment of a method of treating at least one bacterial infection, comprising:

administering to a subject in need thereof a pharmaceutical composition comprising therapeutically effective amount of at least one of the compounds disclosed herein and pharmaceutically acceptable salts thereof.

In one embodiment, the compounds disclosed herein may reduce nausea, for example, as compared to tigecycline.

"Pharmaceutical composition" as used herein refers to a medicinal composition. The pharmaceutical composition may contain at least one pharmaceutically acceptable carrier.

"Pharmaceutically acceptable excipient" as used herein refers to pharmaceutical carriers or vehicles suitable for administration of the compounds provided herein including any such carriers known to those skilled in the art to be suitable for the particular mode of administration. For example, solutions or suspensions used for parenteral, intradermal, subcutaneous, or topical application can include a sterile diluent (e.g., water for injection, saline solution, fixed oil, and the like); a naturally occurring vegetable oil (e.g., sesame oil, coconut oil, peanut oil, cottonseed oil, and the like); a synthetic fatty vehicle (e.g., ethyl oleate, polyethylene glycol, glycerine, propylene glycol, and the like, including other synthetic solvents); antimicrobial agents (e.g., benzyl alcohol, methyl parabens, and the like); antioxidants (e.g., ascorbic acid, sodium bisulfite, and the like); chelating agents (e.g., ethylenediaminetetraacetic acid (EDTA) and the like); buffers (e.g., acetates, citrates, phosphates, and the like); and/or agents for the adjustment of tonicity (e.g., sodium chloride, dextrose, and the like); or mixtures thereof. By further example, where administered intravenously, suitable carriers include physiological saline, phosphate buffered saline (PBS), and solutions containing thickening and solubilizing agents such as glucose, polyethylene glycol, polypropyleneglycol, and the like, and mixtures thereof.

By way of non-limiting example, the compounds disclosed herein may be optionally combined with one or more pharmaceutically acceptable excipients, and may be administered orally in such forms as tablets, capsules, dispersible powders, granules, or suspensions containing, for example, from about 0.05 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.05 to 5% suspending agent in an isotonic medium. Such pharmaceutical preparations may contain, for example, from about 25 to about 90% of the active ingredient in combination with the carrier, more usually between about 5% and 60% by weight. Other formulations are discussed in U.S. Pat. Nos. 5,494,903 and 5,529,990, the disclosures of which are herein incorporated by reference.

The terms "pharmaceutically acceptable salt" can refer to acid addition salts or base addition salts of the compounds in the present disclosure. A pharmaceutically acceptable salt is any salt which retains the activity of the parent compound and does not impart any deleterious or undesirable effect on the subject to whom it is administered and in the context in which it is administered. Pharmaceutically acceptable salts include metal complexes and salts of both inorganic and organic acids. Pharmaceutically acceptable salts include metal salts such as aluminum, calcium, iron, magnesium, manganese and complex salts. Pharmaceutically acceptable salts include acid salts such as acetic, aspartic, alkylsulfonic, arylsulfonic, axetil, benzenesulfonic, benzoic, bicarbonic, bisulfuric, bitartaric, butyric, calcium edetate, camsylic, carbonic, chlorobenzoic, cilexetil, citric, edetic, edisylic, estolic, esyl, esylic, formic, fumaric, gluceptic, gluconic, glutamic, glycolic, glycolylarsanilic, hexamic, hexylresorcinoic, hydrabamic, hydrobromic, hydrochloric, hydroiodic, hydroxynaphthoic, isethionic, lactic, lactobionic, maleic, malic, malonic, mandelic, methanesulfonic, methylnitric, methylsulfuric, mucic, muconic, napsylic, nitric, oxalic, p-nitromethanesulfonic, pamoic, pantothenic, phosphoric, monohydrogen phosphoric, dihydrogen phosphoric, phthalic, polygalactouronic, propionic, salicylic, stearic, succinic, sulfamic, sulfanilic, sulfonic, sulfuric, tannic, tartaric, teoclic, toluenesulfonic, and the like. Pharmaceutically acceptable salts may be derived from amino acids, including but not limited to cysteine. Other acceptable salts may be found, for example, in Stahl et al., *Pharmaceutical Salts: Properties, Selection, and Use*, Wiley-VCH; 1st edition (Jun. 15, 2002).

In one embodiment, "therapeutically effective amount" refers to that amount of a compound that results in prevention or amelioration of symptoms in a patient or a desired biological outcome, e.g., improved clinical signs, delayed onset of disease, reduced/elevated levels of lymphocytes and/or antibodies, etc. The effective amount can be determined as described herein. The selected dosage level will depend upon the activity of the particular compound, the route of administration, the severity of the condition being treated, and the condition and prior medical history of the patient being treated. However, it is within the skill of the art to start doses of the compound at levels lower than required to achieve the desired therapeutic effect and to gradually increase the dosage until the desired effect is achieved. In one embodiment, the data obtained from the assays can be used in formulating a range of dosage for use in humans.

CONTROL EXAMPLE 1

Figure 22:
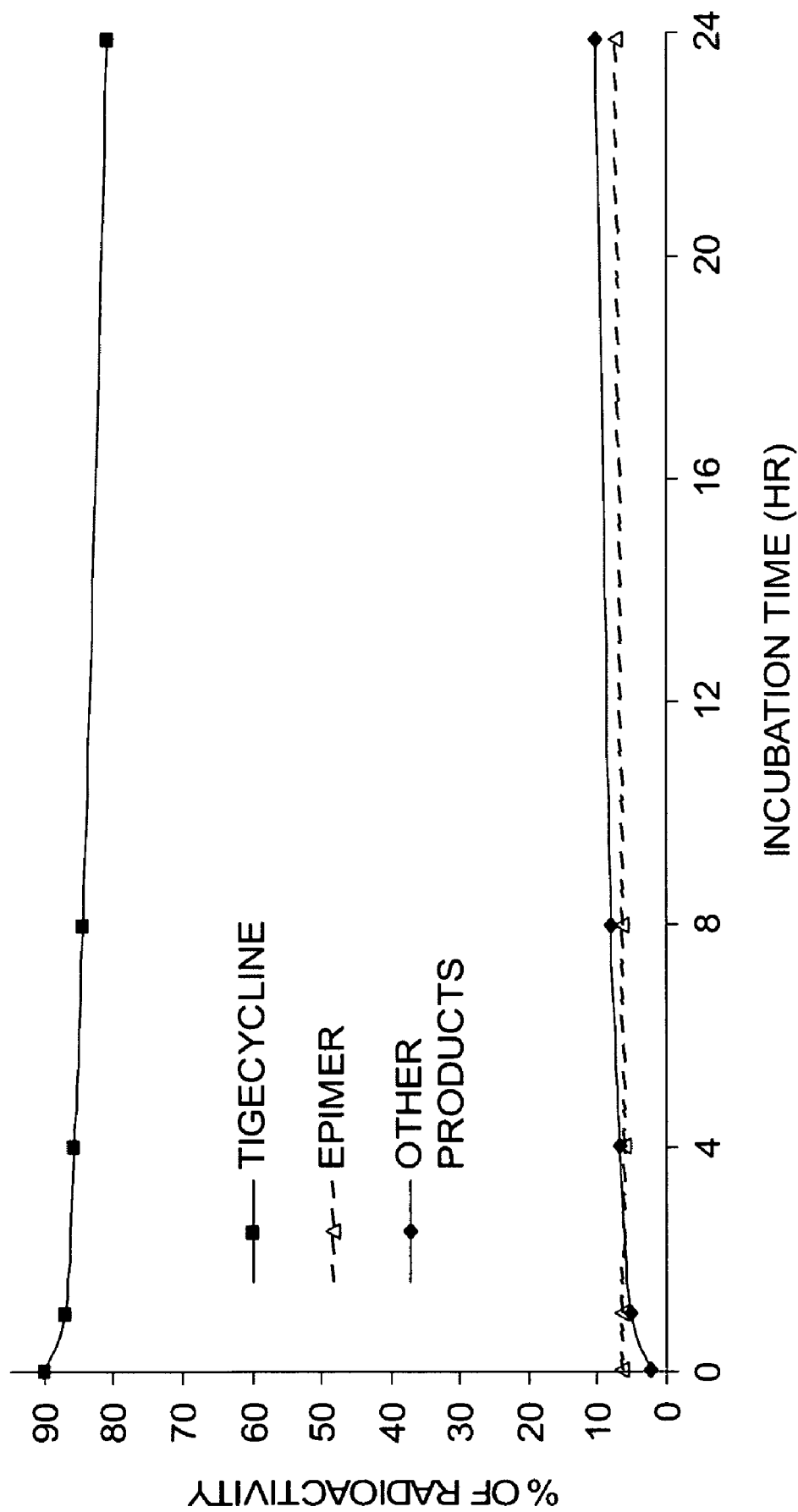
FIG. 22 is the stability of [$^{14}$C]tigecycline incubated at 37° C. in human serum.

The stability of [$^{14}$C]tigecycline was examined in control serum incubated at 37° C. for up to 24 hours. The percent radioactivity associated with [$^{14}$C]tigecycline in extracts of spiked control serum decreased approximately 9% over 24 hours, from 90% at 0 hours to 81% at 24 hours (FIG. 22). The percent of epimer at time zero was 7% and remained constant up to 24 hours. As reported for tetracyclines, (Remmers E G, Sieger G M, Doerschuk A P. Some observations on the kinetics of the C.4 epimerization of tetracycline. *J Pharm Sci.* 1963; 52;752-756, Nelis H, DeLeenheer A. Metabolism of minocycline in humans. *Drug Metab Dispos.* 1982; 10:142-146), the epimer of tigecycline was a product of epimerization and not considered a metabolite. The amount of other products increased approximately 8%, from 3% at 0 hours to 11% at 24 hours. Included in the other products is an early eluting chromatographic peak (M3a, t-butylaminoacetic acid), with a retention time of approximately 4 minutes. This peak was observed previously in rat and dog plasma and urine. The recovery of radioactivity from the spiked controls was complete for test samples from 0 to 24 hour.

CONTROL EXAMPLE 2

In urine, [$^{14}$C]tigecycline was less stable than in serum when incubated at 37° C. (FIG. 6). The percent of [$^{14}$C] tigecycline in spiked control urine decreased 18%, from 92% at 0 hours to 74% at 24 hours. The epimer increased 16%, from 7% of the radioactivity at 0 hours to 23% at 24 hours. Other minor products increased from 1% at time zero to 3% over 24 hours.

The stability of [$^{14}$C]tigecycline was examined in control serum and fecal homogenates during the extraction methods used for the study samples. In serum samples, [$^{14}$C]tigecycline accounted for 94% of the radioactivity prior to spiking and extracting the samples. After the extraction process, the amount of [$^{14}$C]tigecycline had decreased 24% to 70% of the radioactivity. There was a corresponding increase in other radioactive components, mainly the epimer of tigecycline, which increased from 4% prior to extraction to 22% following the extraction. Other minor products, which included M3a, increased from 2% prior to extraction to 8% following the extraction.

CONTROL EXAMPLE 3

Similar results were observed following the extraction of [$^{14}$C]tigecycline from control fecal homogenates. In these samples, [$^{14}$C]tigecycline accounted for 94% of the radioactivity prior to extraction and 68% following the extraction. There was a corresponding increase in the epimer of tigecycline, which represented 4% of the radioactivity prior to extraction and 23% following the extraction. The amount of M3a also increased 4%, from 1% to 5%, during the extraction. Other minor products represented less than 1% of the radioactivity prior to the extraction and 4% following the extraction.

EXAMPLES

Example 1

An open-label, inpatient, multiple-dose tigecycline, single-dose [$^{14}$C]tigecycline metabolic disposition and mass balance study was performed in six healthy male volunteers. The clinical protocol called for twelve subjects. Of these twelve, six received the radioactive dose (subjects 1, 4, 5, 6, 7, and 8 with subject 8 later dropping out of the study.) Eligible subjects were selected based on inclusion/exclusion criteria, medical history, physical examination and additional procedures outlined in the study protocol. Each subject received a 100 mg loading dose on the morning of Day 1, followed by a 50 mg maintenance dose every 12 hours for an additional 5 doses. On the morning of study Day 4, six subjects received a single 50 mg dose of [$^{14}$C]tigecycline (50 µCi). Each tigecycline dose was administered via a 30-minute intravenous infusion. The six healthy, male volunteers received the [$^{14}$C]-labeled tigecycline, with an average dose of 45.9±0.9 µCi (range 44.3 to 47.0 µCi). The radiochemical purity of the [$^{14}$C]tigecycline was reported as 98.6% at the time of dosing, with 0.4% of the radioactivity identified as the tigecycline epimer, and the specific activity was 1.00 µCi/mg.

Serum samples were collected for metabolite profiling prior to tigecycline dosing and 1, 4, 8, 24 and 48 hours following the [$^{14}$C]-labeled dose. For metabolite profiling, urine samples were collected at 0-4, 4-8, 8-24 and 24-48 hours and fecal samples were collected up to 48 hours following the [$^{14}$C]-labeled dose. Serum and urine samples, and fecal homogenates were shipped on dry ice to the Biotransformation Division of Drug Safety and Metabolism, Wyeth Research, Collegeville, Pa. The details of the sample collection and sample storage are described in the mass balance portion of the study. The 24-48 hour urine and fecal samples for subject #6 were incomplete since the subject withdrew from the study. While samples from this subject were used for metabolite profiling, the samples were not included in the mass balance calculations.

The details of the non-labeled and the [$^{14}$C]-labeled tigecycline used in the clinical portion of the study, and the preparation of the doses and the analysis of these batches are described in the mass balance portion of the study. The [$^{14}$C] tigecycline administered to the subjects (Formulation No. 0931854J, Lot Number 7981703) had a specific activity of 1.00 µCi/mg (50 µCi/50 mg dose). An additional batch of [$^{14}$C]tigecycline (batch CFQ13389, 95.3 µCi/mg, 97.2% radiochemical purity), used to assess the stability of [$^{14}$C] tigecycline in serum, urine and fecal homogenates, was received from Amersham Pharmacia Biotech, Buckinghamshire, England. Tigecycline reference standard (batch RS 738-4, with a purity of 98.4%), 9-aminominocycline reference standard (CL-318614, batch 14800B-89A) and N-acetyl-9-aminominocycline (WAY-188749, batch L23566-162) were received from Wyeth Research, Pearl River, N.Y. The structure of [$^{14}$C]tigecycline is shown below, with the site of the radiolabel identified (*).

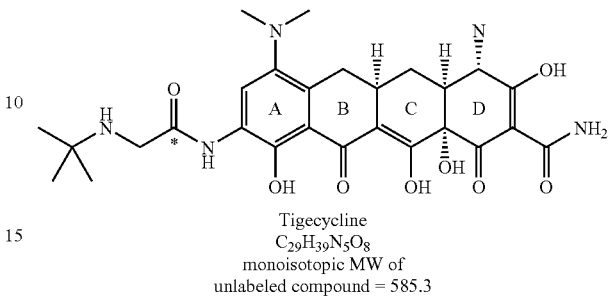

Tigecycline
$C_{29}H_{39}N_5O_8$
monoisotopic MW of
unlabeled compound = 585.3

Acetone, acetonitrile, glacial acetic acid and methanol were obtained from EMD Chemicals, Inc. (Gibbstown, N.J.). Ethylenediaminetetraacetic acid (EDTA) and trifluoroacetic acid were obtained from Sigma Chemical Co. (St. Louis, Mo.). Ammonium acetate was obtained from Mallinckrodt Baker (Phillipsburg, N.J.). All reagents were analytical grade or better.

Administration of intravenous tigecycline as a single 100-mg dose, followed by five 50-mg doses, and a single 50-mg dose of [$^{14}$C]tigecycline was generally safe and well tolerated. The most frequently reported (>10%) adverse events were nausea (75%), vomiting (50%), dyspepsia (17%), and injection site inflammation (17%).

Example 2

Radioactivity determinations, for calculating extraction efficiencies, were made using a Tri-Carb Model 3100TR liquid scintillation counter (Perkin Elmer, Wellesley, Mass.) using Ultima Gold™ scintillation fluid (Perkin Elmer) and an Ultima Gold™ standard curve. Counts per minute (CPM) were converted to disintegrations per minute (DPM) by use of external standards of known radioactivity. The quench of each standard was determined by the transformed spectral index of an external radioactive standard (tSIE). HPLC fractions collected into 96 well, deep well Luma plates (Perkin Elmer) were analyzed using a TopCount NXT radiometric microplate reader (Perkin Elmer).

Example 3

Individual serum samples, collected 1, 4 and 8 hours following the [$^{14}$C]-labeled tigecycline dose, were analyzed for metabolite profiles. The 24 and 48 hour samples were not analyzed because the concentrations of radioactivity were too low (range of 0 to 18 ng equivalents/mL). In order to minimize the sample volume, each serum sample was divided into two samples of equal volume (approximately 9 Ml each) and extracted and analyzed separately. EDTA (80 µL of 0.5 M EDTA per 1 mL of sample) was added to each sample and the samples vortex mixed. Three volumes of acetone were added to each sample and the sample was then mixed for 1 minute using a multi-tube vortex mixer. Samples were centrifuged for 15 minutes at 2500 rpm and 4° C. in a Sorvall Super T21 centrifuge (Sorvall Inc., Newtown, Mass.). The supernatant was transferred to a fresh tube containing 20 µL glacial acetic acid. The pellet was re-extracted twice with 2 mL water, 160 µL 0.2 M EDTA and 6 mL acetone and processed as described above. The supernatants from each sample were combined and evaporated to dryness under a stream of nitrogen using a Turbovap Model LV evaporator (Zymark, Hopkinton, Mass.). The residue was reconstituted in 300 μL of acetonitrile/water (1:9), centrifuged for 10 minutes at 14,000 rpm and room temperature using a Model 5415C Eppendorf centrifuge (Brinkmann Instruments, Westbury, N.Y.) and assayed for radioactivity and by HPLC. Selected samples were also analyzed by LC/MS.

The stability of [$^{14}$C]tigecycline was determined in control human serum spiked with [$^{14}$C]tigecycline at 3 μg/mL and incubated at 37° C. This concentration was used because it was near the $C_{max}$ values report for the current study. Aliquots (500 μL) were removed at 0, 1, 4, 8 and 24 hours and placed into fresh vials. EDTA (40 μL of 0.5 M) was added and samples centrifuged at 14,000 rpm and room temperature for 10 min (Eppendorf centrifuge, Model 5415C). Supernatants were transferred to HPLC vials and analyzed by HPLC with radioactivity flow detection.

Additional serum samples were prepared as descried above and extracted. This was done to determine the effects, if any, of the extraction process on the stability of [$^{14}$C]tigecycline. These samples were analyzed by HPLC with radioactivity flow detection, as described in example 6.

Example 4

Urine samples for metabolite profiling were extracted, as discussed below, using a method previously developed and used for rat and dog urine samples. Urine samples that had been collected at various intervals up to 48 hours following the dose of [$^{14}$C]tigecycline were thawed on ice prior to extraction. Aliquots (1 mL) of the individual urine samples were transferred to clean tubes and 0.2 M EDTA, for a final concentration of 40 mM EDTA, was added. The pH remained constant at pH 4.5-5.5. Samples were mixed, centrifuged and the supernatants analyzed for metabolites by HPLC radiochromatography with selected samples also analyzed by LC/MS.

Additional urine from subject #8 was used to isolate metabolite M3a. This urine sample was processed using the same method as described above. The M3a peak was isolated using the HPLC method and collecting the HPLC flow from 2 to 5.5 minutes following sample injection. The pooled fractions were concentrated under a stream of nitrogen using a Turbovap Model LV. The sample was then centrifuged and analyzed by LC/MS.

The stability of [$^{14}$C]tigecycline was determined in control human urine spiked with [$^{14}$C]tigecycline at 5 μg/mL and incubated at 37° C. This concentration was used because it was within the range of [$^{14}$C]tigecycline concentrations in urine for the current study. Aliquots (500 μL) were removed at 0, 1, 4, 8 and 24 hours and placed into fresh vials. These urine samples were processed and analyzed as described for serum in control example 2.

Example 5

Individual fecal sample homogenates, prepared from each fecal sample collected up to 48 hours following the [$^{14}$C]-labeled tigecycline dose, that contained greater than 8000 dpm/g were analyzed for metabolite profiles. The preparation of the fecal sample homogenates is described in detail in the mass balance portion of the study. Briefly, fecal samples were homogenized with 3 to 4 volumes of ice-cold water by weight at ABC Laboratories (Columbia, Mo.) and shipped frozen to the Biotransformation Division of Drug Safety and Metabolism, Wyeth Research, Collegeville, Pa. For the extraction of radioactivity, fecal homogenates were thawed on ice and aliquots (approximately 1 g) transferred to 15 mL tubes. Three volumes of acetone were added and the samples mixed for 1 minute using a multi-tube vortex mixer. Samples were centrifuged for 15 minutes at 2500 rpm and 4° C. in a Sorvall Super T21 centrifuge. The supernatant was transferred to a fresh tube and the pellet re-suspended with 1 mL of water and 80 μL of 0.5 M EDTA, and re-extracted as described above. The pellet was re-extracted in this manner a total of three times and the supernatants pooled. The supernatant was evaporated to dryness under a stream of nitrogen using a Turbovap Model LV. The residue was re-suspended in 500 μL of water and centrifuged for 10 minutes at 14,000 rpm and room temperature using a Model 5415C Eppendorf centrifuge. The supernatant was transferred to an HPLC vial, assayed for radioactivity and for metabolite profiles using HPLC with radioactivity detection. Selected samples were also analyzed by LC/MS.

The stability of [$^{14}$C]tigecycline during the extraction process was determined in control human fecal homogenates spiked with [$^{14}$C]tigecycline at 5 μg/g of homogenate. This concentration was used because it was within the range of [$^{14}$C]tigecycline concentrations in the fecal homogenates from the current study. Samples were extracted and analyzed by HPLC with radioactivity flow detection.

Example 6

HPLC analyses were performed using a Waters 2695 Alliance Separation Module (Waters Corp., Milford, Mass.), a Waters Model 2487 dual wavelength UV absorbance detector, set to monitor 350 nm, and was in-line with a Gilson 215 liquid handler (Gilson, Middleton, Wis.) equipped to collect fractions at 20 second intervals. Fractions were collected into 96-well deep well Luma plates and analyzed using TopCount NXT. The autosampler temperature was set to 4° C. Separation of tigecycline and drug-derived products was achieved on a Phenomenex Luna C18(2) column (150×2.0 mm, 5 μm; Phenomenex, Torrance, Calif.) equipped with a Phenomenex SecurityGuard™ guard cartridge (5 μm) using a linear gradient of two mobile phases, A and B. The column was at an ambient temperature of approximately 20° C. Mobile phase A was 10 mM ammonium acetate in water and mobile phase B was acetonitrile. The flow rate of the mobile phase was 0.2 mL/min and was delivered as shown below.

TABLE 6

HPLC Gradient

| Time (min) | Mobile Phase A (%) | Mobile Phase B (%) |
|---|---|---|
| 0 | 98 | 2 |
| 25 | 90 | 10 |
| 50 | 70 | 30 |
| 60 | 70 | 30 |
| 61 | 98 | 2 |
| 75 | 98 | 2 |

Examples 7-9

Liquid Chromatography/Mass Spectrometry Analysis

The HPLC system used for mass spectrometric analysis was a Waters Alliance model 2695 HPLC system. It was equipped with a built-in autosampler and a model 996 diode array UV detector. Three HPLC conditions were used during LC/MS analysis in this study. LC/MS Condition 1 was used for the majority of sample analyses for metabolite characterization and to isolate metabolite M3a from urine. LC/MS Condition 2 was used on selected samples to increase the retention time of glucuronide metabolites and for a co-chromatography experiment to confirm the identity of metabolites M8 and M9. LC/MS Condition 3 was used to analyze the polar metabolite M3a isolated from human urine.

Example 7

LC/MS Condition 1

The UV detector was set to monitor 340-360 nm. Separations for metabolite characterization were accomplished on a Phenomenex Luna C18(2) column (150×2.0 mm, 5 µm) with a Uniguard C18 guard column (10×2 mm) (ThermoHypersil-Keystone, Bellefonte, Pa.). The flow rate was 0.2 mL/min. During LC/MS sample analysis, up to 2 min of the initial flow was diverted away from the mass spectrometer prior to evaluation of metabolites. Mobile phase A was 10 mM ammonium acetate in water and mobile phase B was acetonitrile. The linear mobile phase gradient is shown below.

TABLE 7

LC/MS HPLC Gradient 1

| Time (min) | Mobile Phase A (%) | Mobile Phase B (%) |
|---|---|---|
| 0 | 98 | 2 |
| 25 | 90 | 10 |
| 50 | 70 | 30 |
| 60 | 70 | 30 |
| 61 | 98 | 2 |
| 75 | 98 | 2 |

Similar HPLC conditions were used to collect fractions containing metabolite M3a. The mobile phases and linear gradient were the same. The column used was a Supelco Discovery C18 column (25 cm×10 mm, 5 µm; Supelco, Bellefonte, Pa.) and the flow rate was 4.7 mL/min. Fractions were collected using a Gilson fraction collector, Model FC204 (Gilson).

Example 8

LC/MS Condition 2

The UV detector was set to monitor 210-400 nm. Separations were accomplished on a Phenomenex Luna C18(2) column (250×2.0 mm, 5 µm) with a Uniguard C18 guard column (10×2 mm) (ThermoHypersil-Keystone). The flow rate was 0.2 mL/min. During LC/MS sample analysis, up to 0.5 min of the initial flow was diverted away from the mass spectrometer prior to evaluation of metabolites. Mobile phase A was 0.02% trifluoroacetic acid in water (v/v) and mobile phase B was 0.02% trifluoroacetic acid in acetonitrile (v/v). The linear mobile phase gradient is shown below.

TABLE 8

LC/MS HPLC Gradient 2

| Time (min) | Mobile Phase A (%) | Mobile Phase B (%) |
|---|---|---|
| 0 | 98 | 2 |
| 15 | 98 | 2 |
| 35 | 90 | 10 |

TABLE 8-continued

LC/MS HPLC Gradient 2

| Time (min) | Mobile Phase A (%) | Mobile Phase B (%) |
|---|---|---|
| 59.5 | 83 | 17 |
| 61 | 15 | 85 |
| 76 | 15 | 85 |
| 77 | 98 | 2 |
| 97 | 98 | 2 |

Example 9

LC/MS Condition 5

Separations were accomplished on a Waters Atlantis HILIC Silica column (150×2.1 mm, 5 µm). The flow rate was 0.2 mL/min. Mobile phase A was 0.02% trifluoroacetic acid in acetonitrile (v/v) and mobile phase B was 0.02% trifluoroacetic acid in water (v/v). The linear mobile phase gradient is shown below.

TABLE 9

LC/MS HPLC Gradient 3

| Time (min) | Mobile Phase A (%) | Mobile Phase B (%) |
|---|---|---|
| 0 | 100 | 0 |
| 10 | 100 | 0 |
| 20 | 66 | 34 |
| 25 | 34 | 66 |
| 40 | 34 | 66 |
| 41 | 100 | 0 |
| 65 | 100 | 0 |

Example 10

Mass Spectrometry

A Micromass Quattro Ultima triple quadrupole mass spectrometer (Waters Corp.) was operated in the positive ionization mode. LC/MS analysis with electrospray ionization (ESI) was conducted using a Z-spray interface. ESI-MS analysis of individual fractions from selected samples was conducted by direct infusion into a nanospray interface. Settings for the mass spectrometer are listed below.

TABLE 10

Micromass Mass Spectrometer Settings

| | |
|---|---|
| ESI spray | 2.75 KV |
| Cone | 44 V |
| Mass resolution of scanning mass analyzer | 0.7 Da ± 0.2 Da width at half height |
| Mass resolution of non-scanning mass analyzer for MS/MS experiments | 1–2 Da width at half height |
| Desolvation gas flow | 850–950 L/hr |
| Cone gas flow | 35–45 L/hr |
| Source block temp. | 80° C. |
| Desolvation gas temp. | 250° C. |
| Collision gas pressure | 0.9–1.1 × $10^{-3}$ mbar |
| Collision offset | −30 eV |

Urine and feces samples were analyzed for tigecycline metabolites by LC/MS/MS analysis for precursors of product ions characteristic of tigecycline. Additionally, potential metabolites of tigecycline were searched for in the LC/MS data based upon results from previous studies in animals and humans.

Serum extracts were analyzed for tigecycline and selected metabolites by LC/MS/MS in the selected reaction monitoring (SRM) mode (LC/SRM) to reduce interference from endogenous components. These experiments were conducted with a dwell time setting of 200 ms. The following tigecycline related components were monitored.

TABLE 11

LC/SRM Analysis of Tigecycline Metabolites

| Compound | Precursor Ion (m/z, Nominal Mass) | Product Ion (m/z, Nominal Mass) |
|---|---|---|
| Tigecycline and its epimer | 586 | 513 |
| Hydroxy tigecycline (M1, M2, M4) and tigecycline N-oxide | 602 | 585 and 472 |
| Tigecycline glucuronides (M6 and M7) | 762 | 569 |
| N-acetyl-9-aminominocycline (M8 and M9, not radiolabeled) | 515 | 498 |
| 9-Aminominocycline (M3, not radiolabeled) | 473 | 456 |

Flo-One analytical software (version 3.65) was utilized to integrate the radioactive peaks for stability analysis and metabolite profiles. Means and standard deviations were calculated using Microsoft Excel® 2000 spreadsheets. The software used for LC/MS data analysis was Micromass MassLynx (version 4.0, Waters Corp.).

Example 11

Materials

Ammonium acetate was purchased from Sigma-Aldrich (St. Louis, Mo.) and Fisher Scientific (Fairlawn, N.J.). HPLC grade water and solvents were purchased from EMD Chemicals (Gibbstown, N.J.).

Methods

Urine Sample Preparation

Urine samples (300 mL) from subjects receiving tigecycline were lyophilized to dryness using a VirTis Sentry 35XL Freezemobile (VirTis Company, Gardiner, N.Y.). The residue was re-suspended in and the containers washed with water. The final volume was 3.5 mL. Samples were centrifuged for 10 minutes at 14,000 rpm and room temperature using a Model 5415C Eppendorf centrifuge (Brinkmann Instruments, Westbury, N.Y.). Then the samples were filtered using Costar Spin X HPLC nylon micro centrifuge filters of 0.2 or 0.45 µm pore size (Corning Incorporated, Corning, N.Y.). Centrifugation for filtration was conducted with an IEC Centra Model GP8R centrifuge (Thermo Electron Corp) operating at 2400 rpm. The resulting crude urine extract was processed by HPLC with fraction collection as described below.

Isolation of Tigecycline Glucuronide by Semi-Preparative HPLC

The urine extract containing tigecycline glucuronide was transferred to 4 mL autosampler vials. The HPLC equipment for metabolite isolation included a Waters Prep 4000 HPLC system, Waters 2767 Sample Manager, Waters Column Fluidics Organizer and Waters 996 diode array UV detector (Waters Corp., Milford, Mass.). Separations were accomplished with a Discovery C18 column (200×10 mm, 5 µm) (Supelco, Bellefonte, Pa.). The UV detector was set to monitor 210 and 450 nm. Mobile phase A was 10 mM ammonium acetate in water and mobile phase B was acetonitrile. The linear mobile phase was delivered as described in Table 12

TABLE 12

| Time (min) | Mobile phase A (%) | Mobile Phase B (%) | Flow rate (mL/min) |
|---|---|---|---|
| 0 | 98 | 2 | 4.7 |
| 25 | 90 | 10 | 4.7 |
| 50 | 70 | 30 | 4.7 |
| 60 | 70 | 30 | 4.7 |
| 61 | 98 | 2 | 4.7 |
| 75 | 98 | 2 | 4.7 |

The HPLC equipment for fraction collection was controlled by Micromass MassLynx software with the FractionLynx module (version 4.0, Waters Corp). Using FractionLynx, collection of metabolite fractions was based on monitoring UV absorbance at 350 nm. After fraction collection, aliquots of selected fractions were analyzed by MS as described below to confirm the presence of tigecycline glucuronide. Fractions containing tigecycline glucuronide were then lyophilized to dryness as described above, reconstituted and analyzed by LC/MS to confirm that tigecycline glucuronide had been isolated.

Liquid Chromatography/Mass Spectrometry

The HPLC system used for tigecycline metabolite analysis included an Agilent Model 1100 HPLC system including a binary pump and diode array UV detector. The HPLC separation conditions were as described above for fraction collection for the metabolite isolation except that the flow rate was 0.2 mL/min and the internal diameter of the HPLC column was 2.1 mm. Analysis of metabolite fractions prior to lyophillization was conducted without the HPLC column by direct infusion of aliquots of fractions into the mass spectrometer.

The mass spectrometer used for metabolite characterization was a Finnigan LCQ ion trap mass spectrometer (Thermo Electron Corp., San Jose, Calif.). It was equipped with an electrospray ionization (ESI) interface and operated in the positive ionization mode. LC/MS data were analyzed with Xcalibur software (version 1.3, Thermo Electron Corp.) software.

Tigecycline Glucuronide Mass Spectra

Figure 23A:
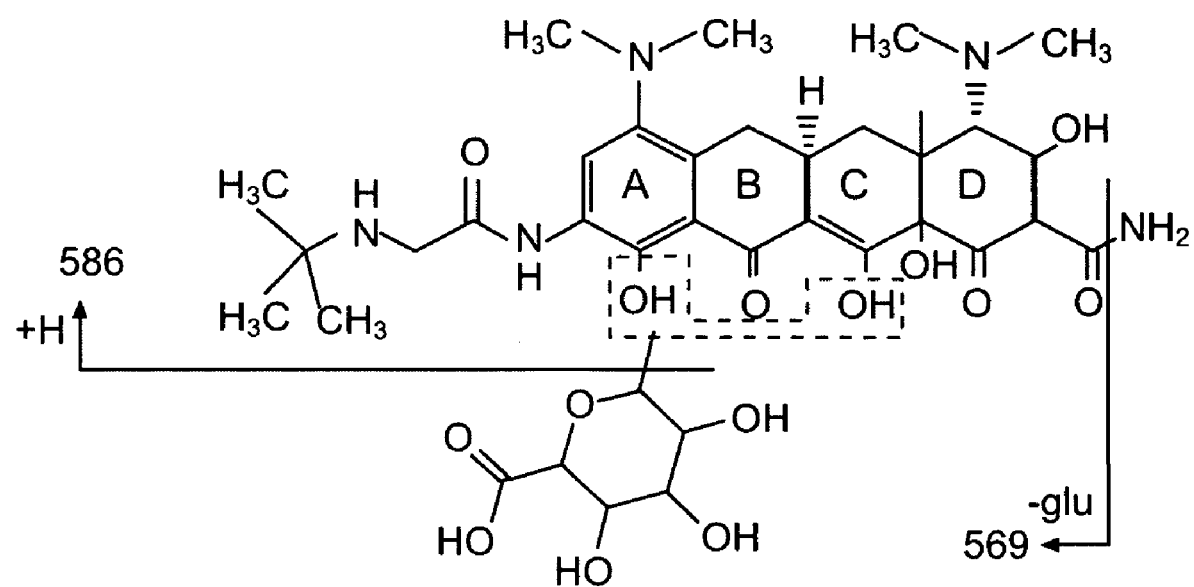
FIG. 23A shows the product ions for tigecycline glucuronide from a direct infusion of a HPLC fraction collected from human urine.
Figure 23B:
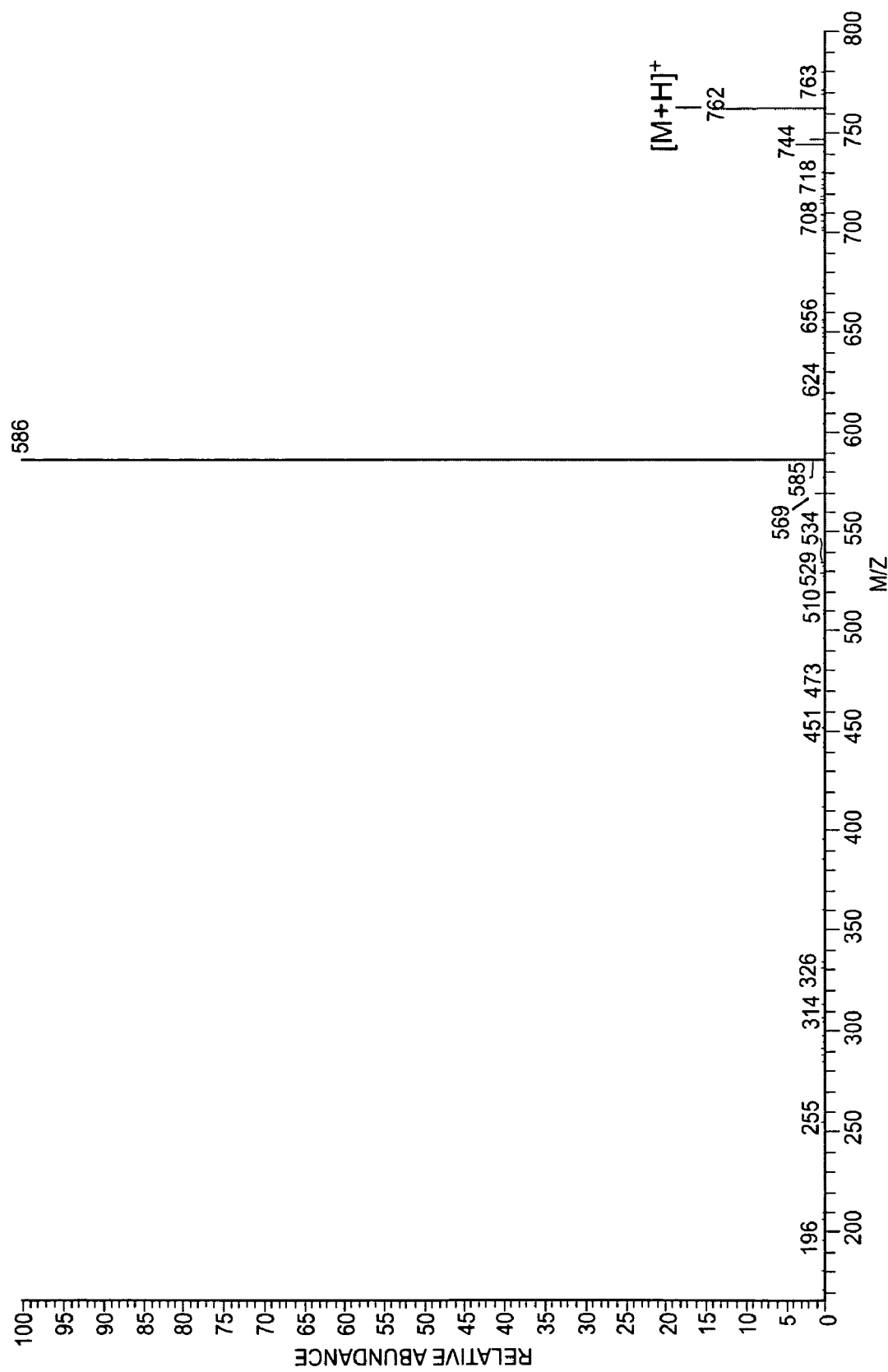
FIG. 23B is a mass spectrum for tigecycline glucuronide showing the product ions of m/z 762 mass spectrum from a direct infusion of a HPLC fraction collected from human urine.
Figures 24A, 24B:
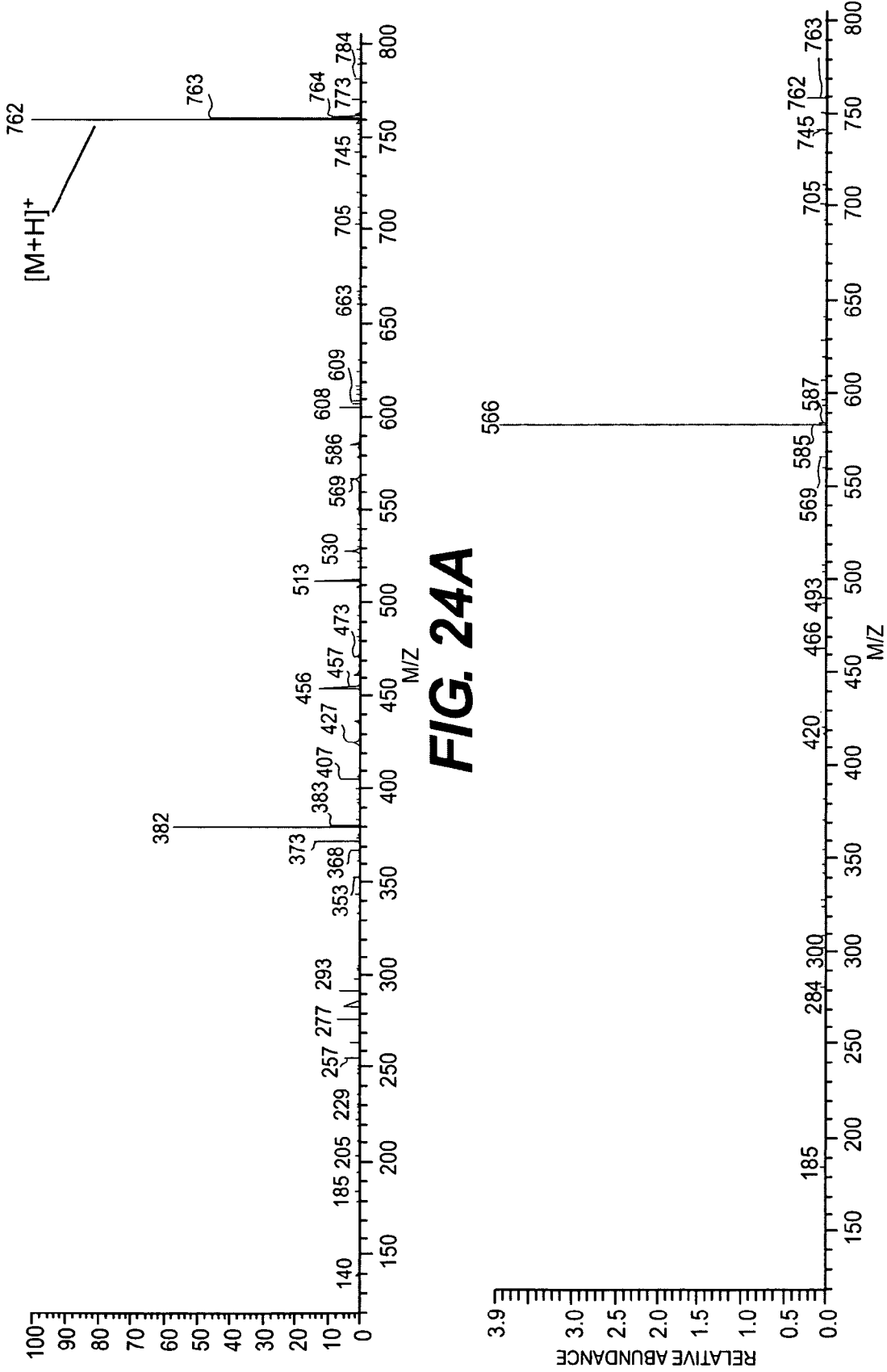
FIG. 24A is a LC/MS Spectrum of tigecycline glucuronide from LC/MS analysis of tigecycline glucuronide isolated from human urine.
FIG. 24B is a MS2 of m/z 762 mass spectrum of tigecycline glucuronide from LC/MS analysis of tigecycline glucuronide isolated from human urine.
Figure 24C:
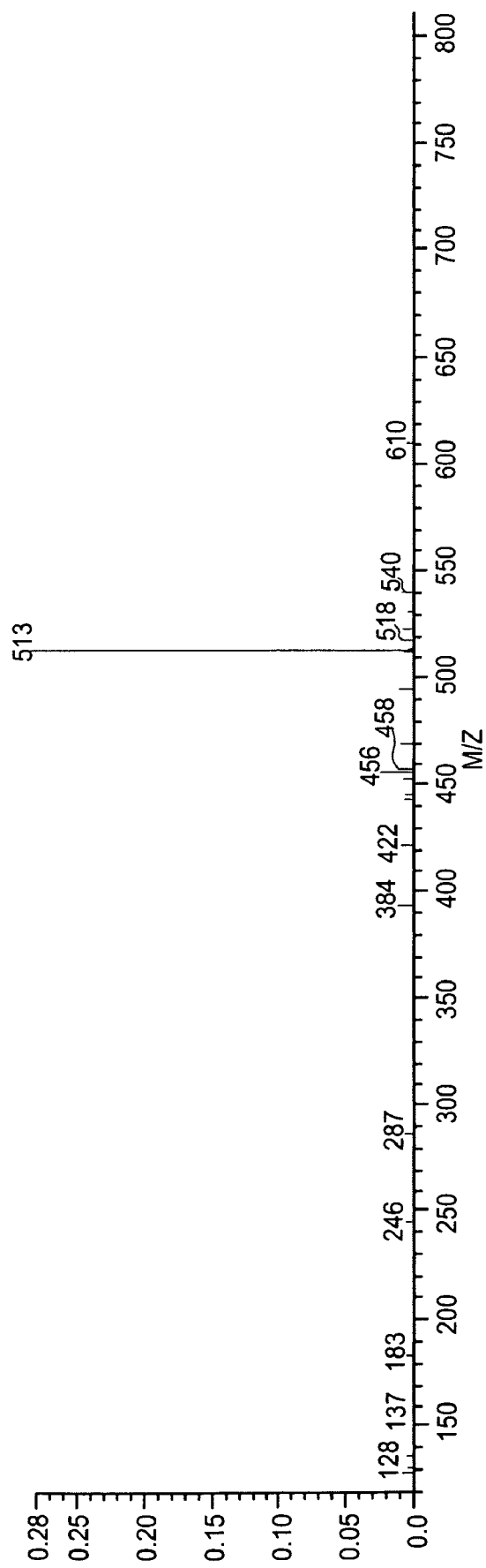
FIG. 24C is a MS3 m/z 762à586à mass spectrum of tigecycline glucuronide from LC/MS analysis of tigecycline glucuronide isolated from human urine.
Figure 24D:
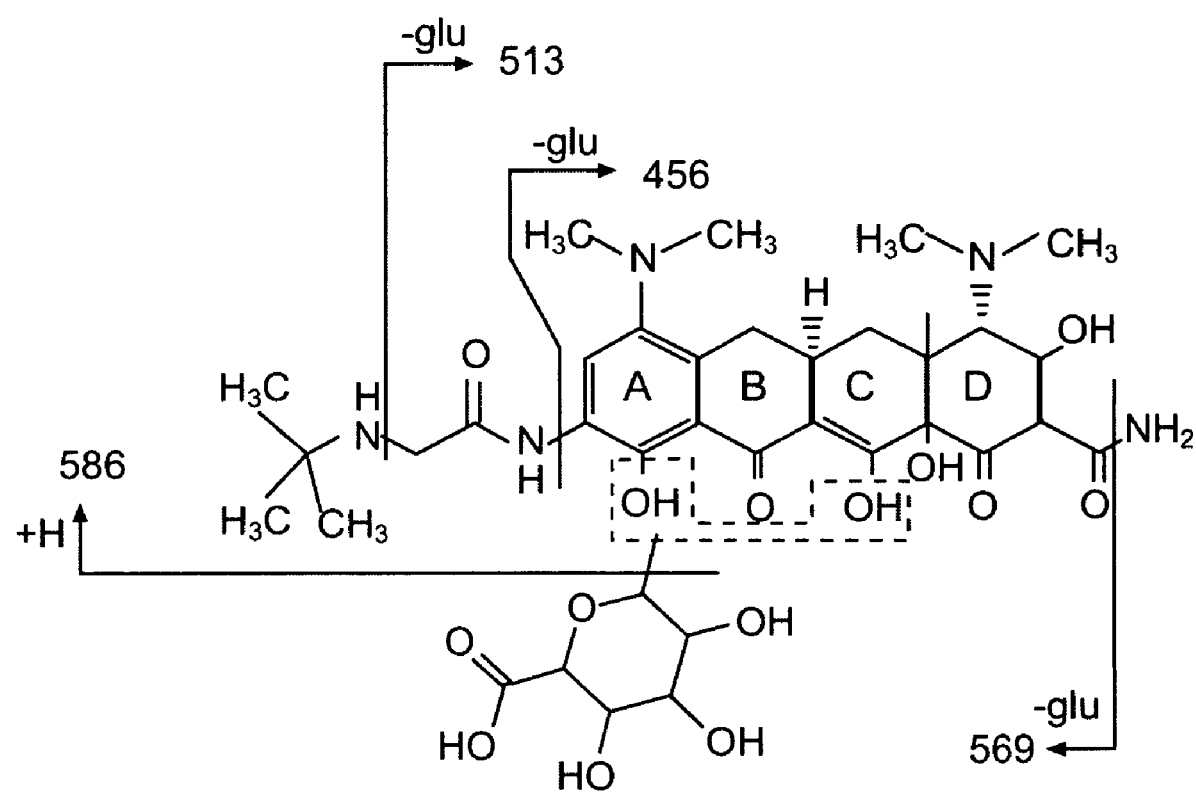
FIG. 24D shows the product ions for tigecycline glucuronide from LC/MS analysis of tigecycline glucuronide isolated from human urine.

Tigecycline glucuronide collected from HPLC fractionation of human urine. The [M+H]$^+$ for tigecycline glucuronide was observed at m/z 762, which was 176 Da larger than tigecycline. The product ions of m/z 762 mass spectrum for tigecycline glucuronide is shown in FIGS. 23A and 23B. Neutral loss of 176 Da generated m/z 586, also the [M+H]$^+$ for tigecycline, which indicated a glucuronide of tigecycline. LC/MS analysis of tigecycline glucuronide fractions after lyophillization and reconstitution provided the MS and MSn spectra shown in FIGS. 24A-24D. These mass spectral data were also indicative of tigecycline glucuronide.

This Example demonstrated that tigecycline glucuronide can be isolated from the urine of human subjects administered with IV doses of tigecycline.

Example 12

This Example investigated the possibility of the two metabolic pathways tigecycline metabolism, glucuronidation of the parent compound and N-acetylation of 9-aminominocycline, being present in mice and rabbits following a single intravenous administration of tigecycline. Serum samples from each species were collected and analyzed by LC/MS to determine the presence or absence of these metabolites and, when possible, to estimate their concentration. Urine samples from mice were also collected to investigate the presence of tigecycline metabolites.

Materials

The tigecycline used for the preparation of the intravenous dosing solutions for mice and rabbits (lot A96559, with a purity of 100%), tigecycline reference standard (batch RS 738-4, with a purity of 98.4%), deuterated (t-butyl-d9) tigecycline (WFQ0159; used as an internal standard), 9-aminominocycline reference standard and N-acetyl-9-aminominocycline were received from Wyeth Research, Pearl River, N.Y.

Control rabbit and mouse serum were obtained from Bioreclamation Inc. (Hicksville, N.Y.). Acetonitrile and methanol were obtained from EMD Chemicals, Inc. (Gibbstown, N.J.). Ethylenediaminetetraacetic acid (EDTA) was obtained from Sigma Chemical Co. (St. Louis, Mo.). Ammonium acetate was obtained from Mallinckrodt Baker (Phillipsburg, N.J.). All reagents were analytical grade or better.

Mouse and Rabbit Study Design

Animals

Fifteen male CD-1 mice, with an average weight of 31.3 g at the time of dosing, were used. Animals were given food and water ad libitum. Mice in the 0.5 and 2 hour blood collection groups were housed in standard cages, while those in the 4 hour blood collection group were housed in metabolism cages for the collection of urine. Mice were dosed by the Bioresources Department at Wyeth Research, Collegeville, Pa.

Three female New Zealand White rabbits, weighing between 3.9 and 4.3 kg at the time of dosing, were used. Animals were given food and water ad libitum. Animals were individually housed in standard cages. Rabbits were dosed at Wyeth Research, Chazy, N.Y. and samples shipped frozen to the Wyeth Research Biotransformation Department, Collegeville, Pa.

Dosing

For mice and rabbits, the intravenous dosing solutions was prepared by dissolving 50 mg of tigecycline in 5.0 mL of 0.9% sterile saline solution to make a working stock solution. The working stock solution was diluted with 0.9% sterile saline solution to 0.5 mg/mL for mice and 4 mg/mL for rabbits. The mouse dose (5 mg/kg, 10 mL/kg) was administered as a bolus injection via the tail vein. The rabbit dose (4 mg/kg, 1 mL/kg) was administered as a bolus injection via the marginal vein of the ear.

Sample Collection

For mice (n=5/time point), blood (approximately 0.7 mL) was collected by cardiac puncture at 0.5, 2 and 4 hours following administration of tigecycline. For rabbits, blood (approximately 7 mL) was collected via the ear vein at 0.5, 2 and 6 hours following the tigecycline dose. Serum was separated following clot formation at room temperature and centrifugation for 15 minutes at 4° C. and 3000 rpm. The serum was transferred to a fresh tube and was stored at approximately −70° C. until analysis as described below under "Serum Sample Preparation for LC/MS Analysis. In addition, urine was collected from mice in the 4 hour blood collection group and was stored at approximately −70° C. until analysis, as described below under "Urine Sample Preparation for LC/MS Analysis."

Estimation of Purity of N-acetyl-9-aminominocycline, M9

The purity of the N-acetyl-9-aminominocycline, M9 used in this study was estimated by HPLC analysis with UV detection, as described below under "Liquid Chromatography/Mass Spectrometry Analysis." M9 purity was determined based on UV chromatographic peak area of M9 as a percentage of the total UV chromatographic peak area of M9 related components in a 100 ng/µL sample. It was assumed that M9 and the other related components had the same UV molar absorptivity and that no other M9 related material was present. Individual components present in a relative amount less than the 37.6 min peak (2.8% of total) were considered trace components and were not included in this estimate of purity. In the synthetic material, only M9 and its epimer were characterized by LC/MS; the other degradants were not characterized. The actual concentration of M9 in each standard curve sample was adjusted based on the estimate of M9 purity obtained by this method.

Urine Sample Preparation for LC/MS Analysis

Mouse urine was thawed and an aliquot (1 mL) transferred to a fresh tube. The sample was centrifuged at 14,000 rpm and room temperature for 10 minutes using a Model 5415C Eppendorf centrifuge (Brinkmann Instruments, Westbury, N.Y.) to remove any particulates. The sample was then transferred to a fresh tube and was analyzed by LC/MS, as described below under "Liquid Chromatography/Mass Spectrometry Analysis.".

Serum Sample Preparation for LC/MS Analysis

Mouse and rabbit serum samples were pooled at each collection time and analyzed for tigecycline, its epimer, tigecycline glucuronide (M7 and its epimer M6), 9-aminominocycline (M3) and N-acetyl-9-aminominocycline (M9 and its epimer M8). Aliquots of serum (500 µL) were transferred to new tubes and deuterated tigecycline (30 ng/mL final concentration) was added as an internal standard (quantitative analysis only). EDTA (40 µL of 0.5 M EDTA) was added to each sample and the samples vortex mixed. Acetonitrile (500 µL) was added to each sample, samples were vortex mixed and denatured protein separated by centrifugation at 14,000 rpm and room temperature for 10 minutes using a Model 5415C Eppendorf centrifuge (Brinkmann Instruments). The supernatant was transferred to a fresh tube and the solvent evaporated under a stream of nitrogen using a Turbovap Model LV evaporator (Caliper Life Sciences, Hopkinton, Mass.). The remaining aqueous solution was analyzed by LC/MS, as described below under "Liquid Chromatography/Mass Spectrometry Analysis." Some rabbit serum samples were diluted 5- or 50-fold with control rabbit serum to ensure that the analyte response would be within the range of the standard curves.

Standard curves for tigecycline, M3 and M9 were prepared in rabbit serum. Standard curves were prepared by adding the internal standard and synthetic tigecycline and metabolite standards to control plasma. Standard curve samples were prepared with tigecycline concentrations of 0, 10, 20, 50, 100, 200, 500 and 1000 ng/mL, with the linear range being 5 to 200 ng/mL. For 9-aminominocycline (M3), the concentrations were 0, 1, 5, 10, 20, 50, 100 and 200 ng/mL, with the linear range being 10 to 200 ng/mL. For N-acetyl-9-aminominocycline (M9), the concentrations were 1.6, 3.2, 6.4, 16, 32, 64 and 96 ng/mL, with the linear range being from 3.2 to 96 ng/mL. These samples were processed and analyzed as described above.

An aliquot of a human urine sample that contained M7 (tigecycline glucuronide) was added to the pooled 2 hour rabbit serum extract to determined if the glucuronide observed in rabbits was the same as that observed in humans. This sample was analyzed by LC/MS, as described below under "Liquid Chromatography/Mass Spectrometry Analysis."

Liquid Chromatography/Mass Spectrometry Analysis

The HPLC system used for mass spectrometric analysis was a Waters Alliance Model 2695 HPLC system (Waters Corp., Milford, Mass.). It was equipped with a built-in autosampler and a Model 996 diode array UV detector. The UV detector was set to monitor 210-400 nm. Separations for metabolite characterization were accomplished on a Phenomenex Luna C18(2) column (150×2.1 mm, 5 µm) (Phenomenex, Torrance, Calif.) equipped with a Keystone Uniguard C18 guard column (10×2.1 mm) (Thermo Electron Corp., Bellefonte, Pa.). The column temperature was 25° C. The flow rate was 0.2 mL/min. Mobile phase A was 10 mM ammonium acetate in water and mobile phase B was acetonitrile. Two linear mobile phase gradients were used and are shown in Tables 2.2.5-1 and 2.2.5-2. Gradient 1 was used for metabolite identification (qualitative analysis). Gradient 2 was used for semi-quantitative analysis of rabbit serum samples. During LC/MS sample analysis, up to 10 min of the initial flow was diverted away from the mass spectrometer prior to evaluation of metabolites. The LC/MS HPLC data for Gradient 1 and Gradient 2 is shown in Tables 13 and 14.

TABLE 13

| Time (min) | A (%) | B (%) |
|---|---|---|
| 0 | 98 | 2 |
| 25 | 90 | 10 |
| 50 | 70 | 30 |
| 60 | 70 | 30 |
| 61 | 98 | 2 |
| 75 | 98 | 2 |

TABLE 14

| Time (min) | A (%) | B (%) |
|---|---|---|
| 0 | 98 | 2 |
| 1 | 98 | 2 |
| 5 | 90 | 10 |
| 18 | 70 | 30 |
| 22 | 70 | 30 |
| 22.1 | 98 | 2 |
| 30 | 98 | 2 |

The mass spectrometer used was a Micromass Quattro Ultima triple quadrupole mass spectrometer (Waters Corp.). It was equipped with an electrospray interface and operated in the positive ionization mode. Settings for the mass spectrometer are listed in Table 15.

TABLE 15

| Micromass Mass Spectrometer Settings | |
|---|---|
| ESI spray | 2.5 kV |
| Cone | 50 V |
| Mass resolution of scanning mass analyzer | 0.7 Da ± 0.2 Da width at half height |
| Mass resolution of non-scanning mass analyzer for MS/MS experiments | 1–2 Da width at half height |
| Desolvation gas flow | 950–1100 L/hr |
| Cone gas flow | 40–60 L/hr |
| Source block temp. | 80° C. |
| Desolvation gas temp. | 250° C. |
| Collision gas pressure | 1.0–1.2 × $10^{-3}$ mbar |
| Collision offset | −30 eV |

LC/MS/MS analysis in the selected reaction monitoring (SRM) mode (LC/SRM) was also conducted on serum extracts to screen samples for tigecycline metabolites and to obtain estimated concentrations of tigecycline metabolites. These experiments were conducted with a dwell time setting of 200 ms. SRM analysis conditions are summarized in Table 16. Internal standard was not used or monitored for qualitative analyses.

TABLE 16

| SRM Analysis Conditions for Tigecycline and its Metabolites | | |
|---|---|---|
| Compound | Precursor ion (m/z, nominal mass) | Product ion (m/z, nominal mass) |
| Tigecycline and its epimer | 586 | 513 |
| 9-Aminominocycline | 473 | 456 |
| N-Acetyl-9-aminominocycline | 515 | 498 |
| $^2H_9$-Tigecycline (internal standard) | 595 | 514 |
| Tigecycline glucuronide and its epimer | 762 | 569 |

Data Analyses and Calculations

Micromass MassLynx (version 4.0, Waters Corp.) was used for analysis of LC/MS data. The concentrations of tigecycline, 9-aminominocycline (M3) and N-acetyl-9-aminominocycline (M9) in serum were calculated based on the analyte to internal standard peak area ratios in the samples as compared to the standard curves generated in rabbit serum.

Purity of N-Acetyl-9-aminominocycline (M9) Synthetic Standard

Figure 25:
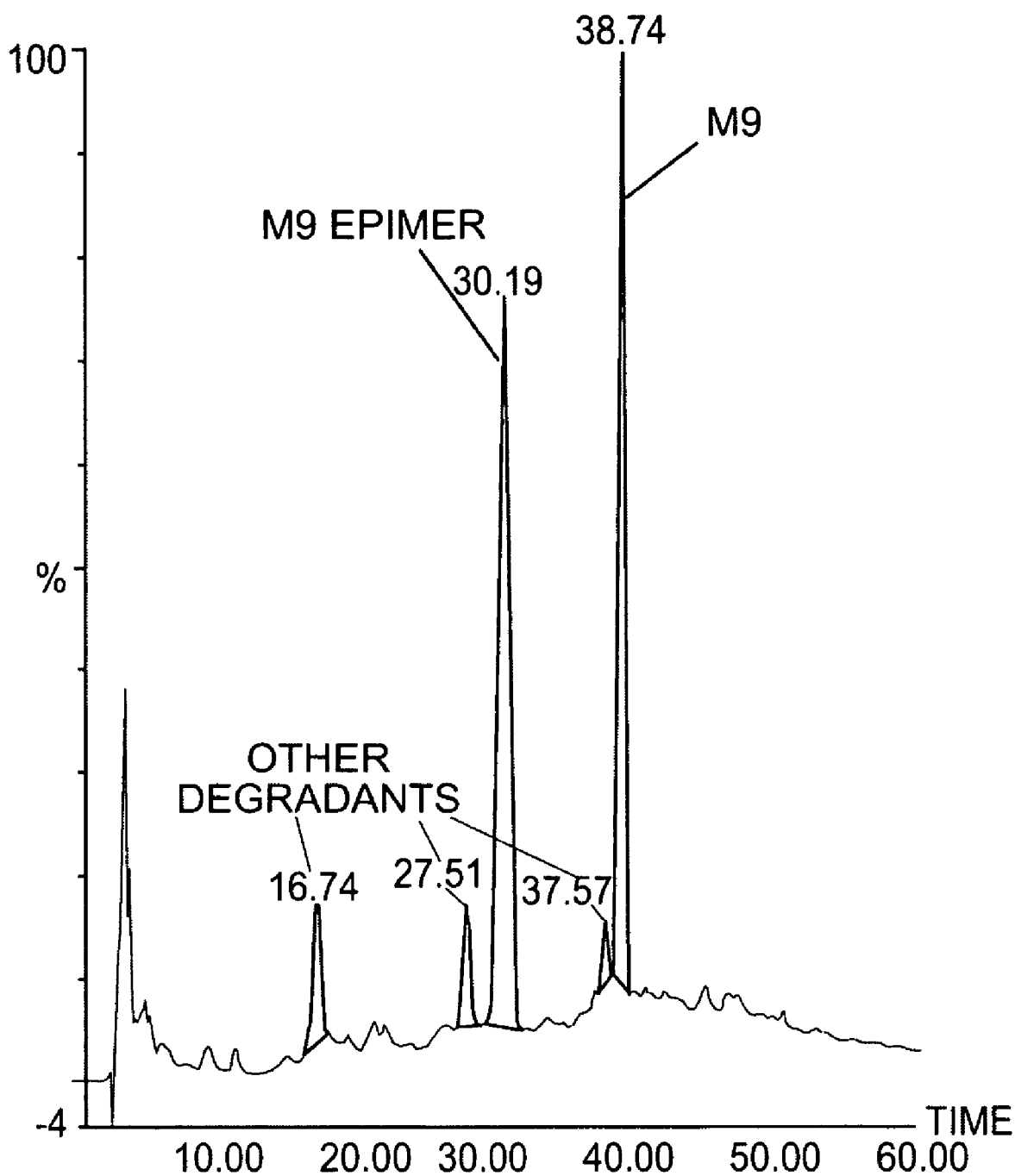
FIG. 25 is a UV chromatogram from HPLC analysis of synthetic N-Acetyl-9-aminominocycline (M9)

The UV chromatogram from HPLC analysis of synthetic N-Acetyl-9-aminominocycline (M9) is shown in FIG. 25. The UV chromatographic peak areas of M9 and its degradants are shown in Table 17.

TABLE 17

| Estimation of Purity of N-Acetyl-9-aminominocycline (M9) | | | |
|---|---|---|---|
| Component | Time (min) | UV Peak Area | Percent of Total |
| Uncharacterized degradant | 16.7 | 8998 | 8.1 |
| Uncharacterized degradant | 27.5 | 6435 | 5.8 |
| M9 epimer | 30.2 | 56821 | 51 |
| Uncharacterized degradant | 37.6 | 3178 | 2.8 |
| M9 | 38.7 | 36321 | 32 |

M9 epimer was the most abundant compound related component, which accounted for approximately 51% of the synthetic N-Acetyl-9-aminominocycline. The estimated purity of N-Acetyl-9-aminominocycline was 32%.

Metabolites in Mouse Serum and Urine and Rabbit Serum

In mouse serum, tigecycline, the epimer of tigecycline, 9-aminominocyine (M3) and tigecycline glucuronide (M7 and its epimer M6) were observed by LC/MS analysis. The concentrations of these components in mouse serum were not investigated. No N-acetyl-9-aminominocycline was observed in mouse serum. The same tigecycline related components were observed in mouse urine.

In rabbit serum, tigecycline, the epimer of tigecycline, 9-aminominocyine (M3), tigecycline glucuronide (M7 and its epimer M6) and N-acetyl-9aminominocycline (M9) were observed by LC/MS analysis. The characterization of the tigecycline glucuronide in rabbits as the same one observed in humans was supported by co-chromatography experiments performed using human urine known to contain M7 (data not shown). The estimated concentrations of tigecycline in rabbit serum decreased from 2020 ng/mL at 1 hour to 1040 ng/mL at 2 hours and 287 ng/mL at 6 hours (Table 18). The concentrations of M3 also decreased with time and were 545, 312 and 90.2 ng/mL at 0.5, 2 and 6 hours, respectively. However, M9 concentrations increased with time, from 5.5 ng/mL at 0.5 hours to 8.1 and 20 ng/mL at 2 and 6 hours, respectively.

TABLE 18

Estimated Concentrations of Tigecycline, 9-Aminominocycline (M3) and N-Acetyl-9-aminominocycline (M9) in Serum Samples from Female New Zealand White Rabbits Following Intravenous Administration of Tigecycline

| Time (hr) | Concentration (ng/mL) | | |
|---|---|---|---|
| | M3 | M9 | Tigecycline |
| 0.5 | 545 | 5.5 | 2020 |
| 2 | 312 | 8.1 | 1040 |
| 6 | 90.2 | 20 | 287 |

Metabolite Characterization by Liquid Chromatography/Mass Spectrometry

LC/MS analysis was conducted on extracts of serum and from CD-1 mice and rabbits, and on urine from CD-1 mice. A summary of the tigecycline related compounds observed in these samples is presented in Table 19. The mass spectral data for tigecycline and its metabolites are discussed below.

TABLE 19

Tigecycline Metabolites Identified in CD-1 Mouse Serum and Urine and Rabbit Serum Samples

| Peak | $t_R$ (min)[a] | [M + H]$^+$ | Site of Metabolism[b] | Metabolite | Species[c] |
|---|---|---|---|---|---|
| M3 | 40.4 | 473 | TBAAA group | 9-Aminominocycline | R-S, M-S, M-U |
| M6 | 32.4 | 762 | Hydroxy group on ring A or B | Tigecycline glucuronide epimer | R-S, M-S, M-U |
| M7 | 35.1 | 762 | Hydroxy group on ring A or B | Tigecycline glucuronide | R-S, M-S, M-U |
| M9 | 40.2 | 515 | TBAAA group | N-Acetyl-9-aminominocycline | R-S |
| | 43.2 | 586 | Ring D | Tigecycline epimer | R-S, M-S, M-U |
| | 46.0 | 586 | None | Tigecycline | R-S, M-S, M-U |

Figure 26A:
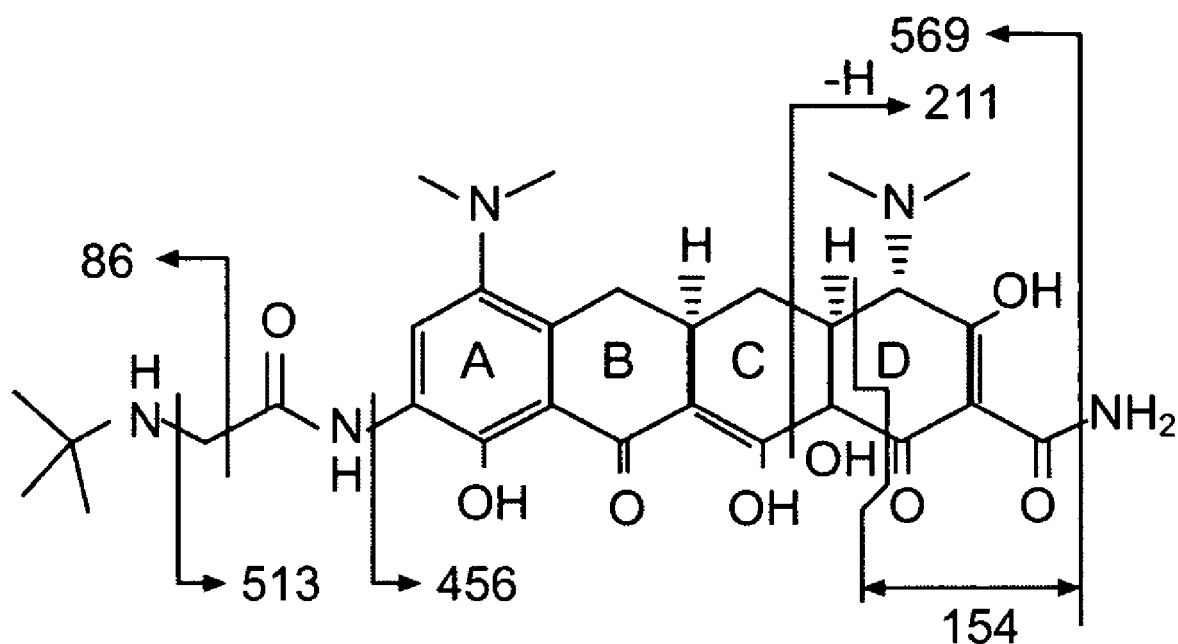
FIG. 26A is a proposed fragmentation scheme of a MS/MS spectrum obtained from collision activated dissociation of m/z 586 of tigecycline.
Figure 26B:
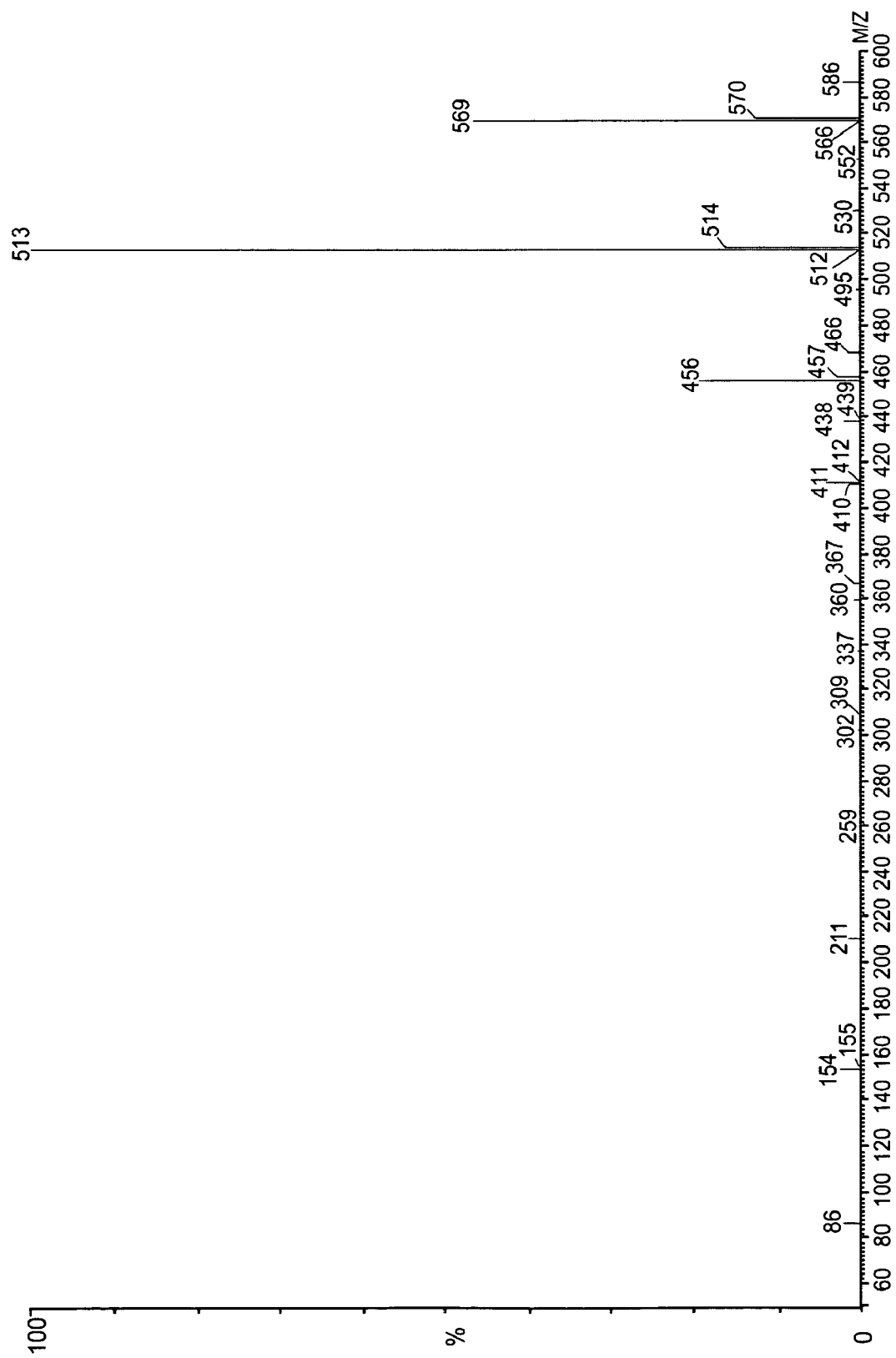
FIG. 26B is a MS/MS spectrum obtained from collision activated dissociation of m/z 586 of tigecycline

[a]Retention time obtained from LC/MS data files UL_063005_0006 and UL_070105_0005
[b]TBAAA = t-butylaminoacetylamino
[c]M, mouse; R, rabbit; S, serum; U, urine Tigecycline Tigecycline was observed in mouse serum and urine, and in rabbit serum. The mass spectral characteristics of tigecycline authentic standard were examined for comparison with metabolites. In the LC/MS spectrum of tigecycline, a protonated molecular ion, [M+H]$^+$, was observed at m/z 586. The MS/MS spectrum obtained from collision activated dissociation of m/z 586 of tigecycline is shown in FIG. 26A and the proposed fragmentation scheme is shown in FIG. 26B. The proposed fragmentation scheme was consistent with the scheme proposed by Kamel and coworkers for related tetracycline antibiotics (A. M. Kamel et al., Mass spectral characterization of tetracyclines by electrospray ionization, H/D exchange, and multiple stage mass spectrometry. J Am Soc Mass Spectrom, 13:543-557, 2002). Loss of NH$_3$ from m/z 586 generated m/z 569. The product ion at m/z 513 represented loss of the t-butylamino group from the t-butylaminoacetylamino (TBAAA) side chain. Loss of the entire TBAAA side chain yielded m/z 456. The product ions at m/z 211 and 154 originated from the D ring of the tetracycline ring system as indicated in the fragmentation scheme of FIG. 26B. The m/z 86 ion represented the t-butylaminomethylene group.

Tigecycline Epimer

Figure 27A:
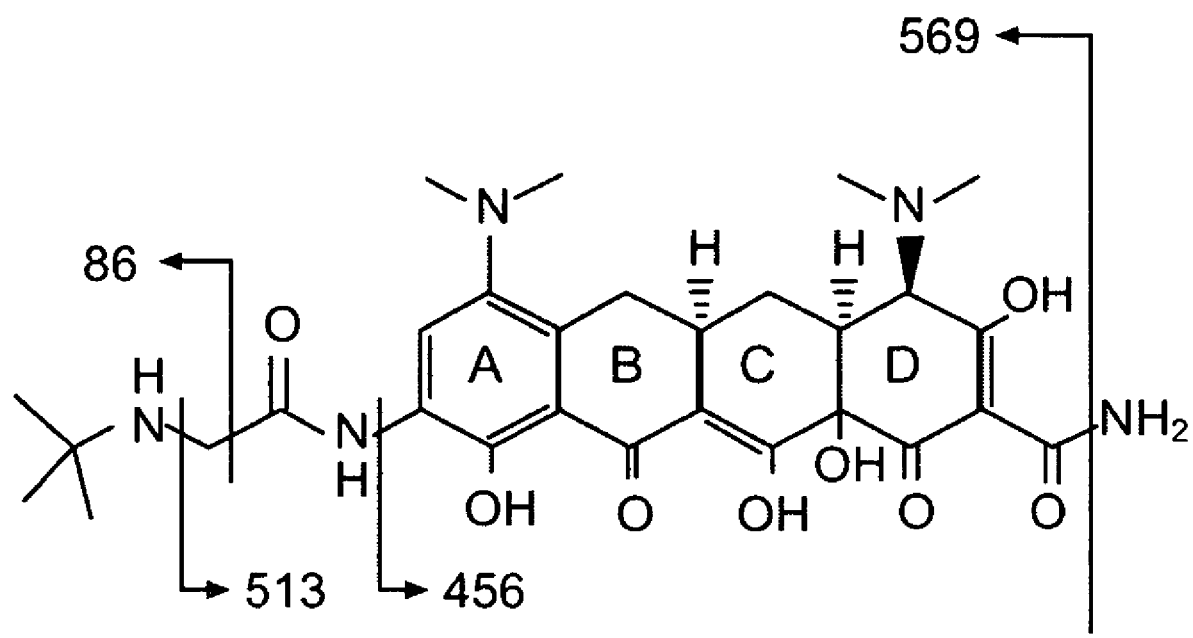
FIG. 27A shows the product ions of a m/z 586 mass spectrum for the epimer of tigecycline.
Figure 27B:
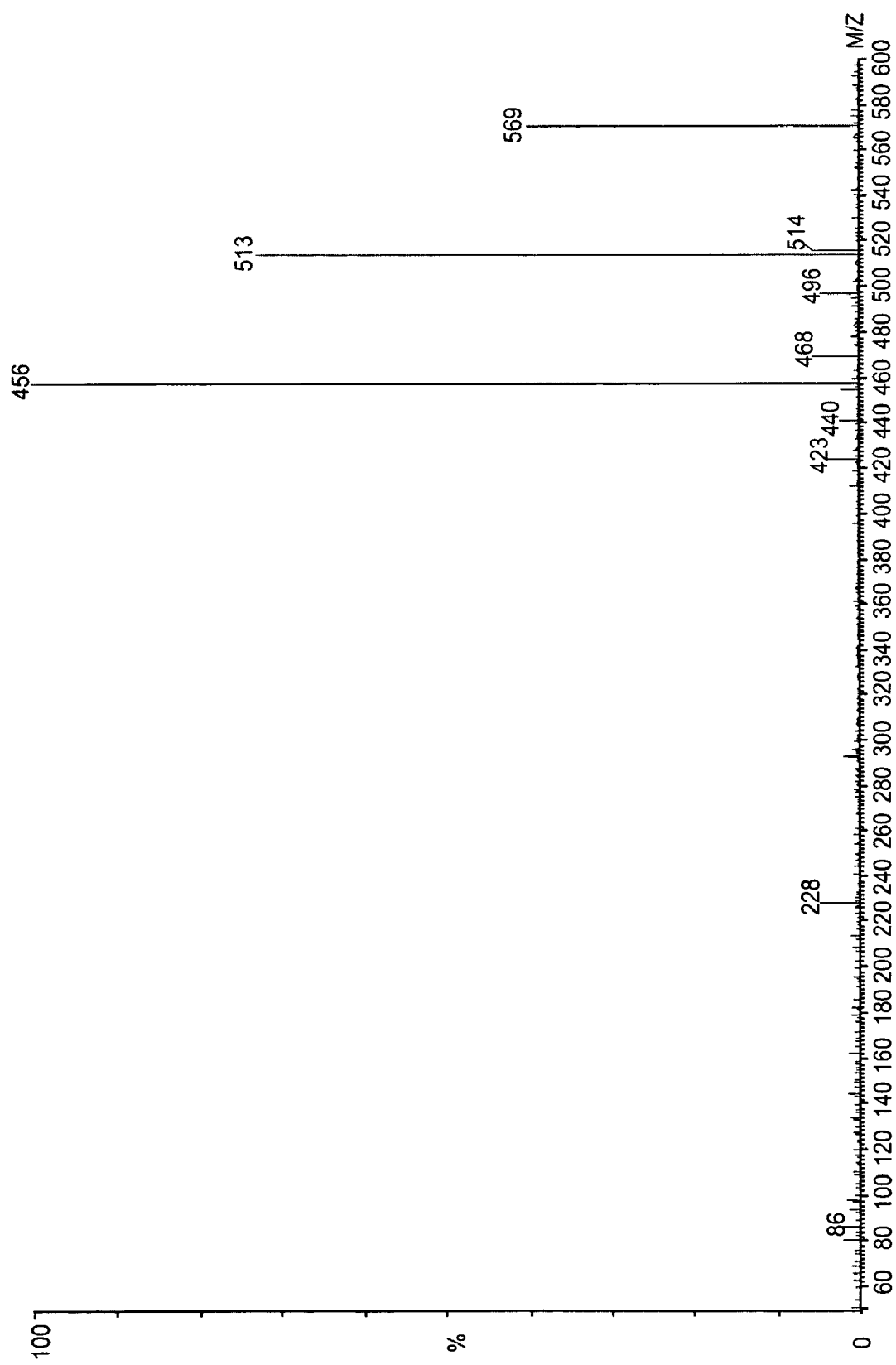
FIG. 27B is a m/z 586 mass spectrum for the epimer of tigecycline.

The epimer of tigecycline was observed in mouse serum and urine, and in rabbit serum, which generated a [M+H]$^+$ at m/z 586. The product ions of m/z 586 mass spectrum, shown in FIGS. 27A and 27B, includes m/z 569, 513, 456 and 86 that were also present for tigecycline. Identification as the epimer was made based on its relative retention time being shorter than that of tigecycline.

Metabolite M3

Figure 28A:
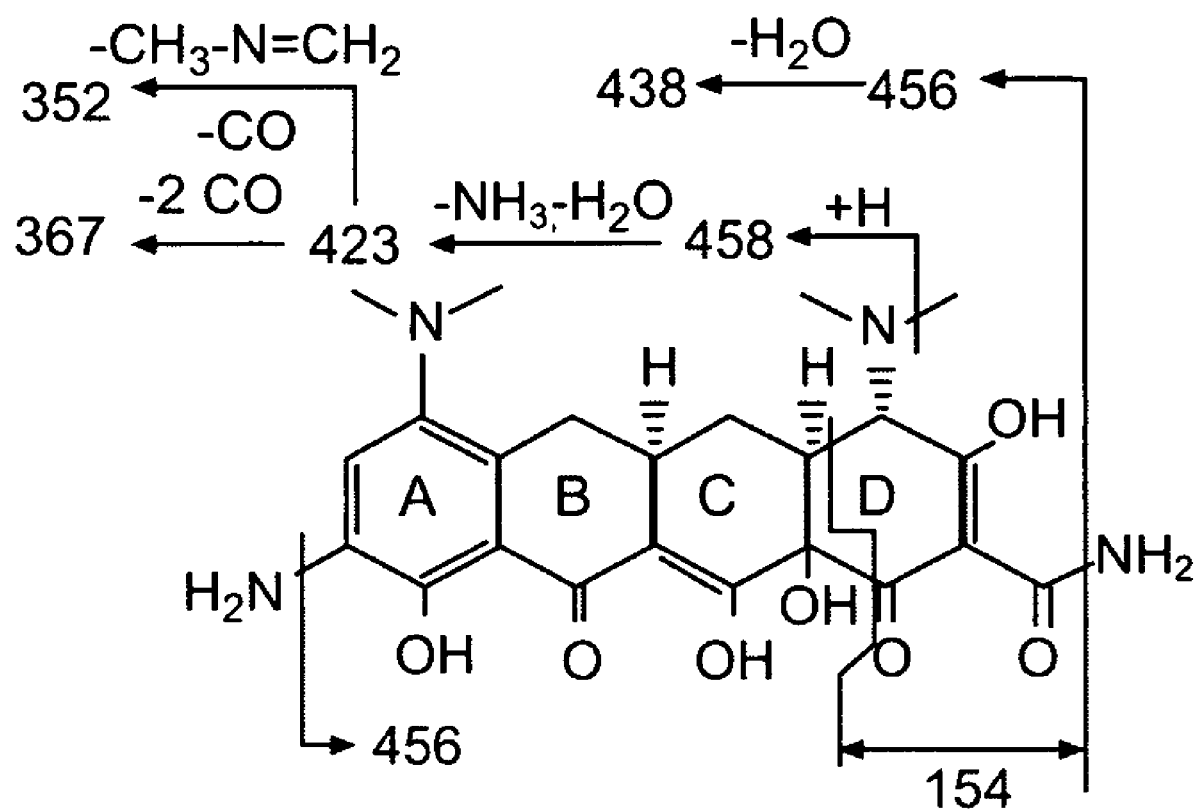
FIG. 28A shows the product ions of m/z 473 mass spectrum for M3.
Figure 28B:
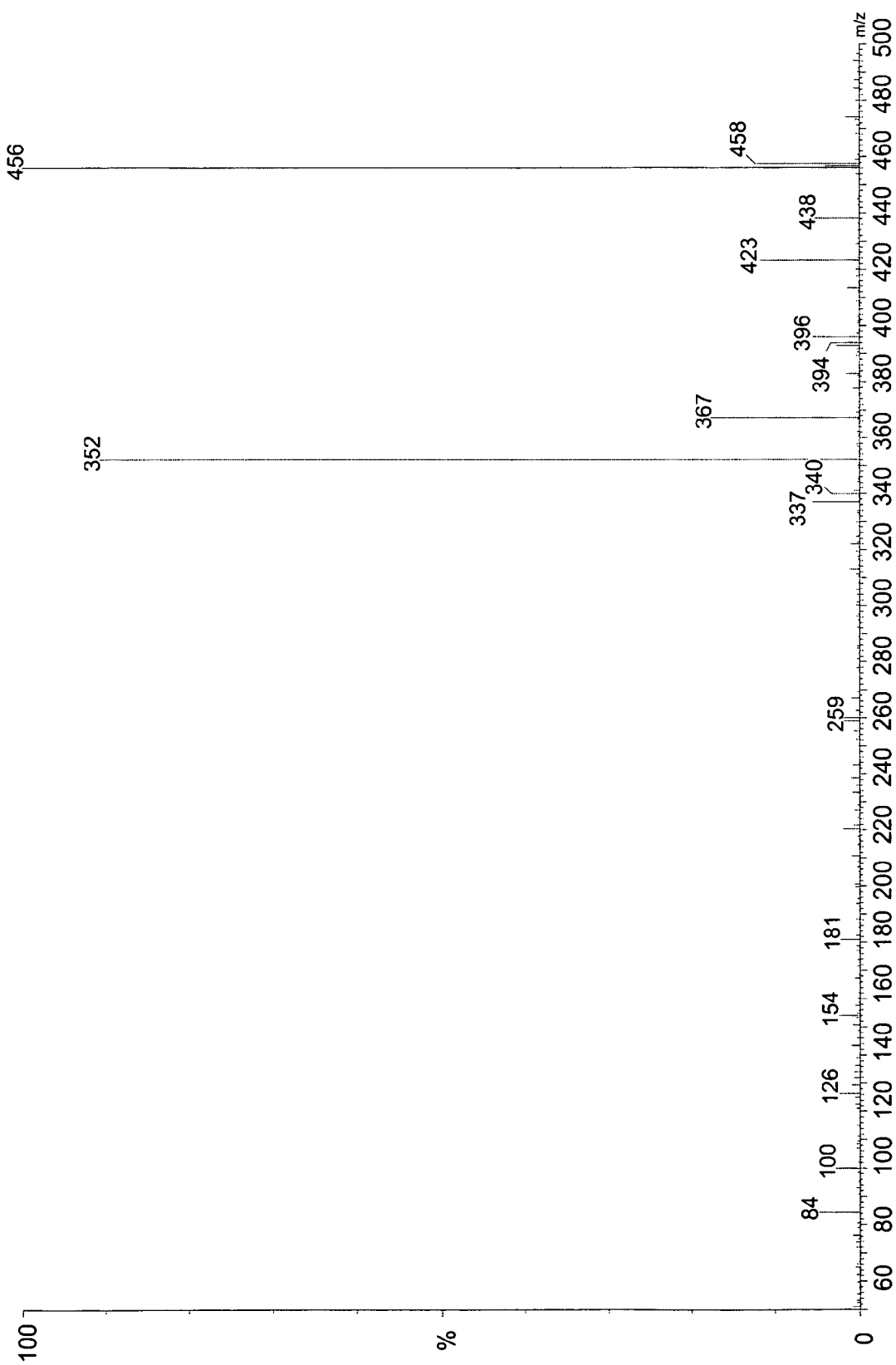
FIG. 28B is a m/z 473 mass spectrum for M3.

Metabolite M3 was observed in mouse serum and urine, and in rabbit serum. The [M+H]$^+$ for metabolite M3 was observed at m/z 473. The product ions of m/z 473 mass spectrum for M3 is shown in FIGS. 28A and 28B. Product ions of m/z 473 mass spectrum included m/z 458 and 456 generated from losses of a methyl group and NH$_3$, respectively. The product ion at m/z 154 was also observed for tigecycline, which indicated an unchanged D ring. Loss of H$_2$O and NH$_3$ from m/z 458 yielded m/z 423. Subsequent loss of two CO molecules yielded m/z 367. Loss of both CO and CH$_3$—N═CH$_2$ generated m/z 352. This fragmentation behavior was consistent with minocycline related compounds (A. M. Kamel et al., Mass spectral characterization of tetracyclines by electrospray ionization, H/D exchange, and multiple stage mass spectrometry. J Am Soc Mass Spectrom, 13:543-557, 2002) and with identification of M3 as 9-aminocycline. Confirmation was obtained by matching HPLC retention time and MS/MS spectral data for M3 with that of synthetic 9-Aminominocycline (data not shown).

Metabolites M6 and M7

Figure 29A:
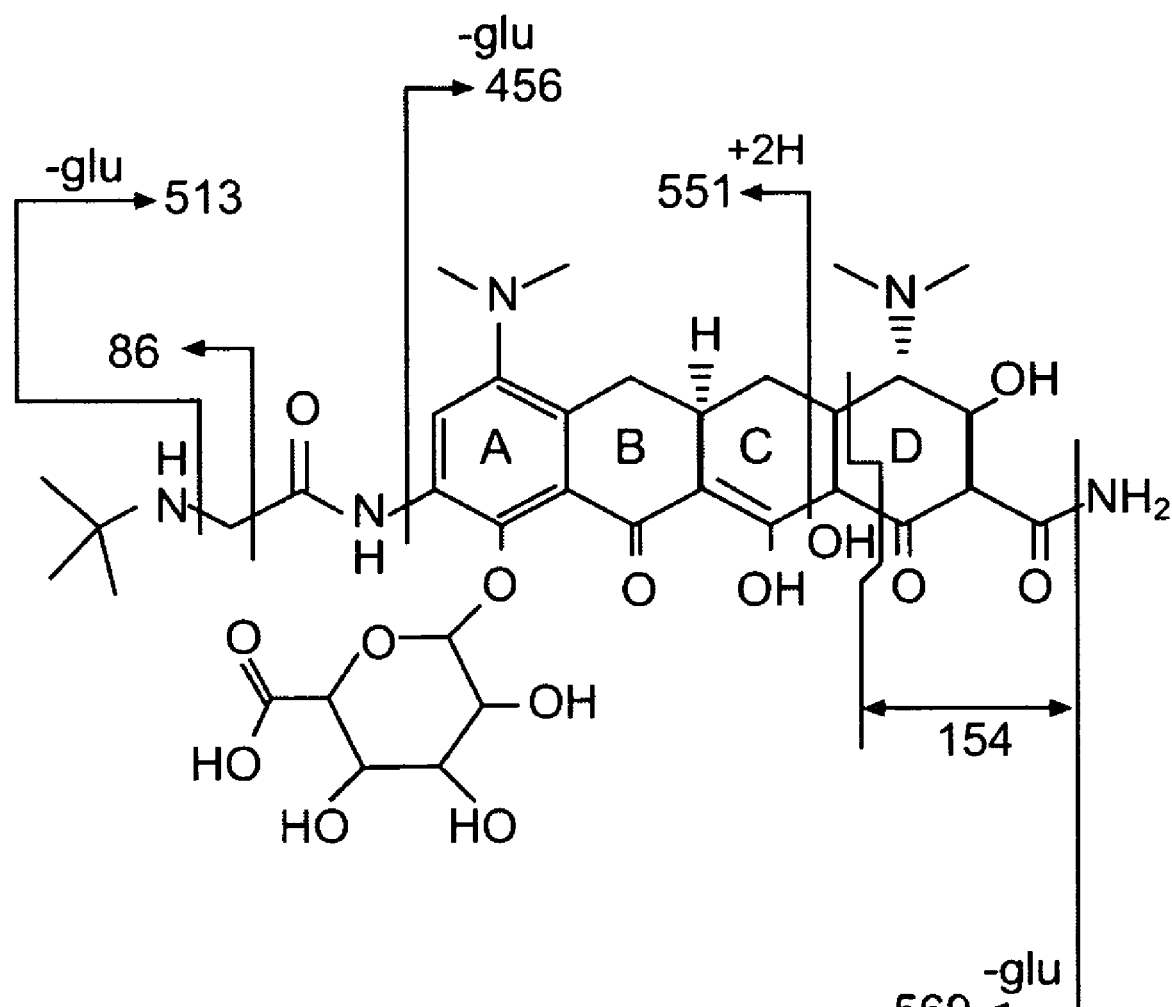
FIG. 29A shows the product ions of m/z 762 mass spectrum for M7.
Figure 29B:
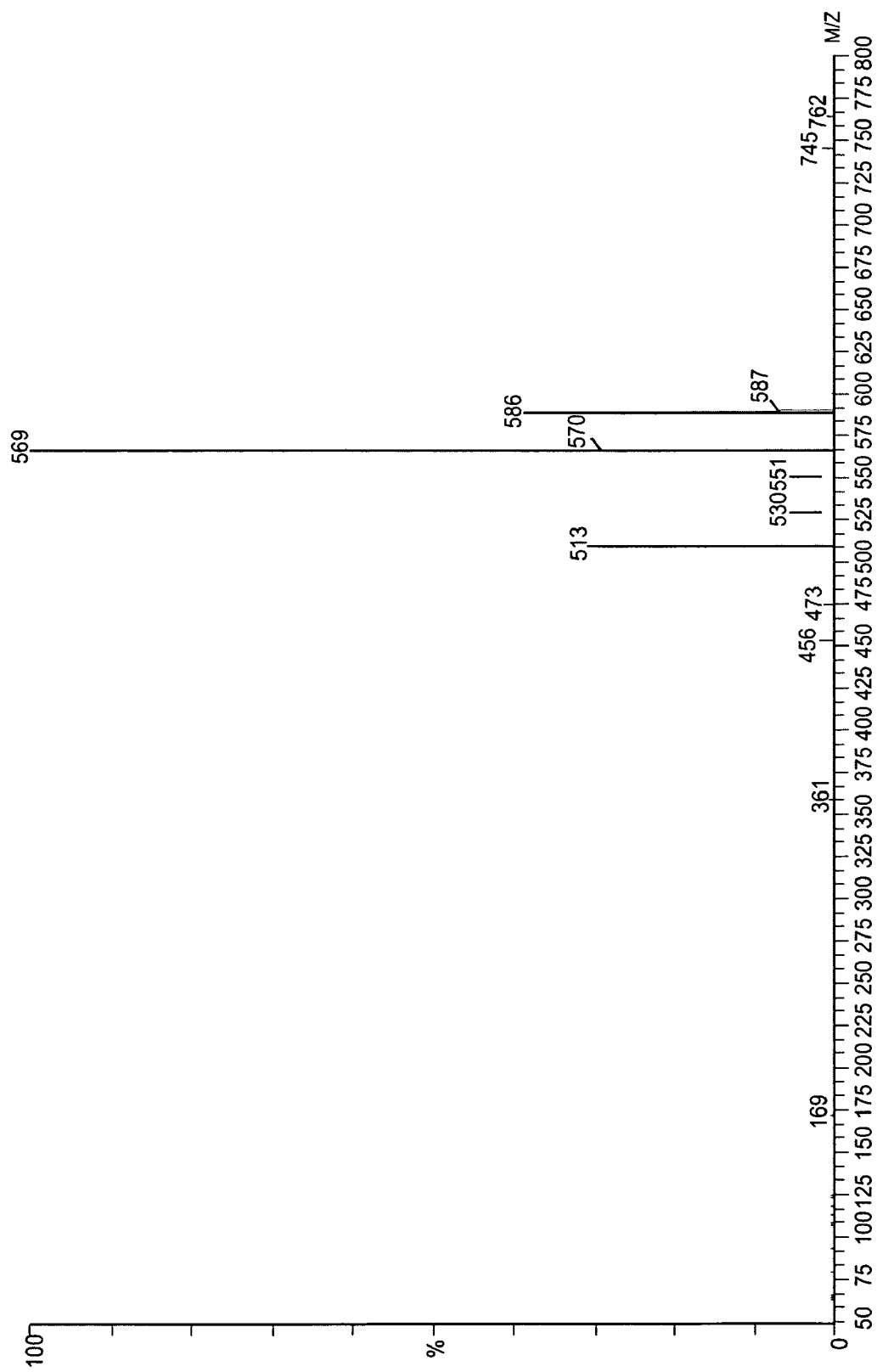
FIG. 29B is a m/z 762 mass spectrum for M7.

Metabolites M6 and M7 were observed in mouse serum and urine, and in rabbit serum. The [M+H]$^+$ for M6 and M7 was observed at m/z 762, which was 176 Da larger than tigecycline. Mass spectral data for M6 and M7 were similar. The product ions of m/z 762 mass spectrum for M7 is shown in FIGS. 29A and 29B. Neutral loss of 176 Da generated m/z 586, also the [M+H]$^+$ for tigecycline, which indicated a glucuronide of tigecycline. Product ions at m/z 569, 513, 456 and 154 were also observed for tigecycline, but did not indicate the site of conjugation. The product ion at 551 was formed by fragmentation of ring C as indicated in the fragmentation scheme, which indicated that the hydroxy group on either ring A or C was the site of glucuronidation. Losoxantrone, a tricyclic compound with a phenolic ring similar to ring A of tigecycline, is metabolized to a phenolic glucuronide. (Renner U D, Piperopoulos G, Gebhardt R, Ehninger G, Zeller K P. The oxidative biotransformation of losoxantrone (CI-941). Drug Metab Dispos 30:464-478, 2002) This indicated that the hydroxy group of ring A was the most likely site of glucuronidation of tigecycline. Metabolite M6 was proposed to be the epimer of M7 based on its HPLC retention time being earlier than that of M7. This was consistent with the tigecycline epimer eluting earlier than tigecycline (see section "Tigecycline Epimer," above). Co-chromatography of a rabbit serum extract with a human urine extract, showed that both samples contained the same tigecycline glucuronide (M7) (data not shown). Therefore, M6 and M7 were proposed to be glucuronides of the tigecycline epimer and of tigecycline, respectively.

Metabolite M9

Figure 30:
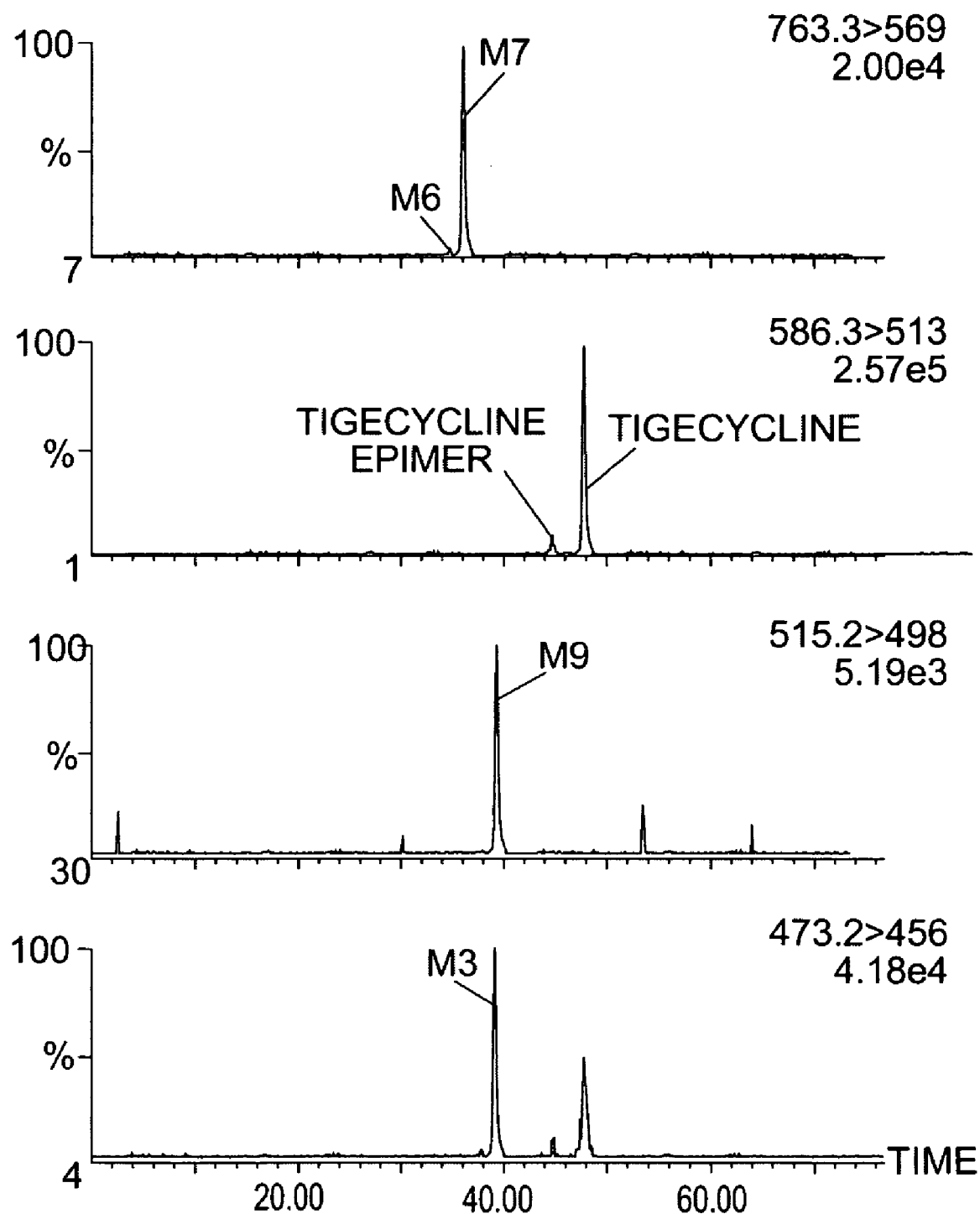
FIG. 30 shows LC/SRM chromatograms of tigecycline and its metabolites in rabbit serum with M9 indicated in the m/z 515→498 trace.
Figure 31:
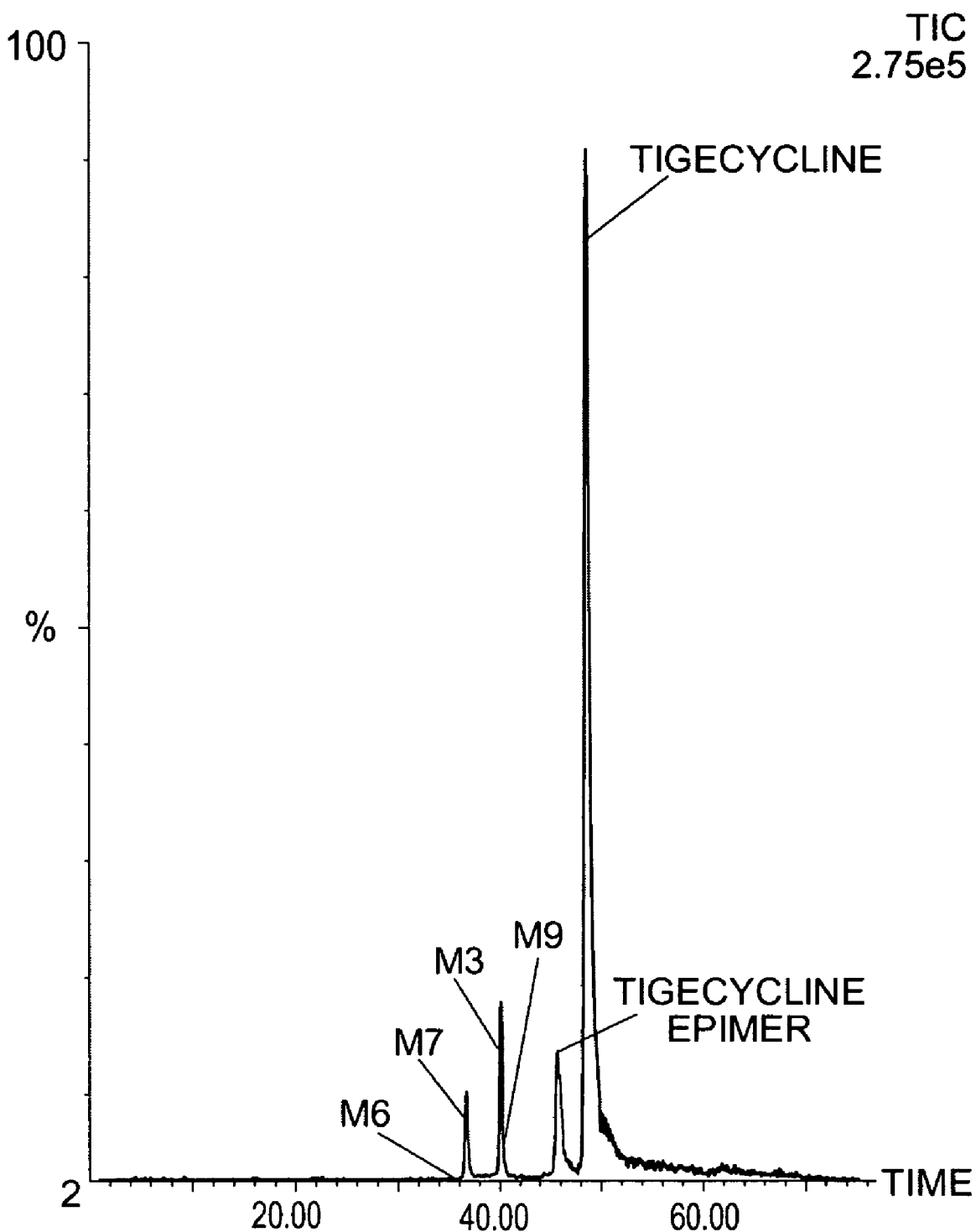
FIG. 31 is a combined LC/SRM chromatogram of rabbit serum.

Metabolite M9 was observed in rabbit serum by LC/SRM analysis. This metabolite was not observed in mouse serum or urine. FIG. 30 shows individual LC/SRM chromatograms of tigecycline and its metabolites in rabbit serum with M9 indicated in the m/z 515→498 trace. The combined LC/SRM chromatogram of rabbit serum is shown in FIG. 31.

Figure 32:
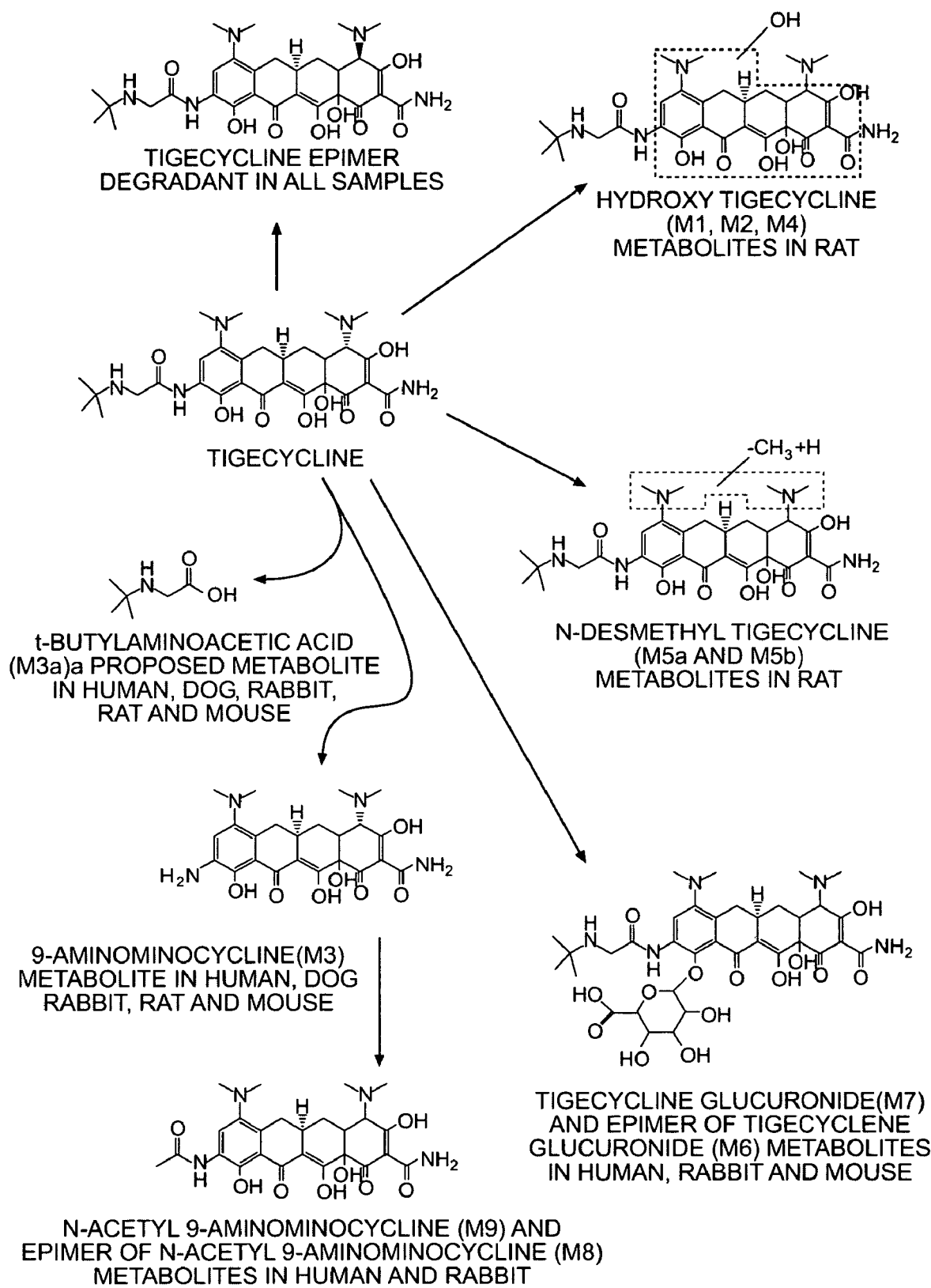
FIG. 32 is a scheme showing the proposed metabolic pathways for tigecycline in mice, rats, rabbits, dogs and humans.

Following intravenous administration of [$^{14}$C]tigecycline to healthy, male volunteers, tigecycline was the predominant radiolabeled component in serum. However, two pathways for tigecycline metabolism in humans, N-acetylation of 9-aminominocycline and glucuronidation of the parent compound, have not been observed in rats or dogs. The studies presented in this Example investigated if these pathways for tigecycline metabolism were present in mice and/or rabbits. Based on previous metabolism data and the data from the current study, the proposed metabolic pathways for tigecycline in mice, rats, rabbits, dogs and humans are shown in FIG. 32.

In both rabbits and mice, glucuronidation of tigecycline was observed. The amount of the glucuronide metabolite present could not be determined because no synthetic standard was available. In a co-chromatography experiment using human urine collected following administration of tigecycline, it was shown that the glucuronide in human urine and that in rabbit serum had identical retention times. While no co-chromatography was performed using mouse serum, the glucuronide in mouse serum had a similar retention time as the one observed in rabbits and humans and is presumed to be M7.

N-Acetyl-9-aminominocycline (M9) was observed in rabbit serum, but not mouse serum. The estimated concentrations of M9 in rabbit serum increased from 5.5 ng/mL to 20 ng/mL from 0.5 to 6 hours post-dose. These concentrations were similar to those previously reported for M9 in human serum (3-15 ng/mL) following multiple administrations of tigecycline. Additionally in rabbit serum, 9-aminominocycline (M3) was observed at concentrations as high as 545 ng/mL. While this metabolite has been observed in serum from mice, rats, dogs and humans, it was only a trace metabolite in these species. It appeared that M3 is a major metabolite in rabbits, with concentrations of up to 30% relative to tigecycline.

In summary, mice and rabbits were administered a single intravenous dose of tigecycline, then urine (mice only) and blood was collected at various times post-dose for the preparation of serum. Male CD-1 mice were administered 5 mg/kg and blood was collected 0.5, 2 and 4 hours post-dose, while urine was collected 0-4 hours post-dose. Female New Zealand White rabbits received 4 mg/kg tigecycline and blood was collected at 0.5, 2 and 6 hours post-dose. Serum samples were pooled by time point and species prior to being analyzed by LC/MS in the selected reaction monitoring mode. The presence of tigecycline (and its epimer), 9-aminominocycline (M3), tigecycline glucuronide (M7 and its epimer, M6) and N-acetyl-9-aminominocycline (M9 and its epimer, M8) was investigated. The concentrations of M3, M9 and tigecycline in rabbit serum were estimated using a non-validated LC/MS method, synthetic standards and an internal standard.

In rabbit serum, tigecycline, the epimer of tigecycline, M3, M6, M7 and M9 were detected. The estimated concentrations of tigecycline in the 0.5, 2 and 6 hour serum samples were 2020, 1040 and 287 ng/mL, respectively. The concentration of M3 also decreased with time, from 545 ng/mL at 0.5 hours to 90.2 ng/mL at 6 hours. The estimated concentrations of M9 increased over time, from 5.5 ng/mL at 0.5 hours to 8.1 ng/mL at 2 hours and 20 ng/mL at 6 hours. Concentrations of M6 and M7 could not be determined due to the lack of a synthetic standard.

In mouse serum and urine, tigecycline, the epimer of tigecycline, M3, M6 and M7 were detected. The concentrations of these compounds in mouse serum and urine were not determined. No M9 was observed in mouse serum or urine.

In summary, after a single intravenous tigecycline administration to rabbits and mice, tigecycline, its epimer, 9-aminominocycline (M3) and tigecycline glucuronide (M7, and its epimer M6) were observed in serum from both species. In addition, N-acetyl-9-aminominocycline (M9) was observed in rabbit serum. Glucuronidation of tigecycline to M7 and N-acetylation of M3 to M9 have also been observed in humans, but were not observed in rats or dogs. These compounds may be isolated by the methods described above.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An isolated glucuronide metabolite of tigecycline made by treating a human with tigecycline.

2. The metabolite of claim 1 exhibiting a mass spectral peak at m/z 762.

3. The metabolite of claim 2 further exhibiting mass spectral peaks at 586, 569, 513, 211, 154 and 86.

4. A compound according to claim 1 in substantially pure form.

5. A pharmaceutical composition comprising a compound according to claim 1 and a pharmaceutically acceptable carrier.

6. An isolated epimer of a glucuronide metabolite of tigecycline made by treating a human with tigecycline.

7. The epimer metabolite of claim 6 exhibiting a mass spectral peak at m/z 762.

8. The epimer metabolite of claim 7 further exhibiting mass spectral peaks at 586, 569, 513, 211, and 86.

9. A process for preparing a glucuronide metabolite of tigecycline comprising the steps of: a. providing a dosage of tigecycline to a human; b. obtaining a sample of serum, urine or feces from said human; c. and extracting said sample to obtain a glucuronide metabolite of tigecycline.

10. The process of claim 9 wherein the metabolite exhibits a mass spectral peak at m/z 762.

11. A process for preparing an epimer of a glucuronide metabolite of tigecycline comprising the steps of: a. provid ing a dosage of tigecycline to a human; b. obtaining a sample of feces or serum; c. and extracting said sample to obtain an epimer of a glucuronide metabolite of tigecycline.
12. The process of claim 11 wherein the epimer of the glucuronide exhibits a mass spectral peak at m/z 762.
13. An isolated compound selected from
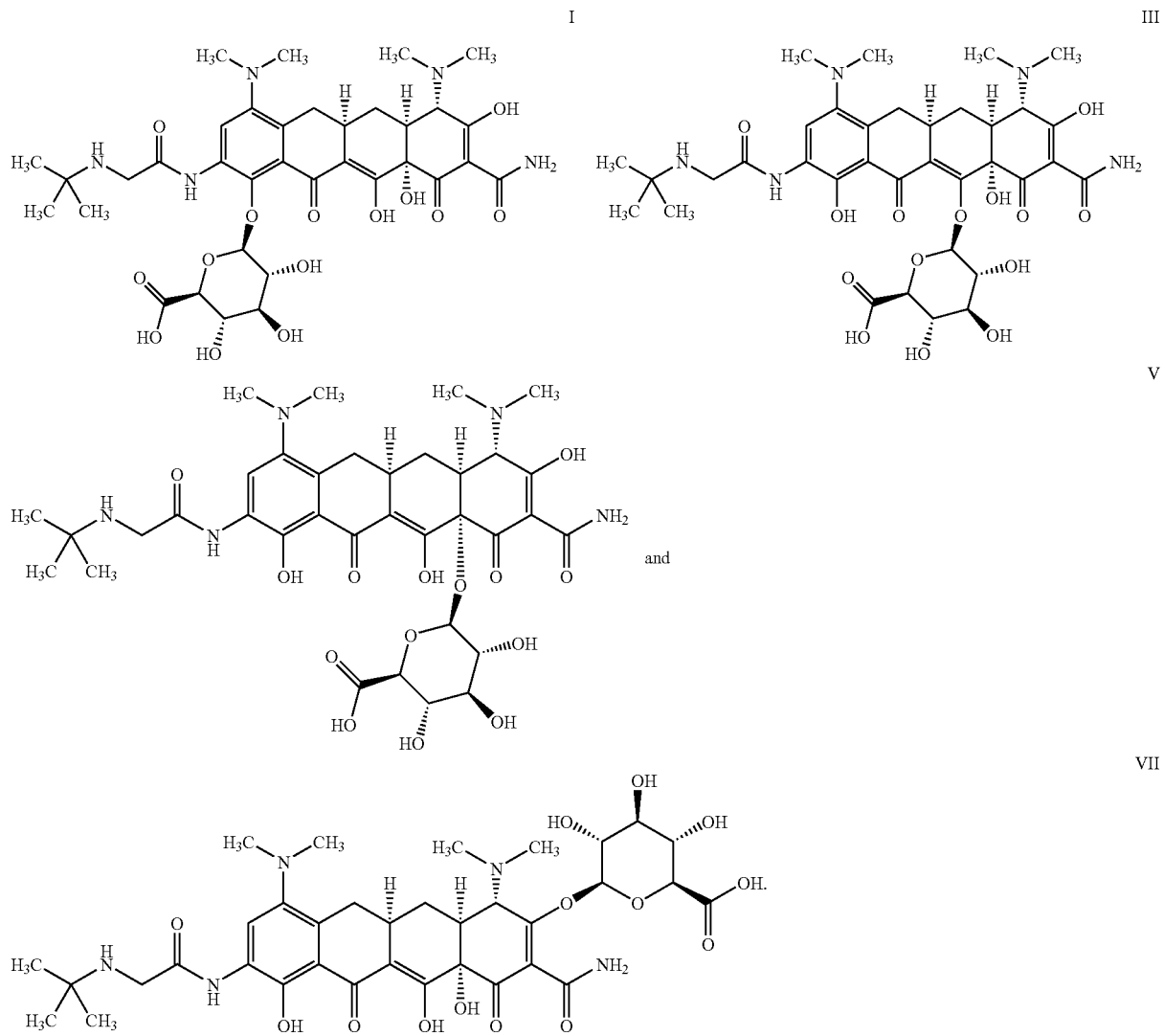
14. An isolated compound selected from
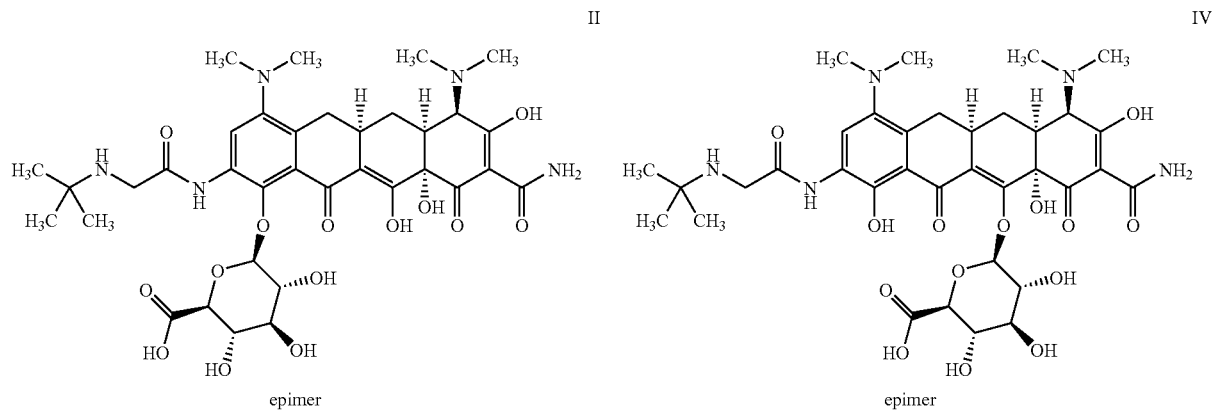

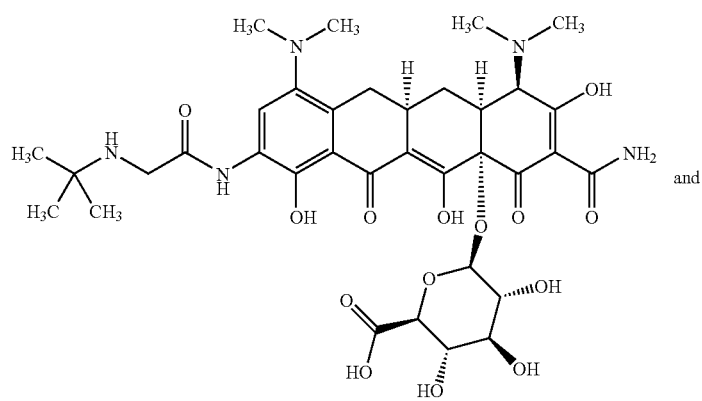
epimer
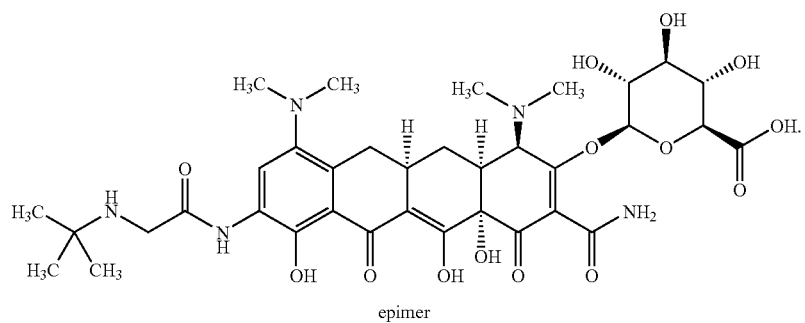
epimer
15. An isolated compound selected from:
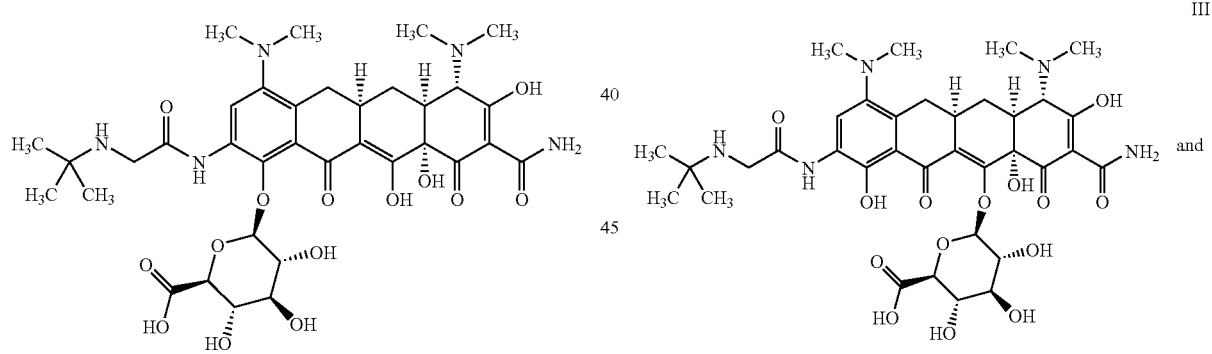
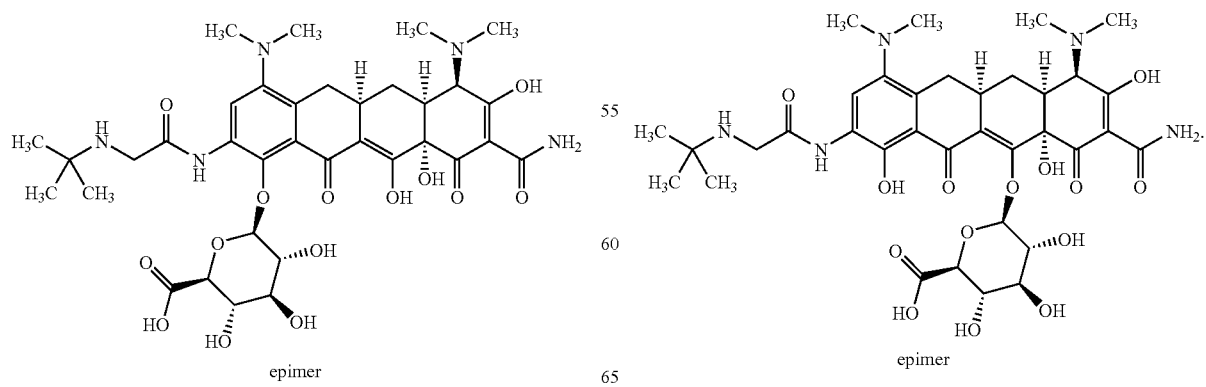

16. An isolated compound according to claim 15, selected from:

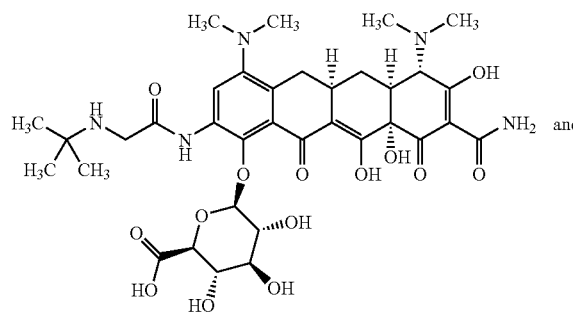
I

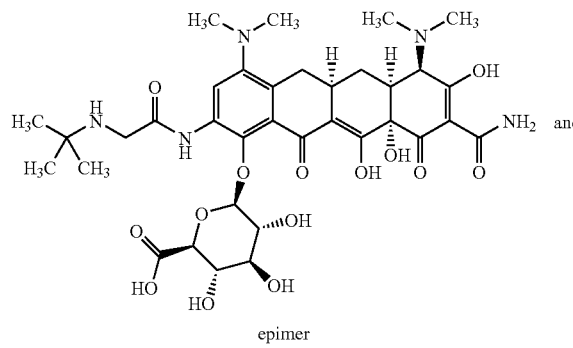
III

17. An isolated compound according to claim 15, selected from:

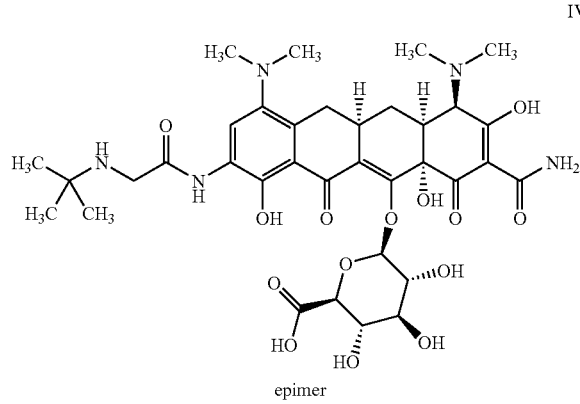
II
epimer

18. An isolated compound according to claim 15, selected from:

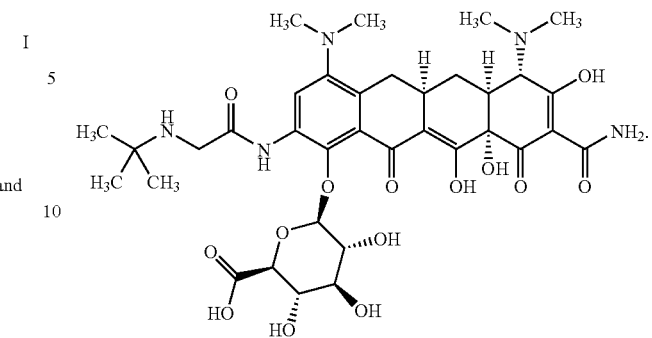
I

19. An isolated compound according to claim 15, selected from:

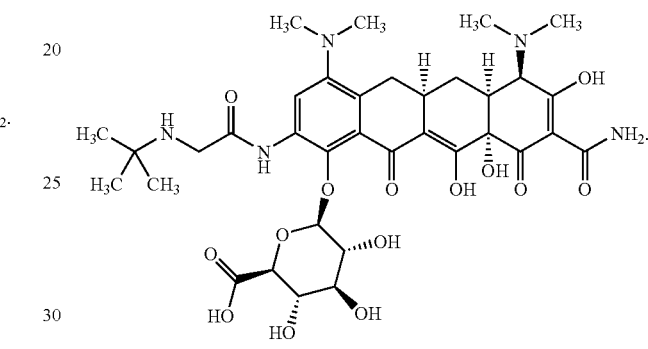
II
epimer

20. An isolated compound according to claim 15, selected from:

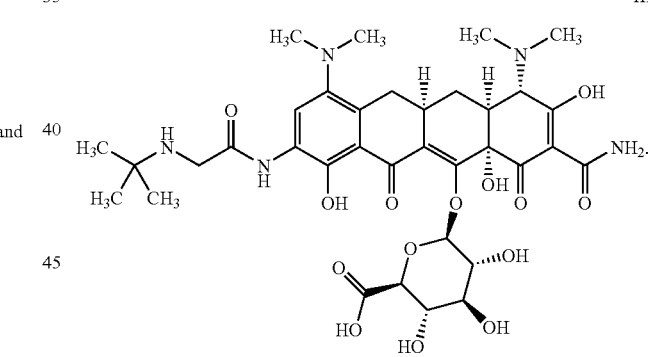
III

21. An isolated compound according to claim 15, selected from:

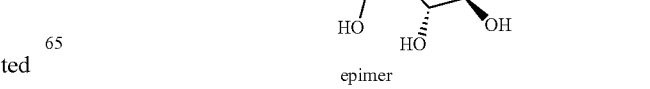
IV
epimer

22. A method of treating at least one bacterial infection, comprising: administering to a subject in need thereof a pharmaceutical composition comprising therapeutically effective amount of at least one of the compounds chosen from:
I
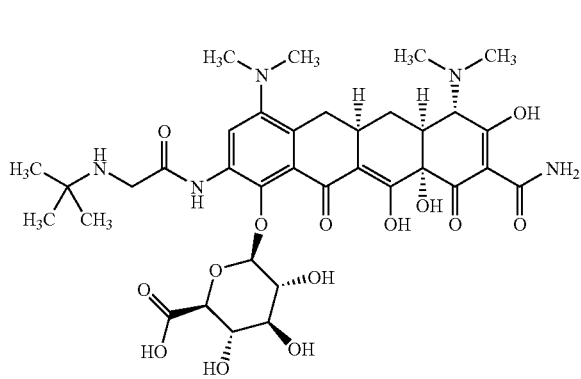
III
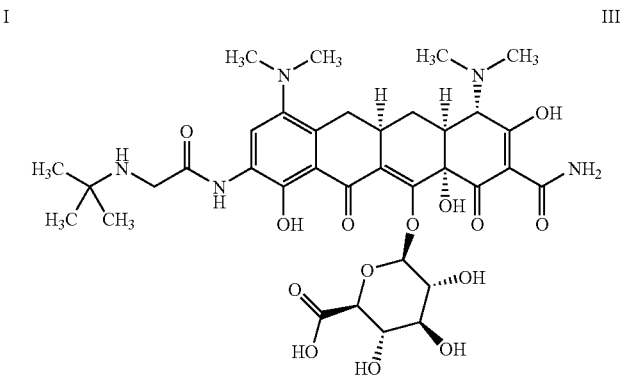
V
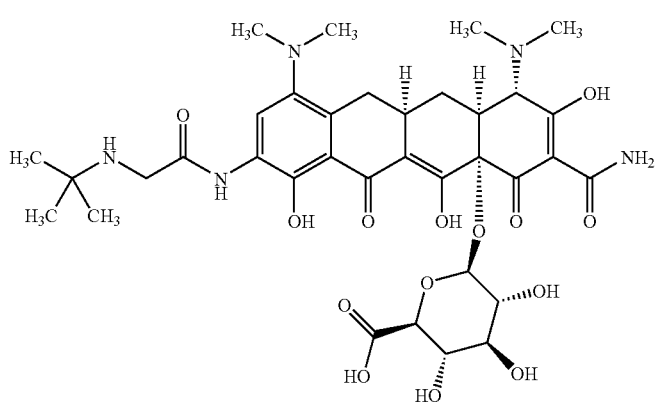
VII
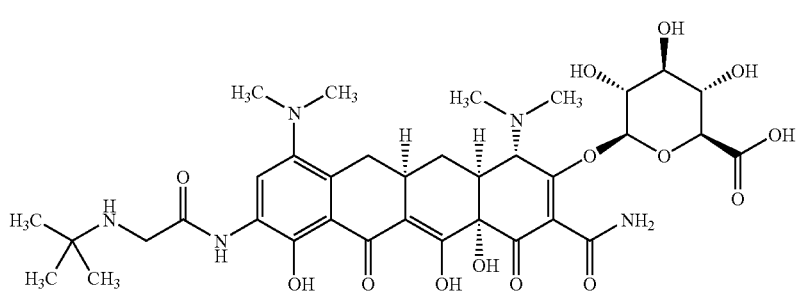
II
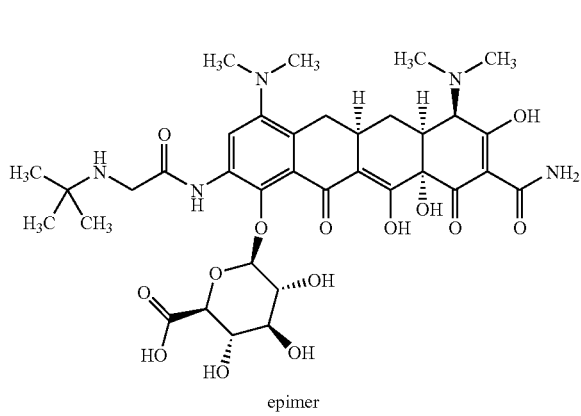
epimer
IV
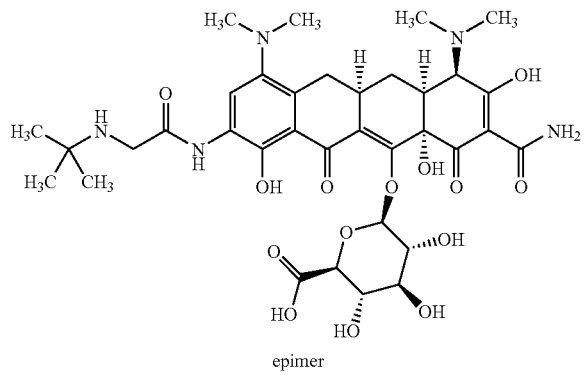
epimer -continued

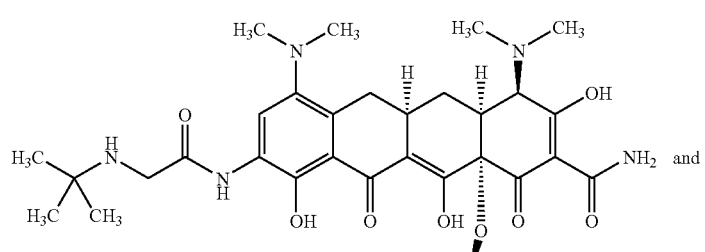
epimer

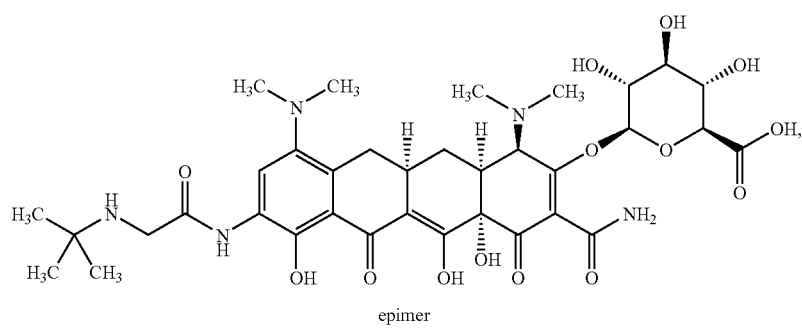
epimer and pharmaceutically acceptable salts thereof.

23. The method according to claim 22, wherein the at least one compound is chosen from I, II epimer, III, and IV epimer.

24. The method according to claim 22, wherein the at least one bacterial infection is chosen from complicated intra-abdominal infections (cIAI), complicated skin and skin structure infections (cSSSI), Community Acquired Pneumonia (CAP), Hospital Acquired Pneumonia (HAP) indications, bacterial infections caused by bacteria having the TetM and TetK resistant determinants, bone and joint infections, catheter-related Neutropenia, obstetrics and gynecological infections, and bacterial infections caused by VRE, ESBL, enterics, and rapid growing mycobacteria.

* * * * *